United States Patent [19]

Cappello

[11] Patent Number: 5,773,577
[45] Date of Patent: Jun. 30, 1998

[54] PRODUCTS COMPRISING SUBSTRATES CAPABLE OF ENZYMATIC CROSS-LINKING

[75] Inventor: Joseph Cappello, San Diego, Calif.

[73] Assignee: Protein Polymer Technologies, San Diego, Calif.

[21] Appl. No.: 397,633

[22] Filed: Mar. 2, 1995

Related U.S. Application Data

[63] Continuation-in-part of Ser. No. 205,518, Mar. 3, 1994, abandoned.

[51] Int. Cl.$^6$ ............................ C07K 14/00; A61K 38/00
[52] U.S. Cl. ........................... 530/350; 424/77; 424/422; 424/484; 424/486; 435/172.3; 514/2; 514/19; 530/353; 530/356; 530/357; 530/360; 530/402; 530/409
[58] Field of Search ........................... 424/77, 94.5, 422, 424/484, 486; 435/172.3, 193; 514/2, 19; 530/350, 353, 356, 357, 360, 402, 409

[56] References Cited

U.S. PATENT DOCUMENTS

| | | |
|---|---|---|
| 5,049,506 | 9/1991 | Stuber . |
| 5,243,038 | 9/1993 | Ferrari et al. .......................... 536/23.1 |
| 5,316,934 | 5/1994 | Kobayashi et al. ..................... 435/215 |

FOREIGN PATENT DOCUMENTS

| | | |
|---|---|---|
| WO90/05177 | 5/1990 | WIPO . |

OTHER PUBLICATIONS

Traore, F. et al. *J. Agric. Food Chem.* 39:1892–1896 (1991).

Fickenscher, et al., A Photometric Assay for Blood Coagulation Factor XIII (1991) Gosis and Haemostasis 65:535–540.

Kagan et al., "Influence of Sequence and Charge on the Specificity of Lysyl Oxidase toward Protein and Synthetic Peptide Substrates," J. Biological Chemistry (1984) 259: 11203–11207.

Pattanaik et al., "Phophorylation and Dephosphorylation Modulation of an Inverse Temperature Transition," Biochemical and Biophysical Research Communications (1991) 178: 539–545.

Sierra, D. H., "Fibrin Sealant Adhesive Systems: A Review of their Chemistry, Material Properties and Clinical Applications," J. Biomat. App. (1993) 7: 309–352.

*Primary Examiner*—Charles L. Patterson, Jr.
*Assistant Examiner*—Einar Stole
*Attorney, Agent, or Firm*—Richard F. Trecartin; Flehr Hohbach Test Albritton & Herbert LLP

[57] ABSTRACT

Polymers are provided comprising protein polymers comprising blocks of repeating units and sequences comprising amino acids, individually or in defined sequences, capable of enzyme catalyzed covalent bond formation for cross-linking, as exemplified by glutamine and/or lysine reactive for FXIII catalyzed isopeptide formation or non-amino acid polymers having side chains comprising such amino acids or sequences, which may be used for preparation of articles of manufacture, particularly cross-linkable compositions. By appropriate choice of the polymer, resorbable implantable polymers may be used in internal applications for mammals as formed objects or depots.

29 Claims, No Drawings

SEQUENCE LISTING ( 1 ) GENERAL INFORMATION:

( i i i ) NUMBER OF SEQUENCES: 105

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Val   Pro   Gly   Val   Gly
    1                                  5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Gly   Ala   Gly   Ala   Gly   Ser
    1                                  5

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /note= "where x is K or E"

( x i ) SEQUENCE DESCRIPTION: SEQ ID NO:3:

Lys Leu Xaa Leu Ala Glu Ala
1               5

( 2 ) INFORMATION FOR SEQ ID NO:4:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Gly Glu Gly Gln Gln His His Leu Gly Gly Ala Lys Gln Ala Gly
1               5                           10                          15

Asp Val ( 2 ) INFORMATION FOR SEQ ID NO:5:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Val Leu Ser Leu Ser Gln Ser Lys Val Leu Pro Val Pro Glu
1               5                           10

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Gly Gly Ala Lys Gln Ala Gly Asp Val
1               5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Gly Ala Gly Ala Gly Ser
1               5

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:8:

Val Pro Gly Val Gly
1               5

(2) INFORMATION FOR SEQ ID NO:9:

(i) SEQUENCE CHARACTERISTICS:
      (A) LENGTH: 33 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:9:

Gly Ala Pro Gly Ala Pro Gly Ser Gln Gly Ala Pro Gly Leu Gln Gly
1               5                   10                  15
Ala Pro Gly Ala Pro Gly Ser Gln Gly Ala Pro Gly Leu Gln Tyr Met
                20                  25                  30
Lys (2) INFORMATION FOR SEQ ID NO:10:

(i) SEQUENCE CHARACTERISTICS:
      (A) LENGTH: 14 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:10:

Val Leu Ser Leu Ser Gln Ser Lys Val Leu Pro Val Pro Glu
1               5                   10

(2) INFORMATION FOR SEQ ID NO:11:

(i) SEQUENCE CHARACTERISTICS:
      (A) LENGTH: 17 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:11:

Gly Glu Gly Gln Gln His His Leu Gly Gly Ala Lys Gln Ala Gly Asp
1               5                   10                  15
Val (2) INFORMATION FOR SEQ ID NO:12:

(i) SEQUENCE CHARACTERISTICS:
      (A) LENGTH: 17 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:12:

Gly Glu Gly Gln Gln His His Leu Gly Gly Ala Arg Gln Ala Gly Asp
1               5                   10                  15
Val ( 2 ) INFORMATION FOR SEQ ID NO:13:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Gly  Gly  Ala  Lys  Gln  Ala  Gly  Asp  Val
 1                  5
```

( 2 ) INFORMATION FOR SEQ ID NO:14:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:14:

```
GCTATGTTTA  AACCACGTGT  TCGCGATCCG  GGTGCCGATC  CAGGCCTGCG  ATATCAGTAC      60
GTA                                                                         63
```

( 2 ) INFORMATION FOR SEQ ID NO:15:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:15:

```
TACGTACTGA  TATCGCAGGC  CTGGATCGGC  ACCCGGATCG  CGAACACGTG  GTTTAAACAT      60
AGC                                                                         63
```

( 2 ) INFORMATION FOR SEQ ID NO:16:

( i ) SEQUENCE CHARACTERISTICS:
        ( A ) LENGTH: 226 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

```
ATGGCAGCGA  AAGGGGACCG  GTGCCCCGGG  TACTCCTGGT  CCACAAGGTC  TGCCGGGAAG      60
CCCAGGGGCT  CCGGGTACTC  CAGGTCCGCA  AGGCCTGCCG  GGTTCACCGG  GTGCTCCGGG     120
AACTCCTGGC  CCGCAGGGCT  TGCCGGGATC  CCCAGGTGCA  CCAGGAACGC  CGGGACCTCA     180
GGGTCTTCCG  GGTAGCCCTG  GTGCCTTTCC  GCTAAAGTCC  TGCCGT                    226
```

( 2 ) INFORMATION FOR SEQ ID NO:17:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

AAGAAGGAGA TATCATATGG CAGCGAAAGG GGACC    35

( 2 ) INFORMATION FOR SEQ ID NO:18:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CGCAGATCTT TAAATTACGG CAGGACTTTA GCGGAAA    37

( 2 ) INFORMATION FOR SEQ ID NO:19:

( i ) SEQUENCE CHARACTERISTICS:
        ( A ) LENGTH: 186 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:19:

GGTGCCCCGG GTACTCCTGG TCCACAAGGT CTGCCGGGAA GCCCAGGGGC TCCGGGTACT    60

CCAGGTCCGC AAGGCCTGCC GGGTTCACCG GGTGCTCCGG GAACTCCTGG CCCGCAGGGC    120

TTGCCGGGAT CCCCAGGTGC ACCAGGAACG CCGGGACCTC AGGGTCTTCC GGGTAGCCCT    180

GGTGCC    186

( 2 ) INFORMATION FOR SEQ ID NO:20:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Gly Ala Pro Gly Thr Pro Gly Pro Gln Gly Leu Pro Gly Ser Pro
1               5                   10                  15

( 2 ) INFORMATION FOR SEQ ID NO:21:

( i ) SEQUENCE CHARACTERISTICS:
        ( A ) LENGTH: 71 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Gly Ala Pro Gly Thr Pro Gly Pro Gln Gly Leu Pro Gly Ser Pro Gly
1               5                   10                  15

Ala Pro Gly Thr Pro Gly Pro Gln Gly Leu Pro Gly Ser Pro Gly Ala
                20                  25                  30

Pro Gly Thr Pro Gly Pro Gln Gly Leu Pro Gly Ser Pro Gly Ala Pro
            35                  40                  45

Gly Thr Pro Gly Glu Gly Gln Gln His His Leu Gly Gly Ala Lys Gln
                 50                  55                  60

Ala Gly Asp Val Gly Ser Pro
                 65              70

( 2 ) INFORMATION FOR SEQ ID NO:22:

( i ) SEQUENCE CHARACTERISTICS:
        ( A ) LENGTH: 123 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:22:

ATGGCAGCGA AAGGGGACCG TGCACCAGGA ACGCCGGGAG AAGGTCAACA GCACCATCTT          60

GGTGGAGCGA AACAGGCAGG CGACGTCGGT AGCCCTGGTG CCTTTCCGCT AAAGTCCTGC         120

CGT                                                                      123

( 2 ) INFORMATION FOR SEQ ID NO:23:

( i ) SEQUENCE CHARACTERISTICS:
        ( A ) LENGTH: 219 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

GGTGCCCCGG GTACTCCTGG TCCACAAGGT CTGCCGGGAA GCCCAGGGGC TCCGGGTACT          60

CCAGGTCCGC AAGGCCTGCC GGGTTCACCG GGTGCTCCGG GAACTCCTGG CCCGCAGGGC         120

TTGCCGGGAT CCCCAGGTGC ACCAGGAACG CCGGGAGAAG GTCAACAGCA CCATCTTGGT         180

GGAGCGAAAC AGGCAGGCGA CGTCGGTAGC CCTGGTGCC                               219

( 2 ) INFORMATION FOR SEQ ID NO:24:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

GATCTTCGAT CTCATCACCA TCACCATCAC TA                                        32

( 2 ) INFORMATION FOR SEQ ID NO:25:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

AGCTTAGTGA TGGTGATGGT GATGAGATCG AA                                        32

( 2 ) INFORMATION FOR SEQ ID NO:26:

( i ) SEQUENCE CHARACTERISTICS:
  ( A ) LENGTH: 762 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:26:

| Met | Asp | Pro | Val | Val | Leu | Gln | Arg | Arg | Asp | Trp | Glu | Asn | Pro | Gly | Val |
|---|---|---|---|---|---|---|---|---|---|---|---|---|---|---|---|
| 1 | | | | 5 | | | | | 10 | | | | | 15 | |
| Thr | Gln | Leu | Asn | Arg | Leu | Ala | Ala | His | Pro | Pro | Phe | Ala | Ser | Asp | Pro |
| | | | 20 | | | | | 25 | | | | | 30 | | |
| Met | Gly | Ala | Pro | Gly | Thr | Pro | Gly | Pro | Gln | Gly | Leu | Pro | Gly | Ser | Pro |
| | | | 35 | | | | 40 | | | | | 45 | | | |
| Gly | Ala | Pro | Gly | Thr | Pro | Gly | Pro | Gln | Gly | Leu | Pro | Gly | Ser | Pro | Gly |
| | 50 | | | | | 55 | | | | | 60 | | | | |
| Ala | Pro | Gly | Thr | Pro | Gly | Pro | Gln | Gly | Leu | Pro | Gly | Ser | Pro | Gly | Ala |
| 65 | | | | | 70 | | | | | 75 | | | | | 80 |
| Pro | Gly | Thr | Pro | Gly | Glu | Gly | Gln | Gln | His | His | Leu | Gly | Gly | Ala | Lys |
| | | | | 85 | | | | | 90 | | | | | 95 | |
| Gln | Ala | Gly | Asp | Val | Gly | Ser | Pro | Gly | Ala | Pro | Gly | Thr | Pro | Gly | Pro |
| | | | 100 | | | | | 105 | | | | | 110 | | |
| Gln | Gly | Leu | Pro | Gly | Ser | Pro | Gly | Ala | Pro | Gly | Thr | Pro | Gly | Pro | Gln |
| | | 115 | | | | | 120 | | | | | 125 | | | |
| Gly | Leu | Pro | Gly | Ser | Pro | Gly | Ala | Pro | Gly | Thr | Pro | Gly | Pro | Gln | Gly |
| | 130 | | | | | 135 | | | | | 140 | | | | |
| Leu | Pro | Gly | Ser | Pro | Gly | Ala | Pro | Gly | Thr | Pro | Gly | Glu | Gly | Gln | Gln |
| 145 | | | | | 150 | | | | | 155 | | | | | 160 |
| His | His | Leu | Gly | Gly | Ala | Lys | Gln | Ala | Gly | Asp | Val | Gly | Ser | Pro | Gly |
| | | | | 165 | | | | | 170 | | | | | 175 | |
| Ala | Pro | Gly | Thr | Pro | Gly | Pro | Gln | Gly | Leu | Pro | Gly | Ser | Pro | Gly | Ala |
| | | | 180 | | | | | 185 | | | | | 190 | | |
| Pro | Gly | Thr | Pro | Gly | Pro | Gln | Gly | Leu | Pro | Gly | Ser | Pro | Gly | Ala | Pro |
| | | | | 195 | | | | | 200 | | | | | 205 | |
| Gly | Thr | Pro | Gly | Pro | Gln | Gly | Leu | Pro | Gly | Ser | Pro | Gly | Ala | Pro | Gly |
| | 210 | | | | | 215 | | | | | 220 | | | | |
| Thr | Pro | Gly | Glu | Gly | Gln | Gln | His | His | Leu | Gly | Gly | Ala | Lys | Gln | Ala |
| 225 | | | | | 230 | | | | | 235 | | | | | 240 |
| Gly | Asp | Val | Gly | Ser | Pro | Gly | Ala | Pro | Gly | Thr | Pro | Gly | Pro | Gln | Gly |
| | | | | 245 | | | | | 250 | | | | | 255 | |
| Leu | Pro | Gly | Ser | Pro | Gly | Ala | Pro | Gly | Thr | Pro | Gly | Pro | Gln | Gly | Leu |
| | | | 260 | | | | | 265 | | | | | 270 | | |
| Pro | Gly | Ser | Pro | Gly | Ala | Pro | Gly | Thr | Pro | Gly | Pro | Gln | Gly | Leu | Pro |
| | | 275 | | | | | 280 | | | | | 285 | | | |
| Gly | Ser | Pro | Gly | Ala | Pro | Gly | Thr | Pro | Gly | Glu | Gly | Gln | Gln | His | His |
| | 290 | | | | | 295 | | | | | 300 | | | | |
| Leu | Gly | Gly | Ala | Lys | Gln | Ala | Gly | Asp | Val | Gly | Ser | Pro | Gly | Ala | Pro |
| 305 | | | | | 310 | | | | | 315 | | | | | 320 |
| Gly | Thr | Pro | Gly | Pro | Gln | Gly | Leu | Pro | Gly | Ser | Pro | Gly | Ala | Pro | Gly |
| | | | | 325 | | | | | 330 | | | | | 335 | |
| Thr | Pro | Gly | Pro | Gln | Gly | Leu | Pro | Gly | Ser | Pro | Gly | Ala | Pro | Gly | Thr |
| | | | 340 | | | | | 345 | | | | | 350 | | |
| Pro | Gly | Pro | Gln | Gly | Leu | Pro | Gly | Ser | Pro | Gly | Ala | Pro | Gly | Thr | Pro |
| | | 355 | | | | | 360 | | | | | 365 | | | |
| Gly | Glu | Gly | Gln | Gln | His | His | Leu | Gly | Gly | Ala | Lys | Gln | Ala | Gly | Asp |

```
                    370                          375                          380
    Val   Gly   Ser   Pro   Gly   Ala   Pro   Gly   Thr   Pro   Gly   Pro   Gln   Gly   Leu   Pro
    385                           390                          395                              400

Gly   Ser   Pro   Gly   Ala   Pro   Gly   Thr   Pro   Gly   Pro   Gln   Gly   Leu   Pro   Gly
                              405                          410                          415

Ser   Pro   Gly   Ala   Pro   Gly   Thr   Pro   Gly   Pro   Gln   Gly   Leu   Pro   Gly   Ser
                              420                          425                          430

Pro   Gly   Ala   Pro   Gly   Thr   Pro   Gly   Glu   Gly   Gln   Gln   His   His   Leu   Gly
                        435                          440                          445

Gly   Ala   Lys   Gln   Ala   Gly   Asp   Val   Gly   Ser   Pro   Gly   Ala   Pro   Gly   Thr
                  450                          455                          460

Pro   Gly   Pro   Gln   Gly   Leu   Pro   Gly   Ser   Pro   Gly   Ala   Pro   Gly   Thr   Pro
    465                           470                          475                              480

Gly   Pro   Gln   Gly   Leu   Pro   Gly   Ser   Pro   Gly   Ala   Pro   Gly   Thr   Pro   Gly
                              485                          490                          495

Pro   Gln   Gly   Leu   Pro   Gly   Ser   Pro   Gly   Ala   Pro   Gly   Thr   Pro   Gly   Glu
                        500                          505                          510

Gly   Gln   Gln   His   His   Leu   Gly   Gly   Ala   Lys   Gln   Ala   Gly   Asp   Val   Gly
                  515                          520                          525

Ser   Pro   Gly   Ala   Pro   Gly   Thr   Pro   Gly   Pro   Gln   Gly   Leu   Pro   Gly   Ser
            530                          535                          540

Pro   Gly   Ala   Pro   Gly   Thr   Pro   Gly   Pro   Gln   Gly   Leu   Pro   Gly   Ser   Pro
    545                           550                          555                              560

Gly   Ala   Pro   Gly   Thr   Pro   Gly   Pro   Gln   Gly   Leu   Pro   Gly   Ser   Pro   Gly
                              565                          570                          575

Ala   Pro   Gly   Thr   Pro   Gly   Glu   Gly   Gln   Gln   His   His   Leu   Gly   Gly   Ala
                        580                          585                          590

Lys   Gln   Ala   Gly   Asp   Val   Gly   Ser   Pro   Gly   Ala   Pro   Gly   Thr   Pro   Gly
                  595                          600                          605

Pro   Gln   Gly   Leu   Pro   Gly   Ser   Pro   Gly   Ala   Pro   Gly   Thr   Pro   Gly   Pro
            610                          615                          620

Gln   Gly   Leu   Pro   Gly   Ser   Pro   Gly   Ala   Pro   Gly   Thr   Pro   Gly   Pro   Gln
    625                           630                          635                              640

Gly   Leu   Pro   Gly   Ser   Pro   Gly   Ala   Pro   Gly   Thr   Pro   Gly   Glu   Gly   Gln
                              645                          650                          655

Gln   His   His   Leu   Gly   Gly   Ala   Lys   Gln   Ala   Gly   Asp   Val   Gly   Ser   Pro
                        660                          665                          670

Gly   Ala   Pro   Gly   Thr   Pro   Gly   Pro   Gln   Gly   Leu   Pro   Gly   Ser   Pro   Gly
                  675                          680                          685

Ala   Pro   Gly   Thr   Pro   Gly   Pro   Gln   Gly   Leu   Pro   Gly   Ser   Pro   Gly   Ala
            690                          695                          700

Pro   Gly   Thr   Pro   Gly   Pro   Gln   Gly   Leu   Pro   Gly   Ser   Pro   Gly   Ala   Pro
    705                           710                          715                              720

Gly   Thr   Pro   Gly   Glu   Gly   Gln   Gln   His   His   Leu   Gly   Gly   Ala   Lys   Gln
                              725                          730                          735

Ala   Gly   Asp   Val   Gly   Ser   Pro   Gly   Ala   Met   Asp   Pro   Gly   Arg   Tyr   Gln
                        740                          745                          750

Asp   Leu   Arg   Ser   His   His   His   His   His   His
                  755                          760
```

( 2 ) INFORMATION FOR SEQ ID NO:27:

( i ) SEQUENCE CHARACTERISTICS:

( A ) LENGTH: 71 amino acids ( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:27:

| Gly | Ala | Pro | Gly | Thr | Pro | Gly | Pro | Gln | Gly | Leu | Pro | Gly | Ser | Pro | Gly |
|---|---|---|---|---|---|---|---|---|---|---|---|---|---|---|---|
| 1 | | | | 5 | | | | | 10 | | | | | 15 | |
| Ala | Pro | Gly | Thr | Pro | Gly | Pro | Gln | Gly | Leu | Pro | Gly | Ser | Pro | Gly | Ala |
| | | | 20 | | | | | 25 | | | | | 30 | | |
| Pro | Gly | Thr | Pro | Gly | Pro | Gln | Gly | Leu | Pro | Gly | Ser | Pro | Gly | Ala | Pro |
| | | 35 | | | | | 40 | | | | | 45 | | | |
| Gly | Thr | Pro | Gly | Glu | Gly | Gln | Gln | His | His | Leu | Gly | Gly | Ala | Arg | Gln |
| | 50 | | | | | 55 | | | | | 60 | | | | |
| Ala | Gly | Asp | Val | Gly | Ser | Pro | | | | | | | | | |
| 65 | | | | | 70 | | | | | | | | | | |

( 2 ) INFORMATION FOR SEQ ID NO:28:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:28:

GTGGAGCTCG CCAGGCAGGC GACGT 25

( 2 ) INFORMATION FOR SEQ ID NO:29:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:29:

CGCCTGCCTG GCGAGCTCCA CGAAG 25

( 2 ) INFORMATION FOR SEQ ID NO:30:

( i ) SEQUENCE CHARACTERISTICS:
( A ) LENGTH: 219 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:30:

GGTGCCCCGG GTACTCCTGG TCCACAAGGT CTGCCGGGAA GCCCAGGGGC TCCGGGTACT 60
CCAGGTCCGC AAGGCCTGCC GGGTTCACCG GGTGCTCCGG GAACTCCTGG CCCGCAGGGC 120
TTGCCGGGAT CCCCAGGTGC ACCAGGAACG CCGGGAGAAG GTCAACAGCA CCATCTTGGT 180
GGAGCTCGCC AGGCAGGCGA CGTCGGTAGC CCTGGTGCC 219

( 2 ) INFORMATION FOR SEQ ID NO:31:

( i ) SEQUENCE CHARACTERISTICS:
( A ) LENGTH: 762 amino acids
( B ) TYPE: amino acid
( C ) STRANDEDNESS: single (D) TOPOLOGY: linear (ii) MOLECULE TYPE: peptide (xi) SEQUENCE DESCRIPTION: SEQ ID NO:31:

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
                20                  25                  30

Met Gly Ala Pro Gly Thr Pro Gly Pro Gln Gly Leu Pro Gly Ser Pro
            35                  40                  45

Gly Ala Pro Gly Thr Pro Gly Pro Gln Gly Leu Pro Gly Ser Pro Gly
        50                  55                  60

Ala Pro Gly Thr Pro Gly Pro Gln Gly Leu Pro Gly Ser Pro Gly Ala
 65                  70                  75                  80

Pro Gly Thr Pro Gly Glu Gly Gln Gln His His Leu Gly Gly Ala Arg
                85                  90                  95

Gln Ala Gly Asp Val Gly Ser Pro Gly Ala Pro Gly Thr Pro Gly Pro
            100                 105                 110

Gln Gly Leu Pro Gly Ser Pro Gly Ala Pro Gly Thr Pro Gly Pro Gln
            115                 120                 125

Gly Leu Pro Gly Ser Pro Gly Ala Pro Gly Thr Pro Gly Pro Gln Gly
        130                 135                 140

Leu Pro Gly Ser Pro Gly Ala Pro Gly Thr Pro Gly Glu Gly Gln Gln
145                 150                 155                 160

His His Leu Gly Gly Ala Arg Gln Ala Gly Asp Val Gly Ser Pro Gly
                165                 170                 175

Ala Pro Gly Thr Pro Gly Pro Gln Gly Leu Pro Gly Ser Pro Gly Ala
            180                 185                 190

Pro Gly Thr Pro Gly Pro Gln Gly Leu Pro Gly Ser Pro Gly Ala Pro
        195                 200                 205

Gly Thr Pro Gly Pro Gln Gly Leu Pro Gly Ser Pro Gly Ala Pro Gly
    210                 215                 220

Thr Pro Gly Glu Gly Gln Gln His His Leu Gly Gly Ala Arg Gln Ala
225                 230                 235                 240

Gly Asp Val Gly Ser Pro Gly Ala Pro Gly Thr Pro Gly Pro Gln Gly
                245                 250                 255

Leu Pro Gly Ser Pro Gly Ala Pro Gly Thr Pro Gly Pro Gln Gly Leu
            260                 265                 270

Pro Gly Ser Pro Gly Ala Pro Gly Thr Pro Gly Pro Gln Gly Leu Pro
        275                 280                 285

Gly Ser Pro Gly Ala Pro Gly Thr Pro Gly Glu Gly Gln Gln His His
    290                 295                 300

Leu Gly Gly Ala Arg Gln Ala Gly Asp Val Gly Ser Pro Gly Ala Pro
305                 310                 315                 320

Gly Thr Pro Gly Pro Gln Gly Leu Pro Gly Ser Pro Gly Ala Pro Gly
                325                 330                 335

Thr Pro Gly Pro Gln Gly Leu Pro Gly Ser Pro Gly Ala Pro Gly Thr
            340                 345                 350

Pro Gly Pro Gln Gly Leu Pro Gly Ser Pro Gly Ala Pro Gly Thr Pro
        355                 360                 365

Gly Glu Gly Gln Gln His His Leu Gly Gly Ala Arg Gln Ala Gly Asp
    370                 375                 380

Val Gly Ser Pro Gly Ala Pro Gly Thr Pro Gly Pro Gln Gly Leu Pro
385                 390                 395                 400
```

```
Gly Ser Pro Gly Ala Pro Gly Thr Pro Gly Pro Gln Gly Leu Pro Gly
            405                 410                 415
Ser Pro Gly Ala Pro Gly Thr Pro Gly Pro Gln Gly Leu Pro Gly Ser
            420                 425                 430
Pro Gly Ala Pro Gly Thr Pro Gly Glu Gly Gln Gln His His Leu Gly
            435                 440                 445
Gly Ala Arg Gln Ala Gly Asp Val Gly Ser Pro Gly Ala Pro Gly Thr
    450                 455                 460
Pro Gly Pro Gln Gly Leu Pro Gly Ser Pro Gly Ala Pro Gly Thr Pro
465                 470                 475                 480
Gly Pro Gln Gly Leu Pro Gly Ser Pro Gly Ala Pro Gly Thr Pro Gly
                485                 490                 495
Pro Gln Gly Leu Pro Gly Ser Pro Gly Ala Pro Gly Thr Pro Gly Glu
            500                 505                 510
Gly Gln Gln His His Leu Gly Gly Ala Arg Gln Ala Gly Asp Val Gly
        515                 520                 525
Ser Pro Gly Ala Pro Gly Thr Pro Gly Pro Gln Gly Leu Pro Gly Ser
        530                 535                 540
Pro Gly Ala Pro Gly Thr Pro Gly Pro Gln Gly Leu Pro Gly Ser Pro
545                 550                 555                 560
Gly Ala Pro Gly Thr Pro Gly Pro Gln Gly Leu Pro Gly Ser Pro Gly
                565                 570                 575
Ala Pro Gly Thr Pro Gly Glu Gly Gln Gln His His Leu Gly Gly Ala
            580                 585                 590
Arg Gln Ala Gly Asp Val Gly Ser Pro Gly Ala Pro Gly Thr Pro Gly
        595                 600                 605
Pro Gln Gly Leu Pro Gly Ser Pro Gly Ala Pro Gly Thr Pro Gly Pro
    610                 615                 620
Gln Gly Leu Pro Gly Ser Pro Gly Ala Pro Gly Thr Pro Gly Pro Gln
625                 630                 635                 640
Gly Leu Pro Gly Ser Pro Gly Ala Pro Gly Thr Pro Gly Glu Gly Gln
                645                 650                 655
Gln His His Leu Gly Gly Ala Arg Gln Ala Gly Asp Val Gly Ser Pro
            660                 665                 670
Gly Ala Pro Gly Thr Pro Gly Pro Gln Gly Leu Pro Gly Ser Pro Gly
        675                 680                 685
Ala Pro Gly Thr Pro Gly Pro Gln Gly Leu Pro Gly Ser Pro Gly Ala
    690                 695                 700
Pro Gly Thr Pro Gly Pro Gln Gly Leu Pro Gly Ser Pro Gly Ala Pro
705                 710                 715                 720
Gly Thr Pro Gly Glu Gly Gln Gln His His Leu Gly Gly Ala Arg Gln
                725                 730                 735
Ala Gly Asp Val Gly Ser Pro Gly Ala Met Asp Pro Gly Arg Tyr Gln
            740                 745                 750
Asp Leu Arg Ser His His His His His His
            755                 760
```

(2) INFORMATION FOR SEQ ID NO:32:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:32:

| Gly | Ala | Pro | Gly | Thr | Pro | Gly | Pro | Gln | Gly | Leu | Pro | Gly | Ser | Pro | Gly |
| 1 | | | | 5 | | | | | 10 | | | | | 15 | |

| Ala | Pro | Gly | Thr | Pro | Gly | Pro | Gln | Gly | Leu | Pro | Gly | Ser | Pro | Gly | Ala |
| | | | 20 | | | | | 25 | | | | | 30 | | |

| Pro | Gly | Thr | Pro | Gly | Pro | Gln | Gly | Leu | Pro | Gly | Ser | Pro | Gly | Ala | Pro |
| | | 35 | | | | | 40 | | | | | 45 | | | |

| Gly | Thr | Pro | Gly | Gly | Ala | Lys | Gln | Ala | Gly | Asp | Val | Gly | Ser | Pro |
| | 50 | | | | | 55 | | | | | 60 | | | |

( 2 ) INFORMATION FOR SEQ ID NO:33:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

TGCACCAGGA ACGCCGGGAG GTGCTAAACA AGCAGGAGAC GTCGGTAGCC CTGGTGCCTT    60

T    61

( 2 ) INFORMATION FOR SEQ ID NO:34:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

AAAGGCACCA GGGCTACCGA CGTCTCCTGC TTGTTTAGCA CCTCCCGGCG TTCCTGG    57

( 2 ) INFORMATION FOR SEQ ID NO:35:

( i ) SEQUENCE CHARACTERISTICS:
        ( A ) LENGTH: 195 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:35:

GGTGCCCCGG GTACTCCTGG TCCACAAGGT CTGCCGGGAA GCCCAGGGGC TCCGGGTACT    60

CCAGGTCCGC AAGGCCTGCC GGGTTCACCG GGTGCTCCGG GAACTCCTGG CCCGCAGGGC    120

TTGCCGGGAT CCCCAGGTGC ACCAGGAACG CCGGGAGGTG CTAAACAAGC AGGAGACGTC    180

GGTAGCCCTG GTGCC    195

( 2 ) INFORMATION FOR SEQ ID NO:36:

( i ) SEQUENCE CHARACTERISTICS:
        ( A ) LENGTH: 682 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20              25                  30

Met Gly Ala Pro Gly Thr Pro Gly Pro Gln Gly Leu Pro Gly Ser Pro
            35              40              45

Gly Ala Pro Gly Thr Pro Gly Pro Gln Gly Leu Pro Gly Ser Pro Gly
        50              55              60

Ala Pro Gly Thr Pro Gly Pro Gln Gly Leu Pro Gly Ser Pro Gly Ala
65              70              75              80

Pro Gly Thr Pro Gly Gly Ala Lys Gln Ala Gly Asp Val Gly Ser Pro
            85              90              95

Gly Ala Pro Gly Thr Pro Gly Pro Gln Gly Leu Pro Gly Ser Pro Gly
            100             105             110

Ala Pro Gly Thr Pro Gly Pro Gln Gly Leu Pro Gly Ser Pro Gly Ala
        115             120             125

Pro Gly Thr Pro Gly Pro Gln Gly Leu Pro Gly Ser Pro Gly Ala Pro
    130             135             140

Gly Thr Pro Gly Gly Ala Lys Gln Ala Gly Asp Val Gly Ser Pro Gly
145             150             155             160

Ala Pro Gly Thr Pro Gly Pro Gln Gly Leu Pro Gly Ser Pro Gly Ala
            165             170             175

Pro Gly Thr Pro Gly Pro Gln Gly Leu Pro Gly Ser Pro Gly Ala Pro
        180             185             190

Gly Thr Pro Gly Pro Gln Gly Leu Pro Gly Ser Pro Gly Ala Pro Gly
    195             200             205

Thr Pro Gly Gly Ala Lys Gln Ala Gly Asp Val Gly Ser Pro Gly Ala
210             215             220

Pro Gly Thr Pro Gly Pro Gln Gly Leu Pro Gly Ser Pro Gly Ala Pro
225             230             235             240

Gly Thr Pro Gly Pro Gln Gly Leu Pro Gly Ser Pro Gly Ala Pro Gly
            245             250             255

Thr Pro Gly Pro Gln Gly Leu Pro Gly Ser Pro Gly Ala Pro Gly Thr
        260             265             270

Pro Gly Gly Ala Lys Gln Ala Gly Asp Val Gly Ser Pro Gly Ala Pro
    275             280             285

Gly Thr Pro Gly Pro Gln Gly Leu Pro Gly Ser Pro Gly Ala Pro Gly
    290             295             300

Thr Pro Gly Pro Gln Gly Leu Pro Gly Ser Pro Gly Ala Pro Gly Thr
305             310             315             320

Pro Gly Pro Gln Gly Leu Pro Gly Ser Pro Gly Ala Pro Gly Thr Pro
            325             330             335

Gly Gly Ala Lys Gln Ala Gly Asp Val Gly Ser Pro Gly Ala Pro Gly
            340             345             350

Thr Pro Gly Pro Gln Gly Leu Pro Gly Ser Pro Gly Ala Pro Gly Thr
        355             360             365

Pro Gly Pro Gln Gly Leu Pro Gly Ser Pro Gly Ala Pro Gly Thr Pro
    370             375             380

Gly Pro Gln Gly Leu Pro Gly Ser Pro Gly Ala Pro Gly Thr Pro Gly
385             390             395             400

Gly Ala Lys Gln Ala Gly Asp Val Gly Ser Pro Gly Ala Pro Gly Thr
            405             410             415

Pro Gly Pro Gln Gly Leu Pro Gly Ser Pro Gly Ala Pro Gly Thr Pro
```

|     |     |     |     | 420 |     |     |     | 425 |     |     |     | 430 |     |     |
| --- | --- | --- | --- | --- | --- | --- | --- | --- | --- | --- | --- | --- | --- | --- |
| Gly | Pro | Gln | Gly | Leu | Pro | Gly | Ser | Pro | Gly | Ala | Pro | Gly | Thr | Pro | Gly |
|     |     | 435 |     |     |     | 440 |     |     |     | 445 |     |     |     |     |     |
| Pro | Gln | Gly | Leu | Pro | Gly | Ser | Pro | Gly | Ala | Pro | Gly | Thr | Pro | Gly | Gly |
| 450 |     |     |     |     | 455 |     |     |     |     | 460 |     |     |     |     |     |
| Ala | Lys | Gln | Ala | Gly | Asp | Val | Gly | Ser | Pro | Gly | Ala | Pro | Gly | Thr | Pro |
| 465 |     |     |     |     | 470 |     |     |     |     | 475 |     |     |     |     | 480 |
| Gly | Pro | Gln | Gly | Leu | Pro | Gly | Ser | Pro | Gly | Ala | Pro | Gly | Thr | Pro | Gly |
|     |     |     |     | 485 |     |     |     |     | 490 |     |     |     |     | 495 |     |
| Pro | Gln | Gly | Leu | Pro | Gly | Ser | Pro | Gly | Ala | Pro | Gly | Thr | Pro | Gly | Pro |
|     |     |     | 500 |     |     |     |     | 505 |     |     |     |     | 510 |     |     |
| Gln | Gly | Leu | Pro | Gly | Ser | Pro | Gly | Ala | Pro | Gly | Thr | Pro | Gly | Gly | Ala |
|     |     | 515 |     |     |     |     | 520 |     |     |     |     | 525 |     |     |     |
| Lys | Gln | Ala | Gly | Asp | Val | Gly | Ser | Pro | Gly | Ala | Pro | Gly | Thr | Pro | Gly |
|     | 530 |     |     |     |     | 535 |     |     |     |     | 540 |     |     |     |     |
| Pro | Gln | Gly | Leu | Pro | Gly | Ser | Pro | Gly | Ala | Pro | Gly | Thr | Pro | Gly | Pro |
| 545 |     |     |     |     | 550 |     |     |     |     | 555 |     |     |     |     | 560 |
| Gln | Gly | Leu | Pro | Gly | Ser | Pro | Gly | Ala | Pro | Gly | Thr | Pro | Gly | Pro | Gln |
|     |     |     |     | 565 |     |     |     |     | 570 |     |     |     |     | 575 |     |
| Gly | Leu | Pro | Gly | Ser | Pro | Gly | Ala | Pro | Gly | Thr | Pro | Gly | Gly | Ala | Lys |
|     |     |     | 580 |     |     |     |     | 585 |     |     |     |     | 590 |     |     |
| Gln | Ala | Gly | Asp | Val | Gly | Ser | Pro | Gly | Ala | Pro | Gly | Thr | Pro | Gly | Pro |
|     |     | 595 |     |     |     |     | 600 |     |     |     |     | 605 |     |     |     |
| Gln | Gly | Leu | Pro | Gly | Ser | Pro | Gly | Ala | Pro | Gly | Thr | Pro | Gly | Pro | Gln |
|     | 610 |     |     |     |     | 615 |     |     |     |     | 620 |     |     |     |     |
| Gly | Leu | Pro | Gly | Ser | Pro | Gly | Ala | Pro | Gly | Thr | Pro | Gly | Pro | Gln | Gly |
| 625 |     |     |     |     | 630 |     |     |     |     | 635 |     |     |     |     | 640 |
| Leu | Pro | Gly | Ser | Pro | Gly | Ala | Pro | Gly | Thr | Pro | Gly | Gly | Ala | Lys | Gln |
|     |     |     |     | 645 |     |     |     |     | 650 |     |     |     |     | 655 |     |
| Ala | Gly | Asp | Val | Gly | Ser | Pro | Gly | Ala | Met | Asp | Pro | Gly | Arg | Tyr | Gln |
|     |     |     | 660 |     |     |     |     | 665 |     |     |     |     | 670 |     |     |
| Asp | Leu | Arg | Ser | His | His | His | His | His |     |     |     |     |     |     |     |
|     |     | 675 |     |     |     | 680 |     |     |     |     |     |     |     |     |     |

( 2 ) INFORMATION FOR SEQ ID NO:37:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

| Thr | Arg | Trp | Tyr | Ser | Met | Lys | Lys | Thr | Thr | Met | Lys | Ile | Ile | Pro | Phe |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Asn | Arg | Leu | Thr | Ile |     |     |     |     |     |     |     |     |     |     |     |
|     |     |     | 20  |     |     |     |     |     |     |     |     |     |     |     |     |

( 2 ) INFORMATION FOR SEQ ID NO:38:

( i ) SEQUENCE CHARACTERISTICS:
        ( A ) LENGTH: 73 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

| Gly | Ala | Pro | Gly | Thr | Pro | Gly | Pro | Gln | Gly | Leu | Pro | Gly | Ser | Pro | Gly |
| 1 | | | | 5 | | | | | 10 | | | | | 15 | |

| Ala | Pro | Gly | Thr | Pro | Gly | Pro | Gln | Gly | Leu | Pro | Gly | Ser | Pro | Gly | Ala |
| | | | 20 | | | | | 25 | | | | | 30 | | |

| Thr | Arg | Trp | Tyr | Ser | Met | Lys | Lys | Thr | Thr | Met | Lys | Ile | Ile | Pro | Phe |
| | | | 35 | | | | 40 | | | | | 45 | | | |

| Asn | Arg | Leu | Thr | Ile | Gly | Glu | Gly | Gln | Gln | His | His | Leu | Gly | Gly | Ala |
| | | 50 | | | | | 55 | | | | | 60 | | | |

| Lys | Gln | Ala | Gly | Asp | Val | Gly | Ser | Pro |
| 65 | | | | | 70 | | | |

( 2 ) INFORMATION FOR SEQ ID NO:39:

( i ) SEQUENCE CHARACTERISTICS:
        ( A ) LENGTH: 126 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

```
ATGGCAGCGA AAGGGGACCA CCGGGTGCTA CCCGTTGGTA TTCTATGAAA AAGACTACCA      60
TGAAAATCAT TCCGTTTAAC CGCCTGACCA TTGGCGAAGG TCAACTTTCC GCTAAAGTCC     120
TGCCGT                                                                126
```

( 2 ) INFORMATION FOR SEQ ID NO:40:

( i ) SEQUENCE CHARACTERISTICS:
        ( A ) LENGTH: 225 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

```
GGTGCCCCGG GTACTCCTGG TCCACAAGGT CTGCCGGGAA GCCCAGGGGC TCCGGGTACT      60
CCAGGTCCGC AAGGCCTGCC GGGTTCACCG GGTGCTACCC GTTGGTATTC TATGAAAAAG     120
ACTACCATGA AAATCATTCC GTTTAACCGC CTGACCATTG GCGAAGGTCA ACAGCACCAT     180
CTTGGTGGAG CTCGCCAGGC AGGCGACGTC GGTAGCCCTG GTGCC                     225
```

( 2 ) INFORMATION FOR SEQ ID NO:41:

( i ) SEQUENCE CHARACTERISTICS:
        ( A ) LENGTH: 198 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:41:

| Met | Asp | Pro | Val | Val | Leu | Gln | Arg | Arg | Asp | Trp | Glu | Asn | Pro | Gly | Val |
| 1 | | | | 5 | | | | | 10 | | | | | 15 | |

| Thr | Gln | Leu | Asn | Arg | Leu | Ala | Ala | His | Pro | Pro | Phe | Ala | Ser | Asp | Pro |
| | | | | 20 | | | | | 25 | | | | | 30 | |

| Met | Gly | Ala | Pro | Gly | Thr | Pro | Gly | Pro | Gln | Gly | Leu | Pro | Gly | Ser | Pro |
| | | | | 35 | | | | | 40 | | | | | 45 | |

| Gly | Ala | Pro | Gly | Thr | Pro | Gly | Pro | Gln | Gly | Leu | Pro | Gly | Ser | Pro | Gly |

|     | 50  |     |     |     |     | 55  |     |     |     |     | 60  |     |     |     |
|-----|-----|-----|-----|-----|-----|-----|-----|-----|-----|-----|-----|-----|-----|-----|
| Ala<br>65 | Thr | Arg | Trp | Tyr<br>70 | Ser | Met | Lys | Lys | Thr<br>75 | Thr | Met | Lys | Ile | Ile | Pro<br>80 |

Phe Asn Arg Leu Thr Ile Gly Glu Gly Gln Gln His His Leu Gly Gly
               85                    90                         95

Ala Lys Gln Ala Gly Asp Val Gly Ser Pro Gly Ala Pro Gly Thr Pro
            100                   105                   110

Gly Pro Gln Gly Leu Pro Gly Ser Pro Gly Ala Pro Gly Thr Pro Gly
        115                   120                   125

Pro Gln Gly Leu Pro Gly Ser Pro Gly Ala Thr Arg Trp Tyr Ser Met
    130                   135               140

Lys Lys Thr Thr Met Lys Ile Ile Pro Phe Asn Arg Leu Thr Ile Gly
145                    150               155                160

Glu Gly Gln Gln His His Leu Gly Gly Ala Lys Gln Ala Gly Asp Val
              165                   170               175

Gly Ser Pro Gly Ala Met Asp Pro Gly Arg Tyr Gln Asp Leu Arg Ser
         180                   185               190

His His His His His His
        195

( 2 ) INFORMATION FOR SEQ ID NO:42:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

Ala Met Phe Lys Pro Arg Val Arg Asp Pro Gly Ala Asp Pro Gly Leu
1               5                     10                    15

Arg Tyr Gln Tyr Val
         20

( 2 ) INFORMATION FOR SEQ ID NO:43:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:43:

Gly Ala Pro Gly Thr Pro Gly Pro Gln Gly Leu Pro Gly Ser Pro Gly
1               5                     10                    15

Ala Pro Gly Thr Pro Gly Pro Gln Gly Leu Pro Gly Ser Pro Gly Ala
              20                   25                   30

Pro Gly Thr Pro Gly Pro Gln Gly Leu Pro Gly Ser Pro Gly Ala Pro
        35                   40                   45

Gly Thr Pro Gly Pro Gln Gly Leu Pro Gly Ser Pro Gly Ala
    50                   55               60

( 2 ) INFORMATION FOR SEQ ID NO:44:

( i ) SEQUENCE CHARACTERISTICS:
        ( A ) LENGTH: 73 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:44:

| Gly | Ala | Pro | Gly | Thr | Pro | Gly | Pro | Gln | Gly | Leu | Pro | Gly | Ser | Pro | Gly |
|---|---|---|---|---|---|---|---|---|---|---|---|---|---|---|---|
| 1 | | | | 5 | | | | | 10 | | | | | | 15 |
| Ala | Pro | Gly | Thr | Pro | Gly | Pro | Gln | Gly | Leu | Pro | Gly | Ser | Pro | Gly | Ala |
| | | | 20 | | | | | 25 | | | | | 30 | | |
| Pro | Gly | Thr | Pro | Gly | Pro | Gln | Gly | Leu | Pro | Gly | Ser | Pro | Gly | Ala | Pro |
| | | 35 | | | | | 40 | | | | | 45 | | | |
| Gly | Thr | Pro | Gly | Glu | Gly | Gln | Gln | His | His | Leu | Gly | Gly | Ala | Lys | Gln |
| | 50 | | | | | 55 | | | | | 60 | | | | |
| Ala | Gly | Asp | Val | Gly | Ser | Pro | Gly | Ala | | | | | | | |
| 65 | | | | | 70 | | | | | | | | | | |

(2) INFORMATION FOR SEQ ID NO:45:

(i) SEQUENCE CHARACTERISTICS:
    (A) LENGTH: 73 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:45:

| Gly | Ala | Pro | Gly | Thr | Pro | Gly | Pro | Gln | Gly | Leu | Pro | Gly | Ser | Pro | Gly |
|---|---|---|---|---|---|---|---|---|---|---|---|---|---|---|---|
| 1 | | | | 5 | | | | | 10 | | | | | | 15 |
| Ala | Pro | Gly | Thr | Pro | Gly | Pro | Gln | Gly | Leu | Pro | Gly | Ser | Pro | Gly | Ala |
| | | | 20 | | | | | 25 | | | | | 30 | | |
| Pro | Gly | Thr | Pro | Gly | Pro | Gln | Gly | Leu | Pro | Gly | Ser | Pro | Gly | Ala | Pro |
| | | 35 | | | | | 40 | | | | | 45 | | | |
| Gly | Thr | Pro | Gly | Glu | Gly | Gln | Gln | His | His | Leu | Gly | Gly | Ala | Arg | Gln |
| | 50 | | | | | 55 | | | | | 60 | | | | |
| Ala | Gly | Asp | Val | Gly | Ser | Pro | Gly | Ala | | | | | | | |
| 65 | | | | | 70 | | | | | | | | | | |

(2) INFORMATION FOR SEQ ID NO:46:

(i) SEQUENCE CHARACTERISTICS:
    (A) LENGTH: 65 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:46:

| Gly | Ala | Pro | Gly | Thr | Pro | Gly | Pro | Gln | Gly | Leu | Pro | Gly | Ser | Pro | Gly |
|---|---|---|---|---|---|---|---|---|---|---|---|---|---|---|---|
| 1 | | | | 5 | | | | | 10 | | | | | | 15 |
| Ala | Pro | Gly | Thr | Pro | Gly | Pro | Gln | Gly | Leu | Pro | Gly | Ser | Pro | Gly | Ala |
| | | | 20 | | | | | 25 | | | | | 30 | | |
| Pro | Gly | Thr | Pro | Gly | Pro | Gln | Gly | Leu | Pro | Gly | Ser | Pro | Gly | Ala | Pro |
| | | 35 | | | | | 40 | | | | | 45 | | | |
| Gly | Thr | Pro | Gly | Gly | Ala | Lys | Gln | Ala | Gly | Asp | Val | Gly | Ser | Pro | Gly |
| | 50 | | | | | 55 | | | | | 60 | | | | |
| Ala | | | | | | | | | | | | | | | |
| 65 | | | | | | | | | | | | | | | |

(2) INFORMATION FOR SEQ ID NO:47:

( i ) SEQUENCE CHARACTERISTICS:
( A ) LENGTH: 75 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:47:

```
Gly Ala Pro Gly Thr Pro Gly Pro Gln Gly Leu Pro Gly Ser Pro Gly
1               5                   10                  15
Ala Pro Gly Thr Pro Gly Pro Gln Gly Leu Pro Gly Ser Pro Gly Ala
            20                  25                  30
Thr Arg Trp Tyr Ser Met Lys Lys Thr Thr Met Lys Ile Ile Pro Phe
        35                  40                  45
Asn Arg Leu Thr Ile Gly Glu Gly Gln Gln His His Leu Gly Gly Ala
    50                  55                  60
Arg Gln Ala Gly Asp Val Gly Ser Pro Gly Ala
65              70                  75
```

( 2 ) INFORMATION FOR SEQ ID NO:48:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:48:

```
Leu Gly Pro Gly Gln Ser Lys Val Ile Gly
1               5                   10
```

( 2 ) INFORMATION FOR SEQ ID NO:49:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:49:

```
Gly Glu Gly Gln Gln His His Leu Gly Gly
1               5                   10
```

( 2 ) INFORMATION FOR SEQ ID NO:50:

( i ) SEQUENCE CHARACTERISTICS:
( A ) LENGTH: 897 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:50:

```
Met Asp Pro Val Val Leu Gln Arg Arg Asp Trp Glu Asn Pro Gly Val
1               5                   10                  15
Thr Gln Leu Asn Arg Leu Ala Ala His Pro Pro Phe Ala Ser Asp Pro
            20                  25                  30
Met Gly Ala Pro Gly Thr Pro Gly Pro Gln Gly Leu Pro Gly Ser Pro
        35                  40                  45
```

```
Gly  Ala  Pro  Gly  Thr  Pro  Gly  Pro  Gln  Gly  Leu  Pro  Gly  Ser  Pro  Gly
      50                      55                      60

Ala  Pro  Gly  Thr  Pro  Gly  Pro  Gln  Gly  Leu  Pro  Gly  Ser  Pro  Gly  Ala
 65                      70                      75                        80

Pro  Gly  Thr  Pro  Gly  Pro  Gln  Gly  Leu  Pro  Gly  Ser  Pro  Gly  Ala  Pro
                     85                      90                      95

Gly  Thr  Pro  Gly  Pro  Gln  Gly  Leu  Pro  Gly  Ser  Pro  Gly  Ala  Pro  Gly
               100                     105                     110

Thr  Pro  Gly  Pro  Gln  Gly  Leu  Pro  Gly  Ser  Pro  Gly  Ala  Pro  Gly  Thr
          115                     120                     125

Pro  Gly  Pro  Gln  Gly  Leu  Pro  Gly  Ser  Pro  Gly  Ala  Pro  Gly  Thr  Pro
     130                     135                     140

Gly  Pro  Gln  Gly  Leu  Pro  Gly  Ser  Pro  Gly  Ala  Pro  Gly  Thr  Pro  Gly
145                     150                     155                       160

Pro  Gln  Gly  Leu  Pro  Gly  Ser  Pro  Gly  Ala  Pro  Gly  Thr  Pro  Gly  Pro
                165                     170                     175

Gln  Gly  Leu  Pro  Gly  Ser  Pro  Gly  Ala  Pro  Gly  Thr  Pro  Gly  Pro  Gln
           180                     185                     190

Gly  Leu  Pro  Gly  Ser  Pro  Gly  Ala  Pro  Gly  Thr  Pro  Gly  Pro  Gln  Gly
      195                     200                     205

Leu  Pro  Gly  Ser  Pro  Gly  Ala  Pro  Gly  Thr  Pro  Gly  Pro  Gln  Gly  Leu
 210                     215                     220

Pro  Gly  Ser  Pro  Gly  Ala  Pro  Gly  Thr  Pro  Gly  Pro  Gln  Gly  Leu  Pro
225                     230                     235                       240

Gly  Ser  Pro  Gly  Ala  Pro  Gly  Thr  Pro  Gly  Pro  Gln  Gly  Leu  Pro  Gly
                245                     250                     255

Ser  Pro  Gly  Ala  Pro  Gly  Thr  Pro  Gly  Pro  Gln  Gly  Leu  Pro  Gly  Ser
           260                     265                     270

Pro  Gly  Ala  Pro  Gly  Thr  Pro  Gly  Pro  Gln  Gly  Leu  Pro  Gly  Ser  Pro
      275                     280                     285

Gly  Ala  Pro  Gly  Thr  Pro  Gly  Pro  Gln  Gly  Leu  Pro  Gly  Ser  Pro  Gly
 290                     295                     300

Ala  Pro  Gly  Thr  Pro  Gly  Pro  Gln  Gly  Leu  Pro  Gly  Ser  Pro  Gly  Ala
305                     310                     315                       320

Pro  Gly  Thr  Pro  Gly  Pro  Gln  Gly  Leu  Pro  Gly  Ser  Pro  Gly  Ala  Pro
                325                     330                     335

Gly  Thr  Pro  Gly  Pro  Gln  Gly  Leu  Pro  Gly  Ser  Pro  Gly  Ala  Pro  Gly
           340                     345                     350

Thr  Pro  Gly  Pro  Gln  Gly  Leu  Pro  Gly  Ser  Pro  Gly  Ala  Pro  Gly  Thr
      355                     360                     365

Pro  Gly  Pro  Gln  Gly  Leu  Pro  Gly  Ser  Pro  Gly  Ala  Pro  Gly  Thr  Pro
 370                     375                     380

Gly  Pro  Gln  Gly  Leu  Pro  Gly  Ser  Pro  Gly  Ala  Pro  Gly  Thr  Pro  Gly
385                     390                     395                       400

Pro  Gln  Gly  Leu  Pro  Gly  Ser  Pro  Gly  Ala  Pro  Gly  Thr  Pro  Gly  Pro
                405                     410                     415

Gln  Gly  Leu  Pro  Gly  Ser  Pro  Gly  Ala  Pro  Gly  Thr  Pro  Gly  Pro  Gln
           420                     425                     430

Gly  Leu  Pro  Gly  Ser  Pro  Gly  Ala  Pro  Gly  Thr  Pro  Gly  Pro  Gln  Gly
      435                     440                     445

Leu  Pro  Gly  Ser  Pro  Gly  Ala  Pro  Gly  Thr  Pro  Gly  Pro  Gln  Gly  Leu
 450                     455                     460

Pro  Gly  Ser  Pro  Gly  Ala  Pro  Gly  Thr  Pro  Gly  Pro  Gln  Gly  Leu  Pro
465                     470                     475                       480
```

```
Gly  Ser  Pro  Gly  Ala  Pro  Gly  Thr  Pro  Gly  Pro  Gln  Gly  Leu  Pro  Gly
                    485                 490                      495

Ser  Pro  Gly  Ala  Pro  Gly  Thr  Pro  Gly  Pro  Gln  Gly  Leu  Pro  Gly  Ser
               500                 505                      510

Pro  Gly  Ala  Pro  Gly  Thr  Pro  Gly  Pro  Gln  Gly  Leu  Pro  Gly  Ser  Pro
          515                 520                      525

Gly  Ala  Pro  Gly  Thr  Pro  Gly  Pro  Gln  Gly  Leu  Pro  Gly  Ser  Pro  Gly
     530                 535                      540

Ala  Pro  Gly  Thr  Pro  Gly  Pro  Gln  Gly  Leu  Pro  Gly  Ser  Pro  Gly  Ala
545                 550                      555                           560

Pro  Gly  Thr  Pro  Gly  Pro  Gln  Gly  Leu  Pro  Gly  Ser  Pro  Gly  Ala  Pro
                    565                      570                      575

Gly  Thr  Pro  Gly  Pro  Gln  Gly  Leu  Pro  Gly  Ser  Pro  Gly  Ala  Pro  Gly
               580                      585                      590

Thr  Pro  Gly  Pro  Gln  Gly  Leu  Pro  Gly  Ser  Pro  Gly  Ala  Pro  Gly  Thr
          595                      600                      605

Pro  Gly  Pro  Gln  Gly  Leu  Pro  Gly  Ser  Pro  Gly  Ala  Pro  Gly  Thr  Pro
     610                      615                      620

Gly  Pro  Gln  Gly  Leu  Pro  Gly  Ser  Pro  Gly  Ala  Pro  Gly  Thr  Pro  Gly
625                      630                      635                      640

Pro  Gln  Gly  Leu  Pro  Gly  Ser  Pro  Gly  Ala  Pro  Gly  Thr  Pro  Gly  Pro
                    645                      650                      655

Gln  Gly  Leu  Pro  Gly  Ser  Pro  Gly  Ala  Pro  Gly  Thr  Pro  Gly  Pro  Gln
               660                      665                      670

Gly  Leu  Pro  Gly  Ser  Pro  Gly  Ala  Pro  Gly  Thr  Pro  Gly  Pro  Gln  Gly
          675                      680                      685

Leu  Pro  Gly  Ser  Pro  Gly  Ala  Pro  Gly  Thr  Pro  Gly  Pro  Gln  Gly  Leu
     690                      695                      700

Pro  Gly  Ser  Pro  Gly  Ala  Pro  Gly  Thr  Pro  Gly  Pro  Gln  Gly  Leu  Pro
705                      710                      715                      720

Gly  Ser  Pro  Gly  Ala  Pro  Gly  Thr  Pro  Gly  Pro  Gln  Gly  Leu  Pro  Gly
                    725                      730                      735

Ser  Pro  Gly  Ala  Pro  Gly  Thr  Pro  Gly  Pro  Gln  Gly  Leu  Pro  Gly  Ser
               740                      745                      750

Pro  Gly  Ala  Pro  Gly  Thr  Pro  Gly  Pro  Gln  Gly  Leu  Pro  Gly  Ser  Pro
          755                      760                      765

Gly  Ala  Pro  Gly  Thr  Pro  Gly  Pro  Gln  Gly  Leu  Pro  Gly  Ser  Pro  Gly
     770                      775                      780

Ala  Pro  Gly  Thr  Pro  Gly  Pro  Gln  Gly  Leu  Pro  Gly  Ser  Pro  Gly  Ala
785                      790                      795                      800

Pro  Gly  Thr  Pro  Gly  Pro  Gln  Gly  Leu  Pro  Gly  Ser  Pro  Gly  Ala  Pro
                    805                      810                      815

Gly  Thr  Pro  Gly  Pro  Gln  Gly  Leu  Pro  Gly  Ser  Pro  Gly  Ala  Pro  Gly
               820                      825                      830

Thr  Pro  Gly  Pro  Gln  Gly  Leu  Pro  Gly  Ser  Pro  Gly  Ala  Pro  Gly  Thr
          835                      840                      845

Pro  Gly  Pro  Gln  Gly  Leu  Pro  Gly  Ser  Pro  Gly  Ala  Pro  Gly  Thr  Pro
     850                      855                      860

Gly  Pro  Gln  Gly  Leu  Pro  Gly  Ser  Pro  Gly  Ala  Met  Asp  Pro  Gly  Arg
865                      870                      875                      880

Tyr  Gln  Leu  Ser  Ala  Gly  Arg  Tyr  His  Tyr  Gln  Leu  Val  Trp  Cys  Gln
                    885                      890                      895

Lys
```

( 2 ) INFORMATION FOR SEQ ID NO:51:

( i ) SEQUENCE CHARACTERISTICS:
        ( A ) LENGTH: 225 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO:51:

```
GGTGCCCCGG  GTACTCCTGG  TCCACAAGGT  CTGCCGGGAA  GCCCAGGGGC  TCCGGGTACT        60
CCAGGTCCGC  AAGGCCTGCC  GGGTTCACCG  GGTGCTACCC  GTTGGTATTC  TATGAAAAAG       120
ACTACCATGA  AAATCATTCC  GTTTAACCGC  CTGACCATTG  GCGAAGGTCA  ACAGCACCAT       180
CTTGGTGGAG  CTCGCCAGGC  AGGCGACGTC  GGTAGCCCTG  GTGCC                       225
```

( 2 ) INFORMATION FOR SEQ ID NO:52:

( i ) SEQUENCE CHARACTERISTICS:
        ( A ) LENGTH: 198 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:52:

```
Met  Asp  Pro  Val  Val  Leu  Gln  Arg  Arg  Asp  Trp  Glu  Asn  Pro  Gly  Val
 1              5                        10                       15
Thr  Gln  Leu  Asn  Arg  Leu  Ala  Ala  His  Pro  Pro  Phe  Ala  Ser  Asp  Pro
              20                        25                       30
Met  Gly  Ala  Pro  Gly  Thr  Pro  Gly  Pro  Gln  Gly  Leu  Pro  Gly  Ser  Pro
              35                        40                       45
Gly  Ala  Pro  Gly  Thr  Pro  Gly  Pro  Gln  Gly  Leu  Pro  Gly  Ser  Pro  Gly
              50                        55                       60
Ala  Thr  Arg  Trp  Tyr  Ser  Met  Lys  Lys  Thr  Thr  Met  Lys  Ile  Ile  Pro
 65                       70                        75                       80
Phe  Asn  Arg  Leu  Thr  Ile  Gly  Glu  Gly  Gln  Gln  His  His  Leu  Gly  Gly
                   85                        90                       95
Ala  Arg  Gln  Ala  Gly  Asp  Val  Gly  Ser  Pro  Gly  Ala  Pro  Gly  Thr  Pro
              100                       105                      110
Gly  Pro  Gln  Gly  Leu  Pro  Gly  Ser  Pro  Gly  Ala  Pro  Gly  Thr  Pro  Gly
              115                       120                      125
Pro  Gln  Gly  Leu  Pro  Gly  Ser  Pro  Gly  Ala  Thr  Arg  Trp  Tyr  Ser  Met
              130                       135                      140
Lys  Lys  Thr  Thr  Met  Lys  Ile  Ile  Pro  Phe  Asn  Arg  Leu  Thr  Ile  Gly
 145                      150                      155                      160
Glu  Gly  Gln  Gln  His  His  Leu  Gly  Gly  Ala  Arg  Gln  Ala  Gly  Asp  Val
                   165                       170                      175
Gly  Ser  Pro  Gly  Ala  Met  Asp  Pro  Gly  Arg  Tyr  Gln  Asp  Leu  Arg  Ser
              180                       185                      190
His  His  His  His  His  His
              195
```

( 2 ) INFORMATION FOR SEQ ID NO:53:

( i ) SEQUENCE CHARACTERISTICS:
        ( A ) LENGTH: 829 amino acids
        ( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:53:

```
Met Asp Pro Val Val Leu Gln Arg Arg Asp Trp Glu Asn Pro Gly Val
  1               5                  10                  15

Thr Gln Leu Asn Arg Leu Ala Ala His Pro Pro Phe Ala Ser Asp Ala
             20                  25                  30

Pro Gly Thr Pro Gly Glu Gly Gln Gln His His Leu Gly Gly Ala Lys
         35                  40                  45

Gln Ala Gly Asp Val Gly Ser Pro Gly Ala Pro Gly Thr Pro Gly Pro
 50                  55                  60

Gln Gly Leu Pro Gly Ser Pro Gly Ala Pro Gly Thr Pro Gly Pro Gln
 65                  70                  75                  80

Gly Leu Pro Gly Ser Pro Gly Ala Pro Gly Thr Pro Gly Pro Gln Gly
             85                  90                  95

Leu Pro Gly Ser Pro Gly Ala Pro Gly Thr Pro Gly Pro Gln Gly Leu
            100                 105                 110

Pro Gly Ser Pro Gly Ala Pro Gly Thr Pro Gly Pro Gln Gly Leu Pro
        115                 120                 125

Gly Ser Pro Gly Ala Pro Gly Thr Pro Gly Pro Gln Gly Leu Pro Gly
    130                 135                 140

Ser Pro Gly Ala Pro Gly Thr Pro Gly Pro Gln Gly Leu Pro Gly Ser
145                 150                 155                 160

Pro Gly Ala Pro Gly Thr Pro Gly Pro Gln Gly Leu Pro Gly Ser Pro
                165                 170                 175

Gly Ala Pro Gly Thr Pro Gly Pro Gln Gly Leu Pro Gly Ser Pro Gly
            180                 185                 190

Ala Pro Gly Thr Pro Gly Pro Gln Gly Leu Pro Gly Ser Pro Gly Ala
        195                 200                 205

Pro Gly Thr Pro Gly Pro Gln Gly Leu Pro Gly Ser Pro Gly Ala Pro
    210                 215                 220

Gly Thr Pro Gly Pro Gln Gly Leu Pro Gly Ser Pro Gly Ala Pro Gly
225                 230                 235                 240

Thr Pro Gly Pro Gln Gly Leu Pro Gly Ser Pro Gly Ala Pro Gly Thr
                245                 250                 255

Pro Gly Pro Gln Gly Leu Pro Gly Ser Pro Gly Ala Pro Gly Thr Pro
            260                 265                 270

Gly Pro Gln Gly Leu Pro Gly Ser Pro Gly Ala Pro Gly Thr Pro Gly
        275                 280                 285

Pro Gln Gly Leu Pro Gly Ser Pro Gly Ala Pro Gly Thr Pro Gly Pro
    290                 295                 300

Gln Gly Leu Pro Gly Ser Pro Gly Ala Pro Gly Thr Pro Gly Pro Gln
305                 310                 315                 320

Gly Leu Pro Gly Ser Pro Gly Ala Pro Gly Thr Pro Gly Pro Gln Gly
                325                 330                 335

Leu Pro Gly Ser Pro Gly Ala Pro Gly Thr Pro Gly Pro Gln Gly Leu
            340                 345                 350

Pro Gly Ser Pro Gly Ala Pro Gly Thr Pro Gly Pro Gln Gly Leu Pro
        355                 360                 365

Gly Ser Pro Gly Ala Pro Gly Thr Pro Gly Pro Gln Gly Leu Pro Gly
    370                 375                 380

Ser Pro Gly Ala Pro Gly Thr Pro Gly Pro Gln Gly Leu Pro Gly Ser
```

```
385                    390                    395                    400
Pro  Gly  Ala  Pro  Gly  Thr  Pro  Gly  Pro  Gln  Gly  Leu  Pro  Gly  Ser  Pro
               405                    410                    415
Gly  Ala  Pro  Gly  Thr  Pro  Gly  Pro  Gln  Gly  Leu  Pro  Gly  Ser  Pro  Gly
               420                    425                    430
Ala  Pro  Gly  Thr  Pro  Gly  Pro  Gln  Gly  Leu  Pro  Gly  Ser  Pro  Gly  Ala
               435                    440                    445
Pro  Gly  Thr  Pro  Gly  Pro  Gln  Gly  Leu  Pro  Gly  Ser  Pro  Gly  Ala  Pro
          450                    455                    460
Gly  Thr  Pro  Gly  Pro  Gln  Gly  Leu  Pro  Gly  Ser  Pro  Gly  Ala  Pro  Gly
465                    470                    475                    480
Thr  Pro  Gly  Pro  Gln  Gly  Leu  Pro  Gly  Ser  Pro  Gly  Ala  Pro  Gly  Thr
               485                    490                    495
Pro  Gly  Pro  Gln  Gly  Leu  Pro  Gly  Ser  Pro  Gly  Ala  Pro  Gly  Thr  Pro
               500                    505                    510
Gly  Pro  Gln  Gly  Leu  Pro  Gly  Ser  Pro  Gly  Ala  Pro  Gly  Thr  Pro  Gly
               515                    520                    525
Pro  Gln  Gly  Leu  Pro  Gly  Ser  Pro  Gly  Ala  Pro  Gly  Thr  Pro  Gly  Pro
          530                    535                    540
Gln  Gly  Leu  Pro  Gly  Ser  Pro  Gly  Ala  Pro  Gly  Thr  Pro  Gly  Pro  Gln
545                    550                    555                    560
Gly  Leu  Pro  Gly  Ser  Pro  Gly  Ala  Pro  Gly  Thr  Pro  Gly  Pro  Gln  Gly
               565                    570                    575
Leu  Pro  Gly  Ser  Pro  Gly  Ala  Pro  Gly  Thr  Pro  Gly  Pro  Gln  Gly  Leu
               580                    585                    590
Pro  Gly  Ser  Pro  Gly  Ala  Pro  Gly  Thr  Pro  Gly  Pro  Gln  Gly  Leu  Pro
          595                    600                    605
Gly  Ser  Pro  Gly  Ala  Pro  Gly  Thr  Pro  Gly  Pro  Gln  Gly  Leu  Pro  Gly
     610                    615                    620
Ser  Pro  Gly  Ala  Pro  Gly  Thr  Pro  Gly  Pro  Gln  Gly  Leu  Pro  Gly  Ser
625                    630                    635                    640
Pro  Gly  Ala  Pro  Gly  Thr  Pro  Gly  Pro  Gln  Gly  Leu  Pro  Gly  Ser  Pro
               645                    650                    655
Gly  Ala  Pro  Gly  Thr  Pro  Gly  Pro  Gln  Gly  Leu  Pro  Gly  Ser  Pro  Gly
               660                    665                    670
Ala  Pro  Gly  Thr  Pro  Gly  Pro  Gln  Gly  Leu  Pro  Gly  Ser  Pro  Gly  Ala
               675                    680                    685
Pro  Gly  Thr  Pro  Gly  Pro  Gln  Gly  Leu  Pro  Gly  Ser  Pro  Gly  Ala  Pro
          690                    695                    700
Gly  Thr  Pro  Gly  Pro  Gln  Gly  Leu  Pro  Gly  Ser  Pro  Gly  Ala  Pro  Gly
705                    710                    715                    720
Thr  Pro  Gly  Pro  Gln  Gly  Leu  Pro  Gly  Ser  Pro  Gly  Ala  Pro  Gly  Thr
               725                    730                    735
Pro  Gly  Pro  Gln  Gly  Leu  Pro  Gly  Ser  Pro  Gly  Ala  Pro  Gly  Thr  Pro
               740                    745                    750
Gly  Pro  Gln  Gly  Leu  Pro  Gly  Ser  Pro  Gly  Ala  Pro  Gly  Thr  Pro  Gly
               755                    760                    765
Pro  Gln  Gly  Leu  Pro  Gly  Ser  Pro  Gly  Ala  Met  Asp  Pro  Gly  Arg  Tyr
          770                    775                    780
His  Met  Ala  Ala  Lys  Gly  Asp  Arg  Ala  Pro  Gly  Thr  Pro  Gly  Glu  Gly
785                    790                    795                    800
Gln  Gln  His  His  Leu  Gly  Gly  Ala  Lys  Gln  Ala  Gly  Asp  Val  Gly  Ser
               805                    810                    815
```

Pro Asp Gln Asp Leu Arg Ser His His His His His His
         820                 825

(2) INFORMATION FOR SEQ ID NO:54:

(i) SEQUENCE CHARACTERISTICS:
      (A) LENGTH: 877 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:54:

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Ala
            20                  25                  30

Pro Gly Thr Pro Gly Glu Gly Gln Gln His His Leu Gly Gly Ala Lys
        35                  40                  45

Gln Ala Gly Asp Val Gly Ser Pro Gly Ala Gly Ser Gly Ala Gly Ala
50                      55                  60

Gly Ser Gly Val Gly Val Pro Gly Val Gly Val Pro Gly Val Gly Val
65                  70                  75                      80

Pro Gly Val Gly Val Pro Gly Val Gly Val Pro Gly Val Gly Val Pro
                85                  90                  95

Gly Val Gly Val Pro Gly Val Gly Val Pro Gly Ala Gly Ala Gly Ser
                100                 105                 110

Gly Ala Gly Ala Gly Ser Gly Ala Gly Ala Gly Ser Gly Ala Gly Ala
            115                 120                 125

Gly Ser Gly Val Gly Val Pro Gly Val Gly Val Pro Gly Val Gly Val
        130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Ala Gly Ala Gly Ser
                165                 170                 175

Gly Ala Gly Ala Gly Ser Gly Ala Gly Ala Gly Ser Gly Ala Gly Ala
            180                 185                 190

Gly Ser Gly Val Gly Val Pro Gly Val Gly Val Pro Gly Val Gly Val
        195                 200                 205

Pro Gly Val Gly Val Pro Gly Val Gly Val Pro Gly Val Gly Val Pro
210                 215                 220

Gly Val Gly Val Pro Gly Val Gly Val Pro Gly Ala Gly Ala Gly Ser
225                 230                 235                 240

Gly Ala Gly Ala Gly Ser Gly Ala Gly Ala Gly Ser Gly Ala Gly Ala
                245                 250                 255

Gly Ser Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Val Gly Val Pro Gly Val Gly Val Pro Gly Ala Gly Ala Gly Ser
    290                 295                 300

Gly Ala Gly Ala Gly Ser Gly Ala Gly Ala Gly Ser Gly Ala Gly Ala
305                 310                 315                 320

Gly Ser Gly Val Gly Val Pro Gly Val Gly Val Pro Gly Val Gly Val
                325                 330                 335

Pro Gly Val Gly Val Pro Gly Val Gly Val Pro Gly Val Gly Val Pro

-continued

|     |     |     | 340 |     |     |     | 345 |     |     |     | 350 |     |     |     |
|-----|-----|-----|-----|-----|-----|-----|-----|-----|-----|-----|-----|-----|-----|-----|
| Gly | Val | Gly | Val | Pro | Gly | Val | Gly | Val | Pro | Gly | Ala | Gly | Ala | Gly | Ser |
|     |     | 355 |     |     |     |     | 360 |     |     |     |     | 365 |     |     |
| Gly | Ala | Gly | Ala | Gly | Ser | Gly | Ala | Gly | Ala | Gly | Ser | Gly | Ala | Gly | Ala |
|     |     | 370 |     |     |     |     | 375 |     |     |     |     | 380 |     |     |
| Gly | Ser | Gly | Val | Gly | Val | Pro | Gly | Val | Gly | Val | Pro | Gly | Val | Gly | Val |
| 385 |     |     |     |     |     | 390 |     |     |     |     | 395 |     |     |     | 400 |
| Pro | Gly | Val | Gly | Val | Pro | Gly | Val | Gly | Val | Pro | Gly | Val | Gly | Val | Pro |
|     |     |     |     | 405 |     |     |     |     | 410 |     |     |     |     | 415 |     |
| Gly | Val | Gly | Val | Pro | Gly | Val | Gly | Val | Pro | Gly | Ala | Gly | Ala | Gly | Ser |
|     |     |     | 420 |     |     |     |     | 425 |     |     |     |     | 430 |     |     |
| Gly | Ala | Gly | Ala | Gly | Ser | Gly | Ala | Gly | Ala | Gly | Ser | Gly | Ala | Gly | Ala |
|     |     |     | 435 |     |     |     |     | 440 |     |     |     |     | 445 |     |     |
| Gly | Ser | Gly | Val | Gly | Val | Pro | Gly | Val | Gly | Val | Pro | Gly | Val | Gly | Val |
|     |     | 450 |     |     |     |     | 455 |     |     |     |     | 460 |     |     |     |
| Pro | Gly | Val | Gly | Val | Pro | Gly | Val | Gly | Val | Pro | Gly | Val | Gly | Val | Pro |
| 465 |     |     |     |     | 470 |     |     |     |     | 475 |     |     |     |     | 480 |
| Gly | Val | Gly | Val | Pro | Gly | Val | Gly | Val | Pro | Gly | Ala | Gly | Ala | Gly | Ser |
|     |     |     |     | 485 |     |     |     |     | 490 |     |     |     |     | 495 |     |
| Gly | Ala | Gly | Ala | Gly | Ser | Gly | Ala | Gly | Ala | Gly | Ser | Gly | Ala | Gly | Ala |
|     |     |     | 500 |     |     |     |     | 505 |     |     |     |     | 510 |     |     |
| Gly | Ser | Gly | Val | Gly | Val | Pro | Gly | Val | Gly | Val | Pro | Gly | Val | Gly | Val |
|     |     | 515 |     |     |     |     | 520 |     |     |     |     | 525 |     |     |     |
| Pro | Gly | Val | Gly | Val | Pro | Gly | Val | Gly | Val | Pro | Gly | Val | Gly | Val | Pro |
|     |     | 530 |     |     |     |     | 535 |     |     |     |     | 540 |     |     |     |
| Gly | Val | Gly | Val | Pro | Gly | Val | Gly | Val | Pro | Gly | Ala | Gly | Ala | Gly | Ser |
| 545 |     |     |     |     | 550 |     |     |     |     | 555 |     |     |     |     | 560 |
| Gly | Ala | Gly | Ala | Gly | Ser | Gly | Ala | Gly | Ala | Gly | Ser | Gly | Ala | Gly | Ala |
|     |     |     |     | 565 |     |     |     |     | 570 |     |     |     |     | 575 |     |
| Gly | Ser | Gly | Val | Gly | Val | Pro | Gly | Val | Gly | Val | Pro | Gly | Val | Gly | Val |
|     |     |     | 580 |     |     |     |     | 585 |     |     |     |     | 590 |     |     |
| Pro | Gly | Val | Gly | Val | Pro | Gly | Val | Gly | Val | Pro | Gly | Val | Gly | Val | Pro |
|     |     | 595 |     |     |     |     | 600 |     |     |     |     | 605 |     |     |     |
| Gly | Val | Gly | Val | Pro | Gly | Val | Gly | Val | Pro | Gly | Ala | Gly | Ala | Gly | Ser |
|     |     | 610 |     |     |     |     | 615 |     |     |     |     | 620 |     |     |     |
| Gly | Ala | Gly | Ala | Gly | Ser | Gly | Ala | Gly | Ala | Gly | Ser | Gly | Ala | Gly | Ala |
| 625 |     |     |     |     | 630 |     |     |     |     | 635 |     |     |     |     | 640 |
| Gly | Ser | Gly | Val | Gly | Val | Pro | Gly | Val | Gly | Val | Pro | Gly | Val | Gly | Val |
|     |     |     |     | 645 |     |     |     |     | 650 |     |     |     |     | 655 |     |
| Pro | Gly | Val | Gly | Val | Pro | Gly | Val | Gly | Val | Pro | Gly | Val | Gly | Val | Pro |
|     |     |     | 660 |     |     |     |     | 665 |     |     |     |     | 670 |     |     |
| Gly | Val | Gly | Val | Pro | Gly | Val | Gly | Val | Pro | Gly | Ala | Gly | Ala | Gly | Ser |
|     |     |     | 675 |     |     |     |     | 680 |     |     |     |     | 685 |     |     |
| Gly | Ala | Gly | Ala | Gly | Ser | Gly | Ala | Gly | Ala | Gly | Ser | Gly | Ala | Gly | Ala |
|     |     |     | 690 |     |     |     |     | 695 |     |     |     |     | 700 |     |     |
| Gly | Ser | Gly | Val | Gly | Val | Pro | Gly | Val | Gly | Val | Pro | Gly | Val | Gly | Val |
| 705 |     |     |     |     | 710 |     |     |     |     | 715 |     |     |     |     | 720 |
| Pro | Gly | Val | Gly | Val | Pro | Gly | Val | Gly | Val | Pro | Gly | Val | Gly | Val | Pro |
|     |     |     |     | 725 |     |     |     |     | 730 |     |     |     |     | 735 |     |
| Gly | Val | Gly | Val | Pro | Gly | Val | Gly | Val | Pro | Gly | Ala | Gly | Ala | Gly | Ser |
|     |     |     | 740 |     |     |     |     | 745 |     |     |     |     | 750 |     |     |
| Gly | Ala | Gly | Ala | Gly | Ser | Gly | Ala | Gly | Ala | Gly | Ser | Gly | Ala | Gly | Ala |
|     |     |     | 755 |     |     |     |     | 760 |     |     |     |     | 765 |     |     |

-continued

```
Gly  Ser  Gly  Val  Gly  Val  Pro  Gly  Val  Gly  Val  Pro  Gly  Val  Gly  Val
     770                      775                      780

Pro  Gly  Val  Gly  Val  Pro  Gly  Val  Gly  Val  Pro  Gly  Val  Gly  Val  Pro
785                      790                      795                      800

Gly  Val  Gly  Val  Pro  Gly  Val  Gly  Val  Pro  Gly  Ala  Gly  Ala  Gly  Ser
                    805                      810                      815

Gly  Ala  Gly  Ala  Gly  Ser  Gly  Ala  Gly  Ala  Met  Asp  Pro  Gly  Arg  Tyr
               820                      825                      830

His  Met  Ala  Ala  Lys  Gly  Asp  Arg  Ala  Pro  Gly  Thr  Pro  Gly  Glu  Gly
          835                      840                      845

Gln  Gln  His  His  Leu  Gly  Gly  Ala  Lys  Gln  Ala  Gly  Asp  Val  Gly  Ser
     850                      855                      860

Pro  Asp  Gln  Asp  Leu  Arg  Ser  His  His  His  His  His
865                      870                      875
```

( 2 ) INFORMATION FOR SEQ ID NO:55:

( i ) SEQUENCE CHARACTERISTICS:
        ( A ) LENGTH: 64 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:55:

```
Gly  Ala  Gly  Ala  Gly  Ser  Gly  Ala  Gly  Ala  Gly  Ser  Gly  Ala  Gly  Ala
1                   5                        10                       15

Gly  Ser  Gly  Ala  Gly  Ala  Gly  Ser  Gly  Val  Gly  Val  Pro  Gly  Val  Gly
               20                       25                       30

Val  Pro  Gly  Val  Gly  Val  Pro  Gly  Val  Gly  Val  Pro  Gly  Lys  Gly  Val
          35                       40                       45

Pro  Gly  Val  Gly  Val  Pro  Gly  Val  Gly  Val  Pro  Gly  Val  Gly  Val  Pro
     50                       55                       60
```

( 2 ) INFORMATION FOR SEQ ID NO:56:

( i ) SEQUENCE CHARACTERISTICS:
        ( A ) LENGTH: 64 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:56:

```
Gly  Ala  Gly  Ala  Gly  Ser  Gly  Ala  Gly  Ala  Gly  Ser  Gly  Ala  Gly  Ala
1                   5                        10                       15

Gly  Ser  Gly  Ala  Gly  Ala  Gly  Ser  Gly  Val  Gly  Val  Pro  Gly  Val  Gly
               20                       25                       30

Val  Pro  Gly  Val  Gly  Val  Pro  Gly  Val  Gly  Val  Pro  Gly  Glu  Gly  Val
          35                       40                       45

Pro  Gly  Val  Gly  Val  Pro  Gly  Val  Gly  Val  Pro  Gly  Val  Gly  Val  Pro
     50                       55                       60
```

( 2 ) INFORMATION FOR SEQ ID NO:57:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear (i i) MOLECULE TYPE: other nucleic acid (x i) SEQUENCE DESCRIPTION: SEQ ID NO:57:

CTGGAGCGGG TGCCTGCATG TACATCCGAG T  31

(2) INFORMATION FOR SEQ ID NO:58:

(i) SEQUENCE CHARACTERISTICS:
(A) LENGTH: 35 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:58:

CCGAGACCTC GCCCACGGAC GTACATGTAG GCTCA  35

(2) INFORMATION FOR SEQ ID NO:59:

(i) SEQUENCE CHARACTERISTICS:
(A) LENGTH: 192 base pairs
(B) TYPE: nucleic acid
(C) STRANDEDNESS: double
(D) TOPOLOGY: linear (i i) MOLECULE TYPE: cDNA (x i) SEQUENCE DESCRIPTION: SEQ ID NO:59:

GGTGCCGGTT CTGGAGCTGG CGCGGGCTCT GGAGTAGGTG TGCCAGGTGT AGGAGTTCCG  60

GGTGTAGGCG TTCCGGGAGT TGGTGTACCT GGAGTGGGTG TTCCAGGCGT AGGTGTGCCC  120

GGGGTAGGAG TACCAGGGGT AGGCGTCCCT GGAGCGGGTG CTGGTAGCGG CGCAGGCGCG  180

GGCTCTGGAG CG  192

(2) INFORMATION FOR SEQ ID NO:60:

(i) SEQUENCE CHARACTERISTICS:
(A) LENGTH: 64 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:60:

Gly Ala Gly Ser Gly Ala Gly Ala Gly Ser Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Ala Gly Ala Gly Ser Gly Ala Gly Ala Gly Ser Gly Ala
    50              55                  60

(2) INFORMATION FOR SEQ ID NO:61:

(i) SEQUENCE CHARACTERISTICS:
(A) LENGTH: 201 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:61:

| ATGGCAGCGA | AAGGGGACCG | GGCTCTGGTG | TTGGAGTGCC | AGGTGTCGGT | GTTCCGGGTG | 60 |
| TAGGCGTTCC | GGGAGTTGGT | GTACCTGGAA | AGGTGTTCCG | GGGGTAGGTG | TGCCGGGCGT | 120 |
| TGGAGTACCA | GGTGTAGGCG | TCCCGGGAGC | GGGTGCTGGT | AGCGGCGCAG | GCGCGGGCTC | 180 |
| TTTCCGCTAA | AGTCCTGCCG | T | | | | 201 |

( 2 ) INFORMATION FOR SEQ ID NO:62:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:62:

| AAGAAGGAGA | TATCATATGG | CAGCGAAAGG | GGACC | 35 |

( 2 ) INFORMATION FOR SEQ ID NO:63:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:63:

| CGCAGATCTT | TAAATTACGG | CAGGACTTTA | GCGGAAA | 37 |

( 2 ) INFORMATION FOR SEQ ID NO:64:

( i ) SEQUENCE CHARACTERISTICS:
        ( A ) LENGTH: 192 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:64:

| GGTGCCGGTT | CTGGAGCTGG | CGCGGGCTCT | GGTGTTGGAG | TGCCAGGTGT | CGGTGTTCCG | 60 |
| GGTGTAGGCG | TTCCGGGAGT | TGGTGTACCT | GGAAAAGGTG | TTCCGGGGGT | AGGTGTGCCG | 120 |
| GGCGTTGGAG | TACCAGGTGT | AGGCGTCCCG | GGAGCGGGTG | CTGGTAGCGG | CGCAGGCGCG | 180 |
| GGCTCTGGAG | CG | | | | | 192 |

( 2 ) INFORMATION FOR SEQ ID NO:65:

( i ) SEQUENCE CHARACTERISTICS:
        ( A ) LENGTH: 64 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:65:

| Gly | Ala | Gly | Ser | Gly | Ala | Gly | Ala | Gly | Ser | Gly | Val | Gly | Val | Pro | Gly |
| 1 | | | | 5 | | | | | 10 | | | | | 15 | |
| Val | Gly | Val | Pro | Gly | Val | Gly | Val | Pro | Gly | Val | Gly | Val | Pro | Gly | Lys |
| | | | 20 | | | | | 25 | | | | | 30 | | |
| Gly | Val | Pro | Gly | Val | Gly | Val | Pro | Gly | Val | Gly | Val | Pro | Gly | Val | Gly |
| | | 35 | | | | | 40 | | | | | 45 | | | |

```
            Val Pro Gly Ala Gly Ala Gly Ser Gly Ala Gly Ala Gly Ser Gly Ala
                50                  55                  60
```

( 2 ) INFORMATION FOR SEQ ID NO:66:

( i ) SEQUENCE CHARACTERISTICS:
        ( A ) LENGTH: 192 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:66:

```
GGTGCCGGTT CTGGAGCTGG CGCGGGCTCT GGTGTTGGAG TGCCAGGTGT CGGTGTTCCG      60
GGTGTAGGCG TTCCGGGAGT TGGTGTACCT GGAGAAGGTG TTCCGGGGGT AGGTGTGCCG     120
GGCGTTGGAG TACCAGGTGT AGGCGTCCCG GGAGCGGGTG CTGGTAGCGG CGCAGGCGCG     180
GGCTCTGGAG CG                                                         192
```

( 2 ) INFORMATION FOR SEQ ID NO:67:

( i ) SEQUENCE CHARACTERISTICS:
        ( A ) LENGTH: 64 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:67:

```
Gly Ala Gly Ser Gly Ala Gly Ala Gly Ser Gly Val Gly Val Pro Gly
 1               5                  10                  15
Val Gly Val Pro Gly Val Gly Val Pro Gly Val Gly Val Pro Gly Glu
                20                  25                  30
Gly Val Pro Gly Val Gly Val Pro Gly Val Gly Val Pro Gly Val Gly
                35                  40                  45
Val Pro Gly Ala Gly Ala Gly Ser Gly Ala Gly Ala Gly Ser Gly Ala
                50                  55                  60
```

( 2 ) INFORMATION FOR SEQ ID NO:68:

( i ) SEQUENCE CHARACTERISTICS:
        ( A ) LENGTH: 884 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:68:

```
Met Asp Pro Val Val Leu Gln Arg Arg Asp Trp Glu Asn Pro Gly Val
 1               5                  10                  15
Thr Gln Leu Asn Arg Leu Ala Ala His Pro Pro Phe Ala Ser Asp Pro
                20                  25                  30
Met Gly Ala Gly Ser Gly Ala Gly Ala Gly Ser Gly Val Gly Val Pro
                35                  40                  45
Gly Val Gly Val Pro Gly Val Gly Val Pro Gly Val Gly Val Pro Gly
                50                  55                  60
Lys Gly Val Pro Gly Val Gly Val Pro Gly Val Gly Val Pro Gly Val
 65                 70                  75                  80
Gly Val Pro Gly Ala Gly Ala Gly Ser Gly Ala Gly Ala Gly Ser Gly
                85                  90                  95
```

```
Ala Gly Ala Gly Ser Gly Ala Gly Ala Gly Ser Gly Val Gly Val Pro
            100                 105                 110
Gly Val Gly Val Pro Gly Val Gly Val Pro Gly Val Gly Val Pro Gly
            115                 120                 125
Lys Gly Val Pro Gly Val Gly Val Pro Gly Val Gly Val Pro Gly Val
            130                 135                 140
Gly Val Pro Gly Ala Gly Ala Gly Ser Gly Ala Gly Ala Gly Ser Gly
145                 150                 155                 160
Ala Gly Ala Gly Ser Gly Ala Gly Ala Gly Ser Gly Val Gly Val Pro
                    165                 170                 175
Gly Val Gly Val Pro Gly Val Gly Val Pro Gly Val Gly Val Pro Gly
                    180                 185                 190
Lys Gly Val Pro Gly Val Gly Val Pro Gly Val Gly Val Pro Gly Val
                    195                 200                 205
Gly Val Pro Gly Ala Gly Ala Gly Ser Gly Ala Gly Ala Gly Ser Gly
            210                 215                 220
Ala Gly Ala Gly Ser Gly Ala Gly Ala Gly Ser Gly Val Gly Val Pro
225                 230                 235                 240
Gly Val Gly Val Pro Gly Val Gly Val Pro Gly Val Gly Val Pro Gly
                    245                 250                 255
Lys Gly Val Pro Gly Val Gly Val Pro Gly Val Gly Val Pro Gly Val
                    260                 265                 270
Gly Val Pro Gly Ala Gly Ala Gly Ser Gly Ala Gly Ala Gly Ser Gly
            275                 280                 285
Ala Gly Ala Gly Ser Gly Ala Gly Ala Gly Ser Gly Val Gly Val Pro
            290                 295                 300
Gly Val Gly Val Pro Gly Val Gly Val Pro Gly Val Gly Val Pro Gly
305                 310                 315                 320
Lys Gly Val Pro Gly Val Gly Val Pro Gly Val Gly Val Pro Gly Val
                    325                 330                 335
Gly Val Pro Gly Ala Gly Ala Gly Ser Gly Ala Gly Ala Gly Ser Gly
            340                 345                 350
Ala Gly Ala Gly Ser Gly Ala Gly Ala Gly Ser Gly Val Gly Val Pro
            355                 360                 365
Gly Val Gly Val Pro Gly Val Gly Val Pro Gly Val Gly Val Pro Gly
            370                 375                 380
Lys Gly Val Pro Gly Val Gly Val Pro Gly Val Gly Val Pro Gly Val
385                 390                 395                 400
Gly Val Pro Gly Ala Gly Ala Gly Ser Gly Ala Gly Ala Gly Ser Gly
                    405                 410                 415
Ala Gly Ala Gly Ser Gly Ala Gly Ala Gly Ser Gly Val Gly Val Pro
                    420                 425                 430
Gly Val Gly Val Pro Gly Val Gly Val Pro Gly Val Gly Val Pro Gly
                    435                 440                 445
Lys Gly Val Pro Gly Val Gly Val Pro Gly Val Gly Val Pro Gly Val
                    450                 455                 460
Gly Val Pro Gly Ala Gly Ala Gly Ser Gly Ala Gly Ala Gly Ser Gly
465                 470                 475                 480
Ala Gly Ala Gly Ser Gly Ala Gly Ala Gly Ser Gly Val Gly Val Pro
                    485                 490                 495
Gly Val Gly Val Pro Gly Val Gly Val Pro Gly Val Gly Val Pro Gly
            500                 505                 510
Lys Gly Val Pro Gly Val Gly Val Pro Gly Val Gly Val Pro Gly Val
```

|     |     |     | 515 |     |     |     | 520 |     |     |     | 525 |     |     |
| --- | --- | --- | --- | --- | --- | --- | --- | --- | --- | --- | --- | --- | --- |
| Gly | Val | Pro | Gly | Ala | Gly | Ala | Gly | Ser | Gly | Ala | Gly | Ala | Gly | Ser | Gly |
|     |     |     | 530 |     |     |     | 535 |     |     |     | 540 |     |     |     |     |
| Ala | Gly | Ala | Gly | Ser | Gly | Ala | Gly | Ala | Gly | Ser | Gly | Val | Gly | Val | Pro |
| 545 |     |     |     |     | 550 |     |     |     |     | 555 |     |     |     |     | 560 |
| Gly | Val | Gly | Val | Pro | Gly | Val | Gly | Val | Pro | Gly | Val | Gly | Val | Pro | Gly |
|     |     |     |     | 565 |     |     |     |     | 570 |     |     |     |     | 575 |     |
| Lys | Gly | Val | Pro | Gly | Val | Gly | Val | Pro | Gly | Val | Gly | Val | Pro | Gly | Val |
|     |     |     | 580 |     |     |     |     | 585 |     |     |     |     | 590 |     |     |
| Gly | Val | Pro | Gly | Ala | Gly | Ala | Gly | Ser | Gly | Ala | Gly | Ala | Gly | Ser | Gly |
|     |     | 595 |     |     |     |     | 600 |     |     |     |     | 605 |     |     |     |
| Ala | Gly | Ala | Gly | Ser | Gly | Ala | Gly | Ala | Gly | Ser | Gly | Val | Gly | Val | Pro |
|     |     | 610 |     |     |     |     | 615 |     |     |     |     | 620 |     |     |     |
| Gly | Val | Gly | Val | Pro | Gly | Val | Gly | Val | Pro | Gly | Val | Gly | Val | Pro | Gly |
| 625 |     |     |     |     | 630 |     |     |     |     | 635 |     |     |     |     | 640 |
| Lys | Gly | Val | Pro | Gly | Val | Gly | Val | Pro | Gly | Val | Gly | Val | Pro | Gly | Val |
|     |     |     |     | 645 |     |     |     |     | 650 |     |     |     |     | 655 |     |
| Gly | Val | Pro | Gly | Ala | Gly | Ala | Gly | Ser | Gly | Ala | Gly | Ala | Gly | Ser | Gly |
|     |     |     | 660 |     |     |     |     | 665 |     |     |     |     | 670 |     |     |
| Ala | Gly | Ala | Gly | Ser | Gly | Ala | Gly | Ala | Gly | Ser | Gly | Val | Gly | Val | Pro |
|     |     |     | 675 |     |     |     |     | 680 |     |     |     |     | 685 |     |     |
| Gly | Val | Gly | Val | Pro | Gly | Val | Gly | Val | Pro | Gly | Val | Gly | Val | Pro | Gly |
|     |     | 690 |     |     |     |     | 695 |     |     |     |     | 700 |     |     |     |
| Lys | Gly | Val | Pro | Gly | Val | Gly | Val | Pro | Gly | Val | Gly | Val | Pro | Gly | Val |
| 705 |     |     |     |     | 710 |     |     |     |     | 715 |     |     |     |     | 720 |
| Gly | Val | Pro | Gly | Ala | Gly | Ala | Gly | Ser | Gly | Ala | Gly | Ala | Gly | Ser | Gly |
|     |     |     |     | 725 |     |     |     |     | 730 |     |     |     |     | 735 |     |
| Ala | Gly | Ala | Gly | Ser | Gly | Ala | Gly | Ala | Gly | Ser | Gly | Val | Gly | Val | Pro |
|     |     |     | 740 |     |     |     |     | 745 |     |     |     |     | 750 |     |     |
| Gly | Val | Gly | Val | Pro | Gly | Val | Gly | Val | Pro | Gly | Val | Gly | Val | Pro | Gly |
|     |     |     | 755 |     |     |     |     | 760 |     |     |     |     | 765 |     |     |
| Lys | Gly | Val | Pro | Gly | Val | Gly | Val | Pro | Gly | Val | Gly | Val | Pro | Gly | Val |
|     |     | 770 |     |     |     |     | 775 |     |     |     |     | 780 |     |     |     |
| Gly | Val | Pro | Gly | Ala | Gly | Ala | Gly | Ser | Gly | Ala | Gly | Ala | Gly | Ser | Gly |
| 785 |     |     |     |     | 790 |     |     |     |     | 795 |     |     |     |     | 800 |
| Ala | Gly | Ala | Gly | Ser | Gly | Ala | Gly | Ala | Gly | Ser | Gly | Val | Gly | Val | Pro |
|     |     |     |     | 805 |     |     |     |     | 810 |     |     |     |     | 815 |     |
| Gly | Val | Gly | Val | Pro | Gly | Val | Gly | Val | Pro | Gly | Val | Gly | Val | Pro | Gly |
|     |     |     | 820 |     |     |     |     | 825 |     |     |     |     | 830 |     |     |
| Lys | Gly | Val | Pro | Gly | Val | Gly | Val | Pro | Gly | Val | Gly | Val | Pro | Gly | Val |
|     |     |     | 835 |     |     |     |     | 840 |     |     |     |     | 845 |     |     |
| Gly | Val | Pro | Gly | Ala | Gly | Ala | Gly | Ser | Gly | Ala | Gly | Ala | Gly | Ser | Gly |
|     |     | 850 |     |     |     |     | 855 |     |     |     |     | 860 |     |     |     |
| Ala | Gly | Ala | Met | Asp | Pro | Gly | Arg | Tyr | Gln | Asp | Leu | Arg | Ser | His | His |
| 865 |     |     |     |     | 870 |     |     |     |     | 875 |     |     |     |     | 880 |
| His | His | His | His |     |     |     |     |     |     |     |     |     |     |     |     |

(2) INFORMATION FOR SEQ ID NO:69:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:69:

Leu Gly Pro Gly Gln Ser Lys Val Ile Gly
1               5                   10

( 2 ) INFORMATION FOR SEQ ID NO:70:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:70:

Leu Gly Pro Gly Gln Ser Lys Val Ile Gly
1               5                   10

( 2 ) INFORMATION FOR SEQ ID NO:71:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:71:

Gly Gly Leu Lys Gly Gly Gly
1               5

( 2 ) INFORMATION FOR SEQ ID NO:72:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:72:

Gly Gly Leu Lys Gly Gly Gly
1               5

( 2 ) INFORMATION FOR SEQ ID NO:73:

( i ) SEQUENCE CHARACTERISTICS:
        ( A ) LENGTH: 262 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:73:

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
                20                  25                  30

Met Gly Ala Gly Ser Gly Ala Gly Ala Gly Ser Gly Val Gly Val Pro
            35                  40                  45

Gly Val Gly Val Pro Gly Val Gly Val Pro Gly Val Gly Val Pro Gly
        50                  55                  60

Gly Gly Leu Lys Gly Gly Gly Gly Val Pro Gly Val Gly Val Pro Gly

|    |    |    |    | 65  |    |    |    | 70  |    |    |    | 75  |    |    |    | 80  |
|----|----|----|----|-----|----|----|----|-----|----|----|----|-----|----|----|----|-----|

Val Gly Val Pro Gly Val Gly Val Pro Gly Ala Gly Ala Gly Ser Gly
                    85                  90                  95

Ala Gly Ala Gly Ser Gly Ala Gly Ala Gly Ser Gly Ala Gly Ala Gly
            100                 105                 110

Ser Gly Val Gly Val Pro Gly Val Gly Val Pro Gly Val Gly Val Pro
        115                 120                 125

Gly Val Gly Val Pro Gly Gly Leu Lys Gly Gly Gly Gly Val Pro
    130                 135                 140

Gly Val Gly Val Pro Gly Val Gly Val Pro Gly Val Gly Val Pro Gly
145                 150                 155                 160

Ala Gly Ala Gly Ser Gly Ala Gly Ala Gly Ser Gly Ala Gly Ala Gly
                165                 170                 175

Ser Gly Ala Gly Ala Gly Ser Gly Val Gly Val Pro Gly Val Gly Val
            180                 185                 190

Pro Gly Val Gly Val Pro Gly Val Gly Val Pro Gly Gly Gly Leu Lys
        195                 200                 205

Gly Gly Gly Gly Val Pro Gly Val Gly Val Pro Gly Val Gly Val Pro
    210                 215                 220

Gly Val Gly Val Pro Gly Ala Gly Ala Gly Ser Gly Ala Gly Ala Gly
225                 230                 235                 240

Ser Gly Ala Gly Ala Met Asp Pro Gly Arg Tyr Gln Asp Leu Arg Ser
                245                 250                 255

His His His His His His
            260

( 2 ) INFORMATION FOR SEQ ID NO:74:

( i ) SEQUENCE CHARACTERISTICS:
        ( A ) LENGTH: 251 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:74:

Met Asp Pro Val Val Leu Gln Arg Arg Asp Trp Glu Asn Pro Gly Val
1                   5                   10                  15

Thr Gln Leu Asn Arg Leu Ala Ala His Pro Pro Phe Ala Ser Asp Pro
                20                  25                  30

Met Gly Ala Gly Ser Gly Ala Gly Ala Gly Ser Gly Val Gly Val Pro
            35                  40                  45

Gly Val Gly Val Pro Gly Leu Gly Pro Gly Gln Ser Lys Val Ile Gly
        50                  55                  60

Gly Val Pro Gly Val Gly Val Pro Gly Val Gly Val Pro Gly Val Gly
65                  70                  75                  80

Val Pro Gly Ala Gly Ala Gly Ser Gly Ala Gly Ala Gly Ser Gly Ala
                85                  90                  95

Gly Ala Gly Ser Gly Ala Gly Ala Gly Ser Gly Val Gly Val Pro Gly
            100                 105                 110

Val Gly Val Pro Gly Leu Gly Pro Gly Gln Ser Lys Val Ile Gly Gly
        115                 120                 125

Val Pro Gly Val Gly Val Pro Gly Val Gly Val Pro Gly Val Gly Val
    130                 135                 140

Pro Gly Ala Gly Ala Gly Ser Gly Ala Gly Ala Gly Ser Gly Ala Gly
145                 150                 155                 160

|     |     |     |     |     |     |     |     |     |     |     |     |     |     |     |
| --- | --- | --- | --- | --- | --- | --- | --- | --- | --- | --- | --- | --- | --- | --- |
| Ala | Gly | Ser | Gly | Ala | Gly | Ala | Gly | Ser | Gly | Val | Gly | Val | Pro | Gly | Val |
|     |     |     |     | 165 |     |     |     | 170 |     |     |     |     | 175 |     |     |
| Gly | Val | Pro | Gly | Val | Gly | Val | Pro | Gly | Val | Gly | Val | Pro | Gly | Leu | Gly |
|     |     |     | 180 |     |     |     | 185 |     |     |     |     |     | 190 |     |     |
| Pro | Gly | Gln | Ser | Lys | Val | Ile | Gly | Val | Pro | Gly | Val | Gly | Val | Pro |
|     |     | 195 |     |     |     |     | 200 |     |     |     |     | 205 |     |     |
| Gly | Val | Gly | Val | Pro | Gly | Val | Gly | Val | Pro | Gly | Ala | Gly | Ala | Gly | Ser |
|     | 210 |     |     |     |     | 215 |     |     |     |     | 220 |     |     |     |     |
| Gly | Ala | Gly | Ala | Gly | Ser | Gly | Ala | Gly | Ala | Met | Asp | Pro | Gly | Arg | Tyr |
| 225 |     |     |     |     | 230 |     |     |     |     | 235 |     |     |     |     | 240 |
| Gln | Asp | Leu | Arg | Ser | His | His | His | His | His |
|     |     |     |     | 245 |     |     |     |     | 250 |

( 2 ) INFORMATION FOR SEQ ID NO:75:

( i ) SEQUENCE CHARACTERISTICS:
       ( A ) LENGTH: 281 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:75:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Asp | Pro | Val | Val | Leu | Gln | Arg | Arg | Asp | Trp | Glu | Asn | Pro | Gly | Val |
| 1   |     |     |     | 5   |     |     |     |     | 10  |     |     |     |     | 15  |     |
| Thr | Gln | Leu | Asn | Arg | Leu | Ala | Ala | His | Pro | Pro | Phe | Ala | Ser | Asp | Ala |
|     |     |     | 20  |     |     |     |     | 25  |     |     |     |     | 30  |     |     |
| Pro | Gly | Thr | Pro | Gly | Gly | Leu | Lys | Gly | Gly | Gly | Gly | Ser | Pro | Gly | Ala |
|     |     | 35  |     |     |     |     | 40  |     |     |     |     | 45  |     |     |     |
| Gly | Ser | Gly | Ala | Gly | Ala | Gly | Ser | Gly | Val | Gly | Val | Pro | Gly | Val | Gly |
|     | 50  |     |     |     |     | 55  |     |     |     |     | 60  |     |     |     |     |
| Val | Pro | Gly | Val | Gly | Val | Pro | Gly | Val | Gly | Val | Pro | Gly | Val | Gly | Val |
| 65  |     |     |     |     | 70  |     |     |     |     | 75  |     |     |     |     | 80  |
| Pro | Gly | Val | Gly | Val | Pro | Gly | Val | Gly | Val | Pro | Gly | Val | Gly | Val | Pro |
|     |     |     |     | 85  |     |     |     |     | 90  |     |     |     |     | 95  |     |
| Gly | Ala | Gly | Ala | Gly | Ser | Gly | Ala | Gly | Ala | Gly | Ser | Gly | Ala | Gly | Ala |
|     |     |     | 100 |     |     |     |     | 105 |     |     |     |     | 110 |     |     |
| Gly | Ser | Gly | Ala | Gly | Ala | Gly | Ser | Gly | Val | Gly | Val | Pro | Gly | Val | Gly |
|     |     | 115 |     |     |     |     | 120 |     |     |     |     | 125 |     |     |     |
| Val | Pro | Gly | Val | Gly | Val | Pro | Gly | Val | Gly | Val | Pro | Gly | Val | Gly | Val |
|     | 130 |     |     |     |     | 135 |     |     |     |     | 140 |     |     |     |     |
| Pro | Gly | Val | Gly | Val | Pro | Gly | Val | Gly | Val | Pro | Gly | Val | Gly | Val | Pro |
| 145 |     |     |     |     | 150 |     |     |     |     | 155 |     |     |     |     | 160 |
| Gly | Ala | Gly | Ala | Gly | Ser | Gly | Ala | Gly | Ala | Gly | Ser | Gly | Ala | Gly | Ala |
|     |     |     |     | 165 |     |     |     |     | 170 |     |     |     |     | 175 |     |
| Gly | Ser | Gly | Ala | Gly | Ala | Gly | Ser | Gly | Val | Gly | Val | Pro | Gly | Val | Gly |
|     |     |     | 180 |     |     |     |     | 185 |     |     |     |     | 190 |     |     |
| Val | Pro | Gly | Val | Gly | Val | Pro | Gly | Val | Gly | Val | Pro | Gly | Val | Gly | Val |
|     |     | 195 |     |     |     |     | 200 |     |     |     |     | 205 |     |     |     |
| Pro | Gly | Val | Gly | Val | Pro | Gly | Val | Gly | Val | Pro | Gly | Val | Gly | Val | Pro |
|     | 210 |     |     |     |     | 215 |     |     |     |     | 220 |     |     |     |     |
| Gly | Ala | Gly | Ala | Gly | Ser | Gly | Ala | Gly | Ala | Gly | Ser | Gly | Ala | Gly | Ala |
| 225 |     |     |     |     | 230 |     |     |     |     | 235 |     |     |     |     | 240 |
| Met | Asp | Pro | Gly | Arg | Tyr | His | Met | Ala | Ala | Lys | Gly | Asp | Arg | Ala | Pro |
|     |     |     |     | 245 |     |     |     |     | 250 |     |     |     |     | 255 |     |

Gly Thr Pro Gly Gly Leu Lys Gly Gly Gly Gly Ser Pro Asp Gln Asp
            260                 265                 270

Leu Arg Ser His His His His His His
        275             280

( 2 ) INFORMATION FOR SEQ ID NO:76:

( i ) SEQUENCE CHARACTERISTICS:
        ( A ) LENGTH: 287 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:76:

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Ala
            20                  25                  30

Pro Gly Thr Pro Leu Gly Pro Gly Gln Ser Lys Val Ile Gly Gly Ser
        35                  40                  45

Pro Gly Ala Gly Ser Gly Ala Gly Ala Gly Ser Gly Val Gly Val Pro
    50                  55                  60

Gly Val Gly Val Pro Gly Val Gly Val Pro Gly Val Gly Val Pro Gly
65                  70                  75                  80

Val Gly Val Pro Gly Val Gly Val Pro Gly Val Gly Val Pro Gly Val
                85                  90                  95

Gly Val Pro Gly Ala Gly Ala Gly Ser Gly Ala Gly Ala Gly Ser Gly
            100                 105                 110

Ala Gly Ala Gly Ser Gly Ala Gly Ala Gly Ser Gly Val Gly Val Pro
        115                 120                 125

Gly Val Gly Val Pro Gly Val Gly Val Pro Gly Val Gly Val Pro Gly
    130                 135                 140

Val Gly Val Pro Gly Val Gly Val Pro Gly Val Gly Val Pro Gly Val
145                 150                 155                 160

Gly Val Pro Gly Ala Gly Ala Gly Ser Gly Ala Gly Ala Gly Ser Gly
                165                 170                 175

Ala Gly Ala Gly Ser Gly Ala Gly Ala Gly Ser Gly Val Gly Val Pro
            180                 185                 190

Gly Val Gly Val Pro Gly Val Gly Val Pro Gly Val Gly Val Pro Gly
        195                 200                 205

Val Gly Val Pro Gly Val Gly Val Pro Gly Val Gly Val Pro Gly Val
    210                 215                 220

Gly Val Pro Gly Ala Gly Ala Gly Ser Gly Ala Gly Ala Gly Ser Gly
225                 230                 235                 240

Ala Gly Ala Met Asp Pro Gly Arg Tyr His Met Ala Ala Lys Gly Asp
                245                 250                 255

Arg Ala Pro Gly Thr Pro Leu Gly Pro Gly Gln Ser Lys Val Ile Gly
            260                 265                 270

Gly Ser Pro Asp Gln Asp Leu Arg Ser His His His His His His
        275                 280                 285

( 2 ) INFORMATION FOR SEQ ID NO:77:

( i ) SEQUENCE CHARACTERISTICS:
        ( A ) LENGTH: 486 amino acids
        ( B ) TYPE: amino acid
        ( C ) STRANDEDNESS: single (D) TOPOLOGY: linear (ii) MOLECULE TYPE: protein (xi) SEQUENCE DESCRIPTION: SEQ ID NO:77:

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
                20                  25                  30

Met Gly Ala Gly Ser Gly Ala Gly Ala Gly Ser Gly Val Gly Val Pro
                35                  40                  45

Gly Val Gly Val Pro Gly Val Gly Val Pro Gly Val Gly Val Pro Gly
        50                  55                  60

Leu Gly Pro Gly Gln Ser Lys Val Ile Gly Gly Val Pro Gly Val Gly
 65                  70                  75                  80

Val Pro Gly Val Gly Val Pro Gly Val Gly Val Pro Gly Ala Gly Ala
                85                  90                  95

Gly Ser Gly Ala Gly Ala Gly Ser Gly Ala Gly Ala Gly Ser Gly Ala
                100                 105                 110

Gly Ala Gly Ser Gly Val Gly Val Pro Gly Val Gly Val Pro Gly Val
                115                 120                 125

Gly Val Pro Gly Val Gly Val Pro Gly Gly Gly Leu Lys Gly Gly Gly
        130                 135                 140

Gly Val Pro Gly Val Gly Val Pro Gly Val Gly Val Pro Gly Val Gly
145                 150                 155                 160

Val Pro Gly Ala Gly Ala Gly Ser Gly Ala Gly Ala Gly Ser Gly Ala
                165                 170                 175

Gly Ala Gly Ser Gly Ala Gly Ala Gly Ser Gly Val Gly Val Pro Gly
                180                 185                 190

Val Gly Val Pro Gly Val Gly Val Pro Gly Val Gly Val Pro Gly Leu
        195                 200                 205

Gly Pro Gly Gln Ser Lys Val Ile Gly Gly Val Pro Gly Val Gly Val
        210                 215                 220

Pro Gly Val Gly Val Pro Gly Val Gly Val Pro Gly Ala Gly Ala Gly
225                 230                 235                 240

Ser Gly Ala Gly Ala Gly Ser Gly Ala Gly Ala Gly Ser Gly Ala Gly
                245                 250                 255

Ala Gly Ser Gly Val Gly Val Pro Gly Val Gly Val Pro Gly Val Gly
                260                 265                 270

Val Pro Gly Val Gly Val Pro Gly Gly Gly Leu Lys Gly Gly Gly Gly
        275                 280                 285

Val Pro Gly Val Gly Val Pro Gly Val Gly Val Pro Gly Val Gly Val
        290                 295                 300

Pro Gly Ala Gly Ala Gly Ser Gly Ala Gly Ala Gly Ser Gly Ala Gly
305                 310                 315                 320

Ala Gly Ser Gly Ala Gly Ala Gly Ser Gly Val Gly Val Pro Gly Val
                325                 330                 335

Gly Val Pro Gly Val Gly Val Pro Gly Val Gly Val Pro Gly Leu Gly
                340                 345                 350

Pro Gly Gln Ser Lys Val Ile Gly Gly Val Pro Gly Val Gly Val Pro
                355                 360                 365

Gly Val Gly Val Pro Gly Val Gly Val Pro Gly Ala Gly Ala Gly Ser
        370                 375                 380

Gly Ala Gly Ala Gly Ser Gly Ala Gly Ala Gly Ser Gly Ala Gly Ala
385                 390                 395                 400
```

|   |   |   |   |   |   |   |   |   |   |   |   |   |   |   |
|---|---|---|---|---|---|---|---|---|---|---|---|---|---|---|
| Gly | Ser | Gly | Val | Gly | Val | Pro | Gly | Val | Gly | Val | Pro | Gly | Val | Gly | Val |
|   |   |   |   | 405 |   |   |   | 410 |   |   |   |   | 415 |   |
| Pro | Gly | Val | Gly | Val | Pro | Gly | Gly | Gly | Leu | Lys | Gly | Gly | Gly | Gly | Val |
|   |   |   | 420 |   |   |   | 425 |   |   |   |   | 430 |   |   |
| Pro | Gly | Val | Gly | Val | Pro | Gly | Val | Gly | Val | Pro | Gly | Val | Gly | Val | Pro |
|   |   |   | 435 |   |   |   | 440 |   |   |   |   | 445 |   |   |
| Gly | Val | Gly | Val | Pro | Gly | Ala | Gly | Ala | Gly | Ser | Gly | Ala | Gly | Ala | Gly |
|   | 450 |   |   |   |   | 455 |   |   |   |   | 460 |   |   |   |
| Ser | Gly | Ala | Gly | Ala | Met | Asp | Pro | Gly | Arg | Tyr | Gln | Asp | Leu | Arg | Ser |
| 465 |   |   |   |   | 470 |   |   |   | 475 |   |   |   |   | 480 |
| His | His | His | His | His | His |
|   |   |   |   | 485 |   |

( 2 ) INFORMATION FOR SEQ ID NO:78:

( i ) SEQUENCE CHARACTERISTICS:
        ( A ) LENGTH: 479 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:78:

|   |   |   |   |   |   |   |   |   |   |   |   |   |   |   |   |
|---|---|---|---|---|---|---|---|---|---|---|---|---|---|---|---|
| Met | Asp | Pro | Val | Val | Leu | Gln | Arg | Arg | Asp | Trp | Glu | Asn | Pro | Gly | Val |
| 1 |   |   |   | 5 |   |   |   |   | 10 |   |   |   |   | 15 |   |
| Thr | Gln | Leu | Asn | Arg | Leu | Ala | Ala | His | Pro | Pro | Phe | Ala | Ser | Asp | Pro |
|   |   |   | 20 |   |   |   |   | 25 |   |   |   |   | 30 |   |   |
| Met | Gly | Ala | Gly | Ser | Gly | Ala | Gly | Ala | Gly | Ser | Gly | Val | Gly | Val | Pro |
|   |   |   | 35 |   |   |   |   | 40 |   |   |   |   | 45 |   |   |
| Gly | Val | Gly | Val | Pro | Gly | Val | Gly | Val | Pro | Gly | Val | Gly | Val | Pro | Gly |
|   | 50 |   |   |   |   | 55 |   |   |   |   | 60 |   |   |   |   |
| Leu | Gly | Pro | Gly | Gln | Ser | Lys | Val | Ile | Gly | Val | Pro | Gly | Val | Gly | Val |
| 65 |   |   |   |   | 70 |   |   |   |   | 75 |   |   |   |   | 80 |
| Val | Pro | Gly | Val | Gly | Val | Pro | Gly | Val | Gly | Val | Pro | Gly | Ala | Gly | Ala |
|   |   |   |   | 85 |   |   |   |   | 90 |   |   |   |   | 95 |   |
| Gly | Ser | Gly | Ala | Gly | Ala | Gly | Ser | Gly | Ala | Gly | Ala | Gly | Ser | Gly | Ala |
|   |   |   | 100 |   |   |   |   | 105 |   |   |   |   | 110 |   |   |
| Gly | Ala | Gly | Ser | Gly | Val | Gly | Val | Pro | Gly | Val | Gly | Val | Pro | Gly | Val |
|   |   |   | 115 |   |   |   |   | 120 |   |   |   |   | 125 |   |   |
| Gly | Val | Pro | Gly | Val | Gly | Val | Pro | Gly | Gly | Leu | Lys | Gly | Gly | Gly | Gly |
|   |   |   | 130 |   |   |   |   | 135 |   |   |   |   | 140 |   |   |
| Val | Pro | Gly | Val | Gly | Val | Pro | Gly | Val | Gly | Val | Pro | Gly | Val | Gly | Val |
| 145 |   |   |   |   | 150 |   |   |   |   | 155 |   |   |   |   | 160 |
| Pro | Gly | Ala | Gly | Ala | Gly | Ser | Gly | Ala | Gly | Ala | Gly | Ser | Gly | Ala | Gly |
|   |   |   |   | 165 |   |   |   |   | 170 |   |   |   |   | 175 |   |
| Ala | Gly | Ser | Gly | Ala | Gly | Ala | Gly | Ser | Gly | Val | Gly | Val | Pro | Gly | Val |
|   |   |   |   | 180 |   |   |   |   | 185 |   |   |   |   | 190 |   |
| Gly | Val | Pro | Gly | Val | Gly | Val | Pro | Gly | Val | Gly | Val | Pro | Gly | Leu | Gly |
|   |   |   | 195 |   |   |   |   | 200 |   |   |   |   | 205 |   |   |
| Pro | Gly | Gln | Ser | Lys | Val | Ile | Gly | Gly | Val | Pro | Gly | Val | Gly | Val | Pro |
|   |   |   | 210 |   |   |   |   | 215 |   |   |   |   | 220 |   |   |
| Gly | Val | Gly | Val | Pro | Gly | Val | Gly | Val | Pro | Gly | Ala | Gly | Ala | Gly | Ser |
| 225 |   |   |   |   | 230 |   |   |   |   | 235 |   |   |   |   | 240 |
| Gly | Ala | Gly | Ala | Gly | Ser | Gly | Ala | Gly | Ala | Gly | Ser | Gly | Ala | Gly | Ala |
|   |   |   |   | 245 |   |   |   |   | 250 |   |   |   |   | 255 |   |

Gly  Ser  Gly  Val  Gly  Val  Pro  Gly  Val  Gly  Val  Pro  Gly  Val  Gly  Val
                       260                      265                      270

Pro  Gly  Val  Gly  Val  Pro  Gly  Gly  Leu  Lys  Gly  Gly  Gly  Gly  Val  Pro
                       275                      280                      285

Gly  Val  Gly  Val  Pro  Gly  Val  Gly  Val  Pro  Gly  Val  Gly  Val  Pro  Gly
                  290                      295                      300

Ala  Gly  Ala  Gly  Ser  Gly  Ala  Gly  Ala  Gly  Ser  Gly  Ala  Gly  Ala  Gly
        305                           310                      315                      320

Ser  Gly  Ala  Gly  Ala  Gly  Ser  Gly  Val  Gly  Val  Pro  Gly  Val  Gly  Val
                            325                      330                      335

Pro  Gly  Val  Gly  Val  Pro  Gly  Val  Gly  Val  Pro  Gly  Leu  Gly  Pro  Gly
                       340                      345                      350

Gln  Ser  Lys  Val  Ile  Gly  Gly  Val  Pro  Gly  Val  Gly  Val  Pro  Gly  Val
                       355                      360                      365

Gly  Val  Pro  Gly  Val  Gly  Val  Pro  Gly  Ala  Gly  Ala  Gly  Ser  Gly  Ala
                  370                      375                      380

Gly  Ala  Gly  Ser  Gly  Ala  Gly  Ala  Gly  Ser  Gly  Ala  Gly  Ala  Gly  Ser
        385                           390                      395                      400

Gly  Val  Gly  Val  Pro  Gly  Val  Gly  Val  Pro  Gly  Val  Gly  Val  Pro  Gly
                            405                      410                      415

Val  Gly  Val  Pro  Gly  Gly  Gly  Leu  Lys  Gly  Gly  Gly  Gly  Val  Pro  Gly
                       420                      425                      430

Val  Gly  Val  Pro  Gly  Val  Gly  Val  Pro  Gly  Val  Gly  Val  Pro  Gly  Ala
                       435                      440                      445

Gly  Ala  Gly  Ser  Gly  Ala  Gly  Ala  Gly  Ser  Gly  Ala  Gly  Ala  Met  Asp
                  450                      455                      460

Pro  Gly  Arg  Tyr  Gln  Asp  Leu  Arg  Ser  His  His  His  His  His  His
        465                      470                      475

( 2 ) INFORMATION FOR SEQ ID NO:79:

( i ) SEQUENCE CHARACTERISTICS:
                ( A ) LENGTH: 8 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:79:

Gly  Gln  Gln  His  His  Leu  Gly  Gly
        1                      5

( 2 ) INFORMATION FOR SEQ ID NO:80:

( i ) SEQUENCE CHARACTERISTICS:
                ( A ) LENGTH: 15 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:80:

Ser  Val  Leu  Ser  Leu  Ser  Gln  Ser  Lys  Val  Leu  Pro  Val  Pro  Glu
        1                   5                        10                       15

( 2 ) INFORMATION FOR SEQ ID NO:81:

( i ) SEQUENCE CHARACTERISTICS:
                ( A ) LENGTH: 15 amino acids
                ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:81:

Ser Val Leu Ser Leu Ser Gln Ser Arg Val Leu Pro Val Pro Glu
1               5                   10                  15

(2) INFORMATION FOR SEQ ID NO:82:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:82:

Cys Val Leu Ser Leu Ser Gln Ser Arg Val Leu Val Pro Glu Cys
1               5                   10                  15

(2) INFORMATION FOR SEQ ID NO:83:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:83:

Ser Val Leu Ser Gly Ser Gln Ser Lys Val Leu Pro Val Pro Glu
1               5                   10                  15

(2) INFORMATION FOR SEQ ID NO:84:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:84:

Arg Arg Ser Lys His Ile Ser
1               5

(2) INFORMATION FOR SEQ ID NO:85:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:85:

Cys Leu Gly Pro Gly Gln Ser Lys Val Ile Gly Cys
1               5                   10

(2) INFORMATION FOR SEQ ID NO:86:

(i) SEQUENCE CHARACTERISTICS:
    (A) LENGTH: 6 amino acids
    (B) TYPE: amino acid (C) STRANDEDNESS: single
(D) TOPOLOGY: linear (ii) MOLECULE TYPE: peptide (xi) SEQUENCE DESCRIPTION: SEQ ID NO:86:

Ala Lys Lys Lys Arg Ser
1               5

(2) INFORMATION FOR SEQ ID NO:87:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:87:

Leu Ser Leu Ser Gln Ser Lys Val Leu Gly
1               5                   10

(2) INFORMATION FOR SEQ ID NO:88:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:88:

Ala His Lys Lys Gly Gln
1               5

(2) INFORMATION FOR SEQ ID NO:89:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:89:

Leu Gly Pro Gly Gln Ser Arg Val Ile Gly
1               5                   10

(2) INFORMATION FOR SEQ ID NO:90:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:90:

Tyr Leu Lys Asp Gln Gln
1               5

(2) INFORMATION FOR SEQ ID NO:91:

(i) SEQUENCE CHARACTERISTICS:
    (A) LENGTH: 10 amino acids
    (B) TYPE: amino acid (C) STRANDEDNESS: single
(D) TOPOLOGY: linear (ii) MOLECULE TYPE: peptide (xi) SEQUENCE DESCRIPTION: SEQ ID NO:91:

```
Leu  Gly  Pro  Gly  Gln  His  Lys  Val  Ile  Gly
1                   5                        10
```

(2) INFORMATION FOR SEQ ID NO:92:

(i) SEQUENCE CHARACTERISTICS:
   (A) LENGTH: 6 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:92:

```
Pro  Thr  Thr  Lys  Met  Ala
1                   5
```

(2) INFORMATION FOR SEQ ID NO:93:

(i) SEQUENCE CHARACTERISTICS:
   (A) LENGTH: 10 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:93:

```
Leu  Gly  Pro  Gly  Gln  His  Arg  Val  Ile  Gly
1                   5                        10
```

(2) INFORMATION FOR SEQ ID NO:94:

(i) SEQUENCE CHARACTERISTICS:
   (A) LENGTH: 6 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:94:

```
Arg  Leu  Asp  His  Lys  Phe
1                   5
```

(2) INFORMATION FOR SEQ ID NO:95:

(i) SEQUENCE CHARACTERISTICS:
   (A) LENGTH: 12 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:95:

```
Cys  Leu  Gly  Pro  Gly  Gln  Ser  Arg  Val  Ile  Gly  Cys
1                   5                             10
```

(2) INFORMATION FOR SEQ ID NO:96:

(i) SEQUENCE CHARACTERISTICS:
   (A) LENGTH: 7 amino acids
   (B) TYPE: amino acid (C) STRANDEDNESS: single
(D) TOPOLOGY: linear (i i) MOLECULE TYPE: peptide (x i) SEQUENCE DESCRIPTION: SEQ ID NO:96:

```
Val  Gly  Ser  Asn  Lys  Gly  Ala
1                 5
```

(2) INFORMATION FOR SEQ ID NO:97:

(i) SEQUENCE CHARACTERISTICS:
    (A) LENGTH: 11 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:97:

```
Gly  Gly  Pro  Gly  Gln  Ser  Lys  Val  Ile  Gly  Gly
1                 5                              10
```

(2) INFORMATION FOR SEQ ID NO:98:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:98:

```
Asn  Gln  Glu  Gln  Val  Ser  Pro  Leu  Thr
1                 5
```

(2) INFORMATION FOR SEQ ID NO:99:

(i) SEQUENCE CHARACTERISTICS:
    (A) LENGTH: 10 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:99:

```
Thr  Asp  Met  Pro  Gln  Met  Arg  Met  Gln  Leu
1                 5                         10
```

(2) INFORMATION FOR SEQ ID NO:100:

(i) SEQUENCE CHARACTERISTICS:
    (A) LENGTH: 8 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:100:

```
Cys  Gly  Gln  Ser  Lys  Val  Ile  Cys
1                 5
```

(2) INFORMATION FOR SEQ ID NO:101:

(i) SEQUENCE CHARACTERISTICS:
    (A) LENGTH: 12 amino acids
    (B) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:101:

Lys Val Leu Pro Ile Pro Gln Gln Val Val Pro Tyr
1               5                   10

( 2 ) INFORMATION FOR SEQ ID NO:102:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:102:

Arg Ala Val Pro Val Gln Ala Leu Leu
1               5

( 2 ) INFORMATION FOR SEQ ID NO:103:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:103:

Leu Asn Gln Glu Leu Leu
1               5

( 2 ) INFORMATION FOR SEQ ID NO:104:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:104:

Thr Val Gln Gln Glu Leu
1               5

( 2 ) INFORMATION FOR SEQ ID NO:105:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:105:

Val His His Gln Lys Leu Val
1               5

PRODUCTS COMPRISING SUBSTRATES CAPABLE OF ENZYMATIC CROSS-LINKING

CROSS-REFERENCE TO RELATED APPLICATIONS

This application is a continuation-in-part of application Ser. No. 08/205,518, filed Mar. 3, 1994, now abandoned.

INTRODUCTION

1. Technical Field

The field of this invention is polymeric materials having multiple sequences which are capable of covalent cross-linking by enzymatic reaction, particularly as implantable resorbable protein polymers.

2. Background

Enzymes are biological catalysts that accelerate chemical reactions. These chemical reactions fall into many classes. Of particular interest are enzymes whose substrates are proteins, where the enzyme catalyzes the covalent cross-linking of other compounds to the proteins. Striking characteristics of all enzymes are their catalytic power and specificity. Enzymes accelerate reactions by factors of at least a million. They are highly specific both in the reaction catalyzed and in their choice of reactants, called substrates. Enzyme catalysis allows reactions to occur under physiological conditions.

There are numerous examples of enzymes which have been modified to allow them to operate under more extreme conditions, such as low pH or high temperature, to develop more useful products. There are enzymes which have been modified and shown to have different activities, including their substrate specificity. A wide variety of conditions have been shown to modify the catalytic activity of enzymes, such as the use of non-polar solvents. However, there have been relatively few attempts to produce substrates not found in nature for enzymes where the substrate will be covalently coupled to another compound, providing for products of substantial utility. In particular, the use of non-natural substrates containing multiple sites for enzymatic cross-linking in order to modify selected properties of natural substrate/enzyme reaction products is not believed to have been previously demonstrated. Nevertheless, for particular product applications there are deficiencies in the performance of natural substrate/enzyme systems which make it desirable to produce such substrates.

Peptide synthetases, acyl transferases, glycosyl transferases, phosphotransferases have varying degrees of specificity as to their ability to form covalent bonds between two molecules. To the extent that the enzyme is not too fastidious in its substrate, polyfunctional molecules may be employed which cross-link to form structurally strong products, which may serve to bond or cement various parts or constituents of a body or organism. Thus, by having a polyfunctional polymer with cross-linking elements, where the polymer is adherent to the parts or constituents, by cross-linking the polymer, the parts or constituents may be bonded together.

A compelling example is in the production of an adhesive to bond separated tissues. Sutures and staples are effective and well established wound closure devices. However, there are surgical procedures where classical repair procedures are unsatisfactory, limited to highly trained specialists (e.g. microsurgery), or not applicable due to tissue or organ fragility, inaccessibility (e.g. endoscopy procedures), or fluid loss, including capillary "weeping". Tissue adhesives and sealants have been developed to meet these needs. They may be used to seal or reinforce wounds that have been sutured or stapled, as well as finding independent use. The leading commercial products are fibrin glues and cyanoacrylates. However, both products have significant limitations which have prevented their widespread use.

Cyanoacrylates are mainly used for cutaneous wound closure in facial and reconstructive surgery. The appeal of cyanoacrylates is its speed of bonding, which is almost immediate, and its great bond strength. However, its speed of bonding can be a disadvantage, since glued tissue must be cut again in order to reshape it to approximate its original conformation. Additionally, it can only be used on dry substrates since its mode of action is through a mechanical interlock and it is relatively inflexible compared to surrounding tissue. Cyanoacrylates are also known to be toxic to some tissues and although it is not considered to be biodegradable, potential degradation products are suspected to be carcinogenic.

Fibrin glues comprising blood-derived fibrinogen and thrombin function primarily as a sealant and hemostat and have been used in many different surgical procedures within the body. They have been shown to be non-toxic, biocompatible and biodegradable. They are able to control excessive bleeding and decrease fibrosis. However, tissues bonded with fibrin cannot be subjected to even moderate tensile stress without rupturing the bond. It takes 3–10 minutes for an initial bond to develop, but requires 30 minutes to several hours for full strength to develop. Depending upon the application, the product may also resorb too quickly. Fibrin glues derived from heterologous human and animal sera may provoke undesirable immune responses, and expose the patient to the potential risk of viral infection. Autologous fibrin glues may be impractical to obtain and use and may compromise patient safety.

There is, therefore, substantial interest in developing products which have the biocompatibility of fibrin glues but which set more quickly and have enhanced strength. A product having such attributes which is also not derived from blood or animal sources is also of interest.

Relevant Literature

Enzymes and their function are described in Enzymes, 3rd Edition, Dixon, M. and Webb, E. C., eds., Academic Press, NY 1979; and The Enzymes, 3rd edition, Boyer, P. D., Academic Press, NY 1970—. Tissue adhesives are described in Tissue Adhesives in Surgery, Matsumoto, T., Medical Examination Publishing Co., Inc., 1972 and Sierra, D. H., J. Biomat. App. 7:309–352, 1993. Methods of preparation of protein polymers having blocks of repetitive units are described in U.S. Pat. No. 5,243,038 and EPA 89.913054.3.

SUMMARY OF THE INVENTION

Polymeric compositions and methods for their use are provided, where the polymeric compositions are capable of enzyme catalyzed reaction involving covalent, normally peptide bond, cross-linking. Polyfunctional polymers are employed, where the polymers or the polymer(s) in conjuction with low molecular weight polyfunctional cross-linking agents, are combined with an enzyme to provide for cross-linking with increase in tensile properties. The compositions find particular application for use in biological systems, where in situ formation of a biocompatible material having structural integrity is desired. For applications within the body, the materials may be subject to resorption over a predetermined time period, particularly by modifying their susceptibility to the action of specific proteases. Preferred compositions comprise a plurality of amino acid sequences which are capable of transamidase reaction, such as catalyzed by factor XIIIa, to form an isopeptide bond, where the sequence is a side chain of a polymeric backbone or is part of the backbone. The compositions find use as medical adhesives and sealants, in the closure of wounds and repair of damaged tissues, prosthesis coatings, drug depots, matrices for the transplantation of cells and the like.

Alternatively, the compositions may be used as substrates for enzyme catalyzed reaction to bind various agents to a site comprising the subject inventions, or the like.

DESCRIPTION OF THE SPECIFIC EMBODIMENTS

Compositions and their uses are provided, where the compositions are comprised of high molecular weight polymeric compositions comprising a plurality of sequences serving as substrates for enzymatic cross-linking. By employing enzymes such as transferases and synthetases, which can act on polyfunctional substrates, so as to form covalent bonds at recognition sites, a cross-linked structure can be produced, having enhanced tensile properties. The recognition sites may comprise naturally occurring or mutated consensus sequences or in some instances a single reactive amino acid or functional group. By employing polymers having good adhesive properties, particularly after cross-linking, the resulting cross-linked product finds use in bonding parts together, such as body parts or parts of an organism.

Synthetic proteins may be prepared which have amino acids which are susceptible to enzyme catalyzed cross-linking. By appropriate selection of enzyme recognition sites, the synthetic protein may be cross-linked by itself or in conjuction with small polyfunctional molecules or polymers. Illustrative of such polymers are polymers comprising recognition sites which can result in peptide cross-links, particularly as substrates for transglutaminases, such as plasma factor XIIIa, or modified forms of these natural enzymes. The sequences may be the naturally occurring sequences or modified sequences, particularly where the glutamine or lysine involved with isopeptide bond formation or amino acids surrounding them are substituted by different amino acids in order to modulate the enzyme catalyzed reaction of the lysine or glutamine.

Alternatively, synthetic peptides conferring the activities described above may be covalently conjugated to high molecular weight carriers in order to promote the intermolecular cross-linking of the carrier molecules. An adhesive product composed of such peptide conjugated carriers will attain its setting speed and bonding strength on the basis of the cross-linking chemistry and the adhesive properties supplied by the peptide sequences, as well as the intrinsic properties of the polymer. However, additional beneficial properties may also be provided by the carrier molecules such as additional reactivity, solubility, viscoelasticity, adhesivity, biocompatibility, bioresorption, and biofunctionality. Examples of carrier molecules which may be used are proteins such as collagen, fibrinogen, casein, keratin, and their derivatives; polysaccharides such as hyaluronic acid, chitosan, heparin, glycosaminoglycans, dextran, cellulose and their derivatives; and synthetic polymers such as polyethylene glycol, polyvinyl alcohol, polyesters, polyacrylates, and their derivatives. Depending on the purpose of the product and the context in which it is used, the composition may be physiologically compatible or not. The primary application will be in conjunction with physiological uses.

Enzymes of interest are those that have an amino acid as one of their substrates. The enzymes may react with a particular amino acid, where there is no specific requirement for flanking amino acid sequences or they may require that the reactive amino acid be positioned within a particular amino acid sequence. The other substrate for the enzymes can fall into a variety of different classes, including: an amino acid, individually or as part of a peptide or protein; specific chemical groups such as phosphates and sulphates, whether as part of a larger molecule or not; monosaccharides, disaccharides, and polysaccharides; and lipids and fatty acids. The common element defining the reaction which occurs between the substrates is that a covalent bond is established, forming a larger molecule than either of the individual substrates, normally involving the formation of amides, esters, ethers and alkylation of amines. Therefore, the cross-linking will normally be other than the formation of a disulfide bond between two cysteines and will usually involve a carbon atom, particularly an oxo or oxy group, more particularly, a carboxy group, where esters and amides are formed. As indicated above, in some instances with inorganic acid groups, other than carboxy ester or amide formation may be involved, inorganic esters, amides or anhydrides being formed.

Examples of such enzymes include: lysyl oxidase, which initiates the formation of a covalent bond between lysine residues on adjacent protein molecules, used in the cross-linking of elastin and also collagen, where one of the lysines is oxidized to act as an aldehyde group for formation of an imine; phosphorylases, such as cellular phosphorylase A or B, which couple phosphate and serine; glycosylases, which typically couple mono- or disaccharides to proteins through the amino acids serine or asparagine, and the enzymes which are responsible for the coupling of polysaccharides and proteins in the formation of glycosaminoglycans; fatty acyltransferases, which are involved in the coupling of lipids and fatty acids onto proteins; and transamidases, particularly transglutaminases, which couple amino acids through the formation of an isopeptide bond, particularly the amino acids glutamine and lysine.

As is common among the different categories of enzymes, there may be many different enzymes which catalyze the same basic chemical reaction but which have different catalytic rates or substrate specificities. For example, among the transglutaminases, there are liver, muscle, epithelial (or "tissue"), and keratinocyte transglutaminases, which among them include different specificities for the amino acids flanking the glutamine residue. All use lysine as the complementary substrate.

Factor XIIIa is a transglutaminase which forms a covalent isopeptide linkage between an available lysine and a specific glutamine within a defined peptide consensus sequence of the fibrin gamma chain, where individual fibrin chains are held together as a complex with other subunits of fibrinogen. This provides a mechanism for covalent attachment between fibrin chains and from fibrin chains to extracellular matrix proteins (e.g. collagen, fibronectin) and is the chemistry underlying current fibrin-based glues. There are two distinct factor XIIIa species, one derived from plasma and one derived from placenta, both having equivalent activity for fibrin. Human fibrin has two identical sites which are covalently cross-linked by activated factor XIII (factor XIIIa) to form an adhesive fibrin matrix. Fibrin glue was used as a model for demonstrating that substrates containing multiple sites for enzymatic cross-linking can modify selected properties of natural substrate/enzyme reaction products.

As exemplary of the use of physiologically acceptable polymers is the use of peptide sequences which serve as recognition sites for isopeptide formation. These subject polymeric compounds may comprise a plurality of naturally occurring complete or minimal consensus sequences and/or mutated sequences for enzyme catalyzed isopeptide formation. The subject polymeric compositions may be divided into a number of categories: (1) the isopeptide substrate sequence, e.g. factor XIIIa ("FXIIIa") substrate sequence, is part of a synthetic protein sequence having at least two isopeptide substrate sequences in the chain of the polymer, where the isopeptide substrate sequence is (a) the natural substrate sequence of an enzyme; or (b) a mutated sequence; or (2) the isopeptide substrate sequence is a side chain of a polymer, where the isopeptide substrate sequence is (a) the natural substrate sequence; or (b) a mutated sequence.

Of particular interest are synthetic peptides that can serve as factor XIIIa substrates, where the peptides or conjugation products of high molecular weight polymers containing reactive amino groups and pendent factor XIIIa substrate moieties can be covalently cross-linked via the action of activated factor XIII, a ubiquitous, plasma clotting enzyme. Conjugates can be produced via a multitude of acceptable peptide conjugation chemistries as long as the chemistry maintains an accessible and reactive glutamine and/or lysine residue in the peptide. The active amino group can be supplied on the same peptide (via a lysine residue or any aliphatic amine that may serve as a lysine substitute) allowing a single conjugated species to form the cross-linked adhesive matrix or on a separate peptide or compound allowing for a mixture of the two molecules to provide adhesive cross-linking. The mixture of two compounds allows the control and adjustment of the concentrations of each species which may be advantageous in optimization of adhesive properties.

For the desired degree of cross-linking, there will be a spacer or intervening sequence of at least about 25 amino acids, or their atom equivalent with non-peptidic polymers, between the same reactive amino acids, usually between reactive amino acids. By way of illustration in referring to the same amino acids, this would intend glutamine capable of enzyme catalyzed cross-linking, while in referring to reactive amino acids, this would intend both glutamine and lysine capable of enzyme catalyzed cross-linking. This spacer will be present where the reactive amino acid is part of the polymeric chain or is part of a pendent sequence. Desirably there will be at least about 30 amino acids between the same reactive amino acids, more preferably at least about 40 amino acids. The intervening amino acids will include amino acids as part of the consensus sequence, as appropriate, and other amino acids which may play a variety of roles.

The polymers will be at least 15 kD, generally at least about 35 kD, more usually at least about 50 kD and generally not above 250 kD, usually not above about 125 kD in molecular weight.

The protein polymer may be a sequence which has as its only repetitive motif the consensus sequence or may have repetitive domains, which comprise the reactive amino acid and an intervening sequence. For the most part, the protein polymer will have repetitive blocks, where the blocks may be the same or different, there usually being not more than about 3 different blocks. The blocks will be at least about 10 amino acids, usually at least 20 amino acids, more usually at least about 40 amino acids, preferably at least about 50 amino acids, and may be at least about 65 amino acids or more, usually not more than about 200 amino acids.

The amino acids between the reactive amino acids may play a passive role in providing for the molecular weight of the protein, without introducing undesirable properties, or may play an active role, in providing for particular structural properties, e.g. tensile properties, conformation, hydrophilic/ hydrophobic regions, adhesion properties, specific binding properties, e.g. cell binding or basement membrane binding properties, or the like, depending upon the intended use of the protein. As undesirable properties could be immunogenicity, proteolytic susceptibility, inflammatory activity, etc., when used in vivo, insolubility when used in vitro, and the like.

The intervening sequence may include a wide variety of functional peptide sequences, such as the fibronectin binding site (RGD), the laminin binding site, the fibrin gamma polsite, lipid or saccharide binding recognition sites, protease cleavage recognition sites, adhesion molecule recognition sites, e.g. lectin sites, and the like. serving as intervening sequences may be all or a portion of the protein sequence in which the reactive amino acid is found, combinations of such sequence with other sequences which provide particular properties, relatively random sequences, which may provide generally hydrophobic and/or hydrophilic properties, repetitive sequences of from about 3 to 30 amino acids, particularly naturally occurring sequences of from about 3 to 18 amino acids, where the repetition may be based on a motif, such as in collagen, rather than on the identical sequence being repeated, or combinations thereof.

Of particular interest as the intervening sequence is a portion of the protein in which the reactive amino acid consensus sequence is found, more particularly the sequence proximal to the consensus sequence, the N-sequence, the C-sequence or both. For example in the case of isopeptide formation using Factor XIII, a sequence from fibrinogen, preferably from the fibrin sequence, or a sequence from casein, particularly the sequence proximal to the consensus sequence, may be employed. Thus, one would have the naturally occurring sequence or fragment thereof repeated as a block polymer. Where one uses the naturally occurring sequence or mutated sequence thereof, there will usually be at least 10 amino acids from the natural protein, more usually at least about 15 amino acids, and usually not more than about 125 amino acids, more usually not more than about 100 amino acids. The number of mutations will usually be fewer than 20 number %, more usually fewer than 10 number %, and conveniently fewer than 5 number %, generally being in the range of about 0 to 10 mutations, where the mutations may be deletions, insertions, transversions and transitions. One may have, as already indicated above, other sequences to provide other functions to the protein polymer, where the sequences may be tandem or internal to the natural sequence.

Alternatively, the protein polymer may involve a repetitive sequence comprising relatively small units of from 3 to about 30 amino acids, particularly derived from a naturally occurring sequence. With reactive amino acid containing sequences or block copolymers, the repetitive units will generally be present in from about 2 to 30, usually 2 to 15, more usually 2 to 12, tandem units, depending on the number of amino acids in each unit, the desired length of the repetitive unit intervening sequence, the desired properties of the protein polymer, and the like.

The protein polymer comprised of repetitive units will have a repetitive unit of from about 2 to 200, often from about 2 to 100, more often from about 3 to 30, usually 3 to 15 amino acids, more usually 3 to 12 amino acids, and particularly 3 to 8 amino acids, where the repetitive unit will normally be related to a naturally occurring repetitive unit. Naturally occurring proteins which have repetitive units as the main component of their structure, where the repetitive unit may differ as to some of the amino acids, but will have a motif which results in a particular structure or conformation, include collagen, where the motif requires every third amino acid to be glycine and that there be a relatively high proportion of proline at the remaining two sites, generally between about 10 to 45% of the total amino acids present; elastin (VPGVG) (SEQ ID NO:01); fibroin (GAGAGS)(SEQ ID NO:02); keratin (KLK/ELAEA)(SEQ ID NO:03); or the like. Depending on the application, the polymer is desirably biocompatible, particularly resorbable.

The repetitive units may be homopolymer units, alternating repetitive units, or block copolymer units, where a block has at least two repetitive units, or combinations thereof. If desired, different repetitive units may be present between the different recognition sites along the protein chain. Usually the intervening repetitive units will involve at least 2 repetitive units, frequently at least 3 repetitive units and may be 60 or more repetitive units, where the average number of repetitive units will usually be at least about 2, more usually at least about 3 repetitive units, often at least about 5 repetitive units, and not more than about 60, more usually not more than about 30 repetitive units. By varying the selection of repetitive units, the size of the blocks, and the frequency and spacing of the consensus sequences, the physical, chemical and biological properties can be greatly varied.

The protein polymer may have varying sequences for serving particular functions, such as separation, purification, chelation and the like. For example, one can have a string of at least 4 histidines, usually not more than about 12 histidines, which will serve to chelate metal ions to allow for separation and purification, as well as ease of identification.

Instead of having a protein polymer with the reactive amino acid in the polymer chain, one may link an oligopeptide comprising the reactive amino acid to a polymeric backbone. A high molecular weight carrier molecule of particular use is collagen; especially soluble atelopeptide collagen. Active peptides may be conjugated under conditions in which at least two reactive glutamine containing peptides are conjugated per collagen molecule. More preferably, 4 or more peptides may be conjugated to a single collagen molecule. The more cross-links forming to create the final adhesive, the greater the cohesive strength of the adhesive. The greater the concentration of potential cross-link sites, the more rapid the adhesive will set. Either property will yield a product of improved utility. Unconjugated or partially conjugated collagen provides ample lysine residues to serve as reactive amines. Therefore, a mixture of fully or partially conjugated peptide collagen and unconjugated collagen could serve as a useful adhesive substrate for factor XIIIa. Native collagen by itself is a poor substrate for factor XIIIa because it has no reactive glutamines. However, body tissues containing collagen and other proteins contain many lysines which may participate indiscriminately for cross-linking with the conjugate. Production of an adhesive mixture which has a stoichiometric excess of glutamine cross-linking sites over reactive amino groups will promote the cross-linking of the conjugate with the body tissue to which it is applied. This will promote a stronger adhesive bond.

One limitation with the use of collagen or other native proteins for conjugation with active peptides is that they are potentially animal derived and their properties may not suit the formulation needs of the product. For example, the solubility of atelocollagen is approximately 25 mg/ml in aqueous solution. If it becomes denatured during processing or formulation, its solubility falls to 15 mg/ml. Above these concentrations, collagen solutions are highly viscous suspensions or gels that are extremely difficult to mix and will prevent the diffusion of crosslinking agents such as factor XIII. These limitations make native collagen impractical for use if the adhesive performance requires that the protein substrate concentration exceed 25 mg/ml. It is easy to presume that a protein concentration in excess of 25 mg/ml might be required considering that the protein substrate concentration of fibrin glue can be as high as 110 mg/ml (Immuno AG, Tisseel® product specification).

These limitations can be overcome by the use of synthetically designed and recombinantly produced protein polymers for conjugation. Of particular use are those protein polymers as described above which are high in molecular weight, contain amino acids whose side chains lend themselves to convenient and controlled chemical modification such as lysine, cysteine, and glutamic acid, and are soluble in aqueous solution at concentrations of 50 mg/ml or greater.

The subject compositions may comprise one or more compounds, determined in part by whether a single compound can provide both the carboxy donor and amino donor entities, e.g. amino acids. Depending on the enzyme, the recognition sequence may be severely restricted or allow for various degrees of substitution, without significantly adversely affecting the binding affinity of the substrate sequence to the enzyme and the rate of the enzyme catalyzed reaction. The composition will include at least one polymeric compound of at least 15 kD comprising at least two recognition sequences providing the same reactive functionality, with the reactive amino acid in the polymer chain or as a side group or the combination thereof. Where only one compound is present, the compound will have a plurality of recognition sequences which provide the carboxy and amino reactive amino acids. Where there is more than one compound, the same or different compounds may provide one or the other of the reactive amino acids. Conveniently, there will be one or two polymeric compounds, associated with one or two small molecules which have at least two reactive amino acids, to serve as cross-linkers of the polymeric compound(s). The small cross-linking molecules will usually be at least about 150 D, usually at least about 200 D and not more than about 10 kD, usually not more than about 5 kD in molecular weight.

The isopeptide substrate sequence may be any recognition site, comprising one or a plurality of amino acids, e.g. a single amino acid or an amino acid sequence of 3 or more amino acids, recognized by an enzyme which recognizes the recognition site in producing an isopeptide bond between an amino group and a carboxy group. For the most part, the reaction will involve at least one naturally occurring or mutated consensus sequence, particularly involving the carboxy donor amino acid. Therefore, for the most part, the reaction will involve a carboxy donor amino acid, e.g. the carboxamide of glutamine, in a consensus sequence and another molecule having an amino group, particularly an amino acid, which may be a diamine or polyamino compound having from about 2 to 5 amino groups, conveniently an oligopeptide, or part of a polypeptide or protein. Both naturally occurring or mutated sequences may be employed, which are active in the formation of the isopeptide bond. The naturally occurring sequence may be from any convenient source, which is recognized by the enzyme which catalyzes the formation of the isopeptide bond. Depending on the use of the subject composition, where the composition is to be used in the treatment of a mammalian host, particularly a human host, the sequence will normally be biocompatible, so as to avoid a strong immune response or the need for immunosuppression.

The consensus sequence may be derived from fibrinogen, fibronectin, myosin, the microtubule-associated protein "tau", whether primate or other mammalian species, particularly human, casein, or from any other protein, where the protein has a consensus sequence, which is a substrate for an available enzyme for the isopeptide bond formation, which consensus sequence and enzyme can be used in the applications for the subject compositions. Human fibrin has the sequence (residues 421–437) (GEGQQHHLGGAKQAGDV) (SEQ ID NO: 04); bovine casein has the sequence (residues 162–175) (VLSLSQSKVLPVPE)(SEQ ID NO:05); other sequences may also find use.

The mutated sequences may be truncated sequences, particularly for removal of one of the amino acids involved with the isopeptide formation. It is found that FXIIIa enzyme is relatively specific as to the amino acids contiguous to the glutamine, but not the lysine. Therefore, as to the glutamine donor, the contiguous amino acids will be, for the most part, the naturally occurring amino acids, there usually being at least 5 amino acids of the consensus sequence, usually at least 2 on each side of the glutamine. As for the lysine, the contiguous amino acids may be modified and the consensus sequence truncated, while still retaining activity. Usually the sequences for the glutamine will have at least 6, more usually 8 amino acids, and may be as many as 60 amino acids, usually not more than about 45 amino acids, more usually not more than about 36 amino acids. The number of amino acids in the enzyme recognition site sequence depends upon the nature of the repetitive sequence, the length of the repetitive sequence, the source of the consensus sequence, whether the naturally occurring sequence or the mutated sequence, the inclusion of additional amino acid sequences providing for additional functionalities, and the like. For lysine, there need be none of the consensus amino acids, there usually being a total of at least 3 contiguous amino acids of the consensus sequence, including the lysine. Instead of lysine, amino groups may be provided, particularly where the amino group is bonded to a methylene group, more particularly to a polymethylene of at least two methylene groups.

The small molecules which find use will have at least two reactive sequences to serve as cross-linking agents for the polymer. The small molecules may be aliphatic, alicyclic, aromatic, heterocyclic or combinations thereof, usually at least partially aliphatic. The small molecules may be non-oligomeric or oligomeric, e.g. oligopeptides. The molecules may be hydrophilic or hydrophobic. The small molecules may provide the carboxamide group, the amino group or both, usually the amino group.

The small molecules used in conjuction with the polymeric molecule(s) provide for a number of opportunities not available using solely polymeric molecules. In this way, cross-linking may be controlled, where the polymer only has one of the amino acids involved with the isopeptide link, and the cross-linking agent becomes exhausted or may be removed from the polymer. By using the small cross-linking agent, the degree of cross-linking can be better controlled and the polymer may have a large number of recognition sites. Also, depending upon the nature of the recognition site, e.g. Q or K, the small molecules may serve as cross-linking agents to adjacent compositions, such as tissue or other substrate.

Various polymeric compounds may be employed to produce the cross-linked product. As already indicated, the recognition site(s) may be part of the polymeric backbone or a side chain to a polymeric backbone. Where the recognition site is part of the polymeric backbone, the polymer will usually be a protein, although an oligopeptide block may be co-polymerized, usually with a polymer other than a protein polymer using chemical linkage. However, where the recognition site is a side chain, the polymer may be a protein or other physiologically and enzymatically compatible polymer.

The subject polymers may include polymers having recognition sites for enzyme catalyzing reactions proximal to the termini, with an intervening sequence, particularly an intervening sequence of repetitive units as described above. However, for the most part the subject polymers comprising recognition sites for enzyme catalyzed reactions resulting in new covalent bonds and cross-linking may be generally depicted by the following formula:

$$\psi-(\{\Phi-\Omega\}^p \text{ or } \{\Omega-\Phi\}^p \text{ or } \Sigma)_n-\psi_1$$

wherein:

$\psi$ and $\psi_1$ may or may not be present, if present, are the same or different and are of not more than about a total of 125 amino acids, usually not more than a total of about 70 amino acids, and usually differing from the intervening sequences of the polymer, but may include one or more recognition sites, generally being not more than about 10 number % of the amino acids of the polymer, usually not more than about 5 number % of the amino acids of the polymer;

$\Phi$ represents the intervening sequences or spacers of the protein polymer, where the intevening sequence may be free of any repetitive motif or may comprise repetitive units, usually comprising at least two repetitive units and usually not more than about 60 repetitive units, generally comprising from about 3 to 30 repetitive units, where the repetitive units may be the same, alternating different repetitive units of 2 or more, usually 2, and blocks of different repetitive units;

$\Sigma$ intends $\{(\Omega-\Phi)^{p'}\}_n\Omega$, p is an integer of from 2 to about 10, indicating that there are that number of domains of the intervening sequence and the reactive amino acid containing sequence, where each of the domains may be the same or different, there usually being not more than about 6 different domains, more usually not more than about 3 different domains, frequently there being from 1 to 2 different domains;

p' is an integer of from 1 to about 9, otherwise coming within the definition of p;

$\Omega$ is a functional amino acid sequence, which may be the same or different, usually the same, each time $\Omega$ is repeated; at least 2$\Omega$ include the reactive amino acid, normally in an enzyme recognition site, as appropriate for the particular enzyme, and may involve hydroxy, carboxy (includes the acid, ester and amide), amino, phospho, or other functionality for forming a covalent bond, individually or in combination; for isopeptide formation, the amino acid sequence may comprise one or both, carboxy and primary amino, which may be a consensus sequence or a mutated sequence, which may have one or both of the active Q and K; for Q, generally being at least 5 amino acids and not more than about 60 amino acids, usually not more than about 30 amino acids, where one or more reactive sequences may be present; for K, only lysine need be present, preferably there being at least 3 contiguous amino acids of the consensus sequence;

other functional sequences include GGAKQAGDV (SEQ ID NO:06), and the like, the sequences generally being at least 3 and not more than about 60 amino acids, frequently not more than about 45 amino acids; instead of or in addition to having a reactive amino acid, Ω may have a functional amino acid or sequence involved with other properties of interest, such as proteolytic cleavage sites, cell binding sites, adhesion sites, etc.; and n will vary with p and the number of amino acids in Ω-Φ, where n is at least 1, and n×p is usually at least 2, and not more than about 75, usually not more than about 60.

One group of block copolymers of the subject invention will, for the most part, comprise, individually or in combination, silk-like sequences, particularly GAGAGS (SEQ ID NO:07), and elastin-like sequences, particularly VPGVG (SEQ ID NO:08), where the repeating units will be in blocks of at least 2 repeating units, more usually at least about 4 repeating units, and generally not more than about 32 repeating units, more usually not more than about 24 repeating units. Usually, the number of repeating units in the block of the silk repeating unit will not be more than about 2 times the number of repeating units in the block of the elastin repeating unit, usually not more than about 1 time the number of repeating units, and will generally be at least about 0.1 time the number of repeating units of elastin in the elastin block. For the most part, the elastin block will have at least 4 repeating units, more usually at least about 8 repeating units, and up to about 32 repeating units, more usually up to about 24 repeating units. By contrast, the silk block will have at least about 2 repeating units and not more than about 4 repeating units, usually not more than about 16 repeating units, and preferably not more than about 8 repeating units.

Preferred compositions will have from about 10 to 60 percent of silk repeating units, more usually from about 20 to 55 percent of silk repeating units, where the ratio of elastin repeating units to silk repeating units per block will generally be in the range of from about 4:1 to 1:1.

One repetitive unit homopolymer employs the collagen motif, where each repeating unit block has from 2 to about 10 different triads, usually from about 2 to about 6 different triads, in the repeating unit block, between functional sequences. The number of triads will generally be at least about 3 and not more than about 36, usually at least about 5 and not more than about 25 triad repeating units. The number of prolines will be below about 45 number % of the amino acids in the repeating unit block, generally having on the average not more than about 1.2, usually not more than about 1, proline per triad.

By varying the length of each block, in the case of block copolymers, the ratio of amino acids of one block in relation to the amino acids of the other block, the choice of the repetitive units, the number of functional sequences and their location, e.g. terminal or internal, whether there can be internal cross-linking or only intermolecular cross-linking, the properties of the products may be greatly varied. For example, resorption rates can be greatly varied, where in an elastin/fibroin block copolymer, resorption will be enhanced with higher proportions of the elastin repeat unit. The ability to promote hemostasis or cell attachment and migration can be varied. Also, various physical properties, such as solubility, adsorption to tissues, tensile strength, cohesive strength, elongation, and set times, can be substantially retained or varied, so as to provide the necessary physical properties for the intended application.

In the case of the presence of small repetitive units, particularly of from about 3 to 18 amino acids, the proportion of the total amino acids contributed by any one repeating block or domain to the total number of amino acids may vary widely, from a range of about 5 number % to about 95 number %, usually ranging from about 15 number % to about 80 number %, more usually not less than about 20 number % and up to about 75 number %.

As already indicated, instead of using polymers where the enzyme recognition site sequence, which includes by definition the reactive amino acid by itself or in conjunction with other amino acids, is in the chain of the polymer, the enzyme recognition site sequence may be a side chain. A wide variety of polymers may be used as the backbone for the enzyme recognition site or reactive side chains. The choice of polymer will vary in accordance with the intended application and may be naturally occurring, synthetic or combinations thereof. Such polymers include, but are not limited to, synthetic polymers, both addition and condensation polymers, such as polylactides, polyglycolides, polyanhydrides, polyorthoesters, polyvinyl compounds, polyolefins, polyacrylates, polyethylene glycol, polyesters, polyvinyl alcohol, polyethers, copolymers thereof, and naturally occurring polymers, such as collagen, atelopeptide collagen, fibrinogen, keratin, casein, chitosan, heparin, dextran, cellulose, glycosaminoglycans, hyaluronic acid, and the like.

The reactive side chains which are attached may be varied widely, depending on the nature of the functionality required for enzyme catalyzed reaction and the requirements for recognition by the enzyme for reaction. In the case of isopeptide formation, for example, it will depend on whether the side chain comprises a reactive glutamine and lysine, or one or the other. So far as the lysine is concerned, when synthesizing the side chain, the lysine may be substituted with a polymethylene primary amine, usually having at least three methylene groups, where the reactive portion is bonded to a group which can be linked to the polymer backbone. The glutamine comprising reactive sequence will usually comprise at least about 8 amino acids to be efficiently recognized by FXIIIa, while the lysine reactive group may contain no amino acids or may contain 1 or more amino acids, conveniently comprising at least 6 amino acids, where the natural sequence is employed.

Of particular interest are polymers having short repeat units comprising a reactive linking amino acid, particularly carboxy, amino, and thiol functionality, such as D, E, K, R, and C. Particularly, the unit will be of from 3 to 10, usually 3 to 6 amino acids, where 1 or more amino acids will be glycine or alanine, usually fewer than 100% of the amino acids other than the reactive amino acid, generally being from about 20 to 75% of the total number of amino acids. Conveniently, one may replace one of the amino acids of a repeating unit with the reactive amino acid, so that the structure of the polymer is not significantly modified.

The number of side chains will be at least about 2, usually at least 4, and generally not more than about 30, usually not more than about 20. Since as the polymer becomes cross-linked, the accessibility of the side chains to the enzyme becomes diminished, so that increasing the number of side chains beyond a certain minimum will not provide any advantages as to setup time and strength.

Depending on the functionality of the reactive linking amino acid, various cross-linking compounds may be used. In the cross-linking compound, active olefins may be used with either amino or carboxy groups, while thiol groups may be used with amino or carboxy groups. Amino groups on the polymer may be functionalized with maleic anhydride to provide for an active olefin on the polymer. Usually, the two functionalities on the linking compound will be different and the spacer between the two functionalities will usually be aliphatic or carbocyclic aromatic. The spacer will usually be fewer than 36 carbon atoms, usually fewer than 20 carbon atoms, generally being other than a bond, usually being at least one carbon atom. Alternatively, the pendent sequence may be directly bonded to a functionality on the backbone polymer, where the functionality on the pendent group and the backbone polymer are compatible for bonding.

Generally, the side chain will be at least about 3 amino acids long, usually at least about 5 amino acids long and generally from about 5 to 16 amino acids long, usually not more than about 12 amino acids long. As indicated previously, with lysine and transglutaminases, an amino functionality can suffice. Usually, there will be at least one glycine or alanine, and up to 50% or more of the amino acids other than the active amino acid may be glycine, depending on the consensus sequence required for activity. For transglutaminases, the consensus sequence comprising the glutamine may include LGPGQSKVIG (SEQ ID NO:48) or GEGQQHHLGG (SEQ ID NO:49). Of particular interest are backbones having fibroin and elastin repetitive units coming within the description provided previously, where one of the fibroin or elastin units has one of the amino acids substituted with the reactive amino acid. Particularly, by having a single available cysteine in the pendent group (there may be more than one cysteine, so long as the other cysteines are unreactive, e.g. protected with a removable protective group), the pendent groups may be readily attached to the backbone polymer by means of thioether formation with an activated olefin.

The subject compositions find particular use in the formation of articles of manufacture, by themselves or in combination with other materials. In one application, articles may be produced for use internally to a mammalian host, where there is an interest in biocompatibility, resorption rate, ability to vascularize, tissue adhesive and/or bonding capability, and the like. Various articles can be prepared, such as gels, films, threads, coatings, formed objects, such as pins and screws, or injectable compositions which are flowable, where the injectable composition may set up and bond or seal tissues, form a depot for a drug, or be a filler, coating, or the like. The injectable composition may be administered with a syringe, catheter, trocar, or the like. The formed objects may be prepared in accordance with conventional ways, such as molding, extrusion, precipitation from a solvent, solvent evaporation, and the like. The flowable depot can be obtained by using a molecular dispersion, fine particles in a medium saturated with the polymer, using a melt, where the melting temperature may be achieved by adding physiologically acceptable additives, and the like.

The articles may find use in a variety of situations associated with the implantation of the article into a mammalian host or the application of the article to the surface of a mammalian host, e.g. wound healing, burn dressing, etc. Those situations, where the performance of the article may be retained for a predetermined time and replaced by natural materials through natural processes, desirably employ materials which will be resorbed after having fulfilled their function in maintaining their role until the natural process has reestablished a natural structure. Thus, the compositions may find use in holding tissue together, covering tissue, encapsulating cells or organs, providing a coating that cells can invade and replace the composition with natural composition, e.g. bone, soft tissues, and the like.

To enhance the rate of setup of the polymeric composition, the composition may be prepolymerized. When prepolymerized, usually at least about 10% of the total number of cross-links which are present upon completion of the cross-linking reaction may be formed and usualy not more than 75%, more usually not more than about 50%. Depending on the utility of the product, the number of cross-links introduced with prepolymerization should allow the prepolymerized composition to remain workable and provide sufficient time prior to setup where it is no longer workable for application.

Alternatively, one may wish to provide for a relatively constant supply of a particular agent, particularly a drug, whereby a depot may be introduced into the mammalian host which will degrade over a predetermined time. The depot may be prepared from the resorbable composition and drug, so that as the external surface of the depot is eroded, drug will be released. By controlling the form of the depot, whereby a relatively constant volume of the resorbable material is degraded over an extended period of time, the drug level may be maintained during that period.

The period required for resorption can be as short as 0.5 days and may exceed 4 weeks, 6 weeks, 8 weeks or more depending upon the particular choice of composition. Thus, the period of maintenance of the composition may be greatly varied.

The subject compositions may be used to provide compositions where various functionalities may be affixed to a backbone polymer at will. For example, where the polymer has been affixed in place, by adding less than saturating amounts of a low molecular weight isopeptide bond forming reactant from time to time, one can affix functionalities or activities, e.g. radioactivity, fluorescence, light absorption, magnetic particles, etc. to the site. By adding a compound comprising a reactive sequence and functionality with FXIIIa to the polymer, whereby isopeptide bond formation will occur, the functionality or activity will become covalently bonded to the polymer.

The subject compositions may also be used in assays, where one can determine the amount of analyte by having a competition between a conjugate of the analyte with the enzyme FXIIIa or a small molecule having a reactive sequence which forms the isopeptide link, e.g. lysine, where the polymer has glutamine. Competitive assay protocols are well known in the art and do not require exemplification here.

The compositions may be prepared in accordance with conventional ways. For the polymers which have the consensus sequence in the polymer chain, a method which may be employed is described in U.S. Pat. No. 5,243,038. Briefly, sequences may be synthesized comprising a plurality of repeating units, where complementary sequences result in dsDNA having overhangs. A series of dsDNA molecules may be prepared and stepwise introduced into a cloning vector as the gene for the protein is constructed. A unit can be obtained in this way, which may be sequenced to ensure that there have been no changes in the sequence, followed by multimerization of the unit, cloning and expression. For further details, see the above-indicated patent.

For the compositions, where the reactive sequences are side chains, one can provide for a wide variety of active functionalities when synthesizing the side chain, which will allow for covalent bonding to the backbone polymer. The backbone polymers may be modified, as appropriate, for covalent linkage. The synthetic polymers may be modified by oxidation to provide hydroxyl groups, sulfonation to provide sulfonyl groups, and the like. During the polymerization, monomers may be introduced which provide for reactive sites. With the lactides and glycolides, 4-hydroxybut-2-enoic acid may be employed as a comonomer, and the like. For example, a mercaptan group may be provided, where the polymer has an active olefinic group. Alternatively, carboxyl, hydroxyl or amino groups may be present, which allow for attachment. Because of the variety of polymers and groups which may be present on the side chain, no general methodology can be described. With the naturally occurring polymers, there will normally be present a large number of active functionalities for linking. Methods of linking compounds to such naturally occurring polymers are well known in the art.

The following examples are offered by way of illustration and not by way of limitation.

EXPERIMENTAL

EXAMPLE 1

Methods

The construction of synthetic DNA and its use in large polypeptide synthesis is described in U.S. Pat. No. 5,243, 038; PCT/US89/05016 and PCT/US92/09485, the disclosures of which are herein incorporated by reference. Modifications to these methods and additional methods used are described below.

1. Use of filters and columns for DNA Purification

A. Ultrafree®-Probind filter unit ("Probind", Millipore): the DNA containing solution was applied to the filter unit and spun at 12,000 RPM for 30 seconds in a Sorvall Microspin 24S.

B. Microcon-30 filter (Amicon): the DNA containing solution was washed by applying to the filter and exchanging twice with $H_2O$ by spinning at 12,000 RPM for 6 min in a microfuge.

C. Bio-Spin 6 column ("Bio-Spin", BioRad): Salts and glycerol were removed from the DNA solution by applying to the column, previously equilibrated in TEAB (triethyl ammonium bicarbonate pH 7.0), and spinning in a Sorvall RC5B centrifuge using an HB4 rotor at 2,500 RPM for 4 min.

2. Phosphatase treatment of DNA

Phosphatase treatment of DNA was also performed by resuspending ethanol precipitated DNA from the restriction enzyme digest in 20 mM Tris-HCl pH 8.0, 10 mM $MgCl_2$ to a final DNA concentration of 20 µg/ml. Shrimp Alkaline Phosphatase (SAP) was added at 2 U/µg of DNA and the mixture was incubated at 370° C. for one hour, heat inactivated for 20 minutes at 65° C. and then passed through a Probind filter and subsequently a Bio-Spin column.

3. Preparative agarose gel electrophoresis

For agarose ligation, the buffer used was 1×TAE (50 mM Tris-acetate, pH 7.8).

4. Agarose DNA Ligation

The agarose was melted at 65° C., the temperature was then lowered to 37° C. and ligation buffer (5×=100 mM Tris-HCl, pH 7.5, 50 mM $MgCl_2$, 50 mM DTT, 1 mM ATP) was added; the tube was then placed at room temperature and ligase was added (1000 units T4 DNA ligase (NEB)). The reaction volume was usually 50 µl. The reaction was incubated at 15° C. for 16–18 hrs.

5. Agarose DNA purification using an Ultrafree®-MC Filter Unit

This procedure can be used for agarose slices up to 400 µl in size. After agarose gel electrophoresis, the DNA is visualized by ethidium bromide staining and the agarose block containing the DNA band of interest is excised. The agarose is then frozen at −20° C. for 1 hour, then quickly thawed at 37° C. for 5 minutes. The agarose is then thoroughly macerated. The pieces are then transferred into the sample cup of the filter unit and spun at 5,000 xg in a standard microfuge for 20 minutes. The agarose is then resuspended in 200 µl of Tris-EDTA, or other buffer, and incubated at room temperature for 30 minutes to allow for elution of additional DNA from the gel. The mixture is then centrifuged for an additional 20 minutes at 10,000 RPM. The DNA is, at this point, in the filtrate tube separated from the agarose fragments and ready for subsequent DNA manipulations.

6. Preparation of antibody to artificially synthesized peptides

Following the same procedure as described in U.S. Pat. No. 5,243,038, an additional antigen was synthesized having the sequence (GAPGAPGSQGAPGLQ)$_2$YMK (SEQ ID NO:09) which was then coupled to keyhole limpet hemocyanin for use as an immunogen. Polyclonal antisera ("CLP antibody") were then prepared which bound to the CLP 3.7 and PPAS polymers described below.

7. Immunoblotting of proteins in gels

An alternative to the $^{125}$I-Protein A detection method was used. This method relied on a chemiluminescent signal activated by horseradish peroxidase (HRP). The chemiluminescent reagents are readily available from several suppliers such as Amersham and DuPont NEN. The western blot was prepared and blocked with BLOTTO. A number of methods were used to introduce the HRP reporter enzyme including, for example, a hapten/anti-hapten-HRP, a biotinylated antibody/streptavidin-HRP, a secondary reporter such as a goat or mouse anti-rabbit IgG-biotinylated/streptavidin-HRP, or a goat or mouse-anti rabbit IqG-HRP. These reagents were bought from different sources such as BioRad or Amersham and occasionally biotinylated antibodies were prepared in our laboratory using Biotin NHS from Vector Laboratories, Burlingame, Calif. (Cat. #SP-1200) following the procedure accompanying the product. The following is an example of a procedure used to detect the expression of protein polymers.

The blot was placed in 15 ml of BLOTTO solution containing biotinylated goat anti-rabbit IgG (BioRad) diluted in BLOTTO (1:7500) and gently agitated for 2 hrs at room temperature. The filter was then washed for 30 minutes with 3 changes of TSA (50 mM Tris-HCl pH 7.4, 0.9% NaCl, 0.2% sodium azide). The blot was then incubated for 20 minutes at room temperature with gentle rotation, in 20 ml of TBS (100 mM Tris Base, 150 mM NaCl, pH 7.5) HRP-Streptavidin (Amersham) diluted 1:1000 in TBS with 0.1% Tween 20. The blot was then washed three times for 5 minutes each in TBS with 0.3% Tween 20 and then three times for 5 minutes each in TBS with 0.1% Tween 20. The blot was then incubated for 1 minute with gentle agitation in 12 ml of development solutions #1 an #2 (Amersham) equally mixed. The blot was removed from the development solution and autoradiographed.

8. Protein expression analysis

An overnight culture which had been grown at 300 C was used to inoculate 50 ml of LB media contained in a 250 ml flask. Kanamycin was added at a final concentration of 50 µg per ml and the culture was incubated with agitation (200 rpm) at 30° C. When the culture reached an $OD_{600}$ of 0.8, 40 ml were transferred to a new flask prewarmed at 42° C. and incubated at the same temperature for approximately 2 hours. The cultures (30° and 42°) were chilled on ice and $OD_{600}$ was taken. Cells were collected by centrifugation and then divided in 1.0 $OD_{600}$ aliquots and used to perform western analysis using the appropriate antibodies.

9. Amino acid analysis

Amino acid derivatives were analyzed by reverse phase HPLC using a Waters 600E system.

10. Peptide Synthesis

Synthetic peptides were also prepared on a Rainin/Protein Technologies PS3 FMOC peptide synthesizer. Both the synthesis and cleavage were accomplished using the methods supplied by the manufacturer in the instrument manual.

11. In vitro DNA synthesis

The β-cyanoethyl phosphoramidites, controlled-pore glass columns and all synthesis reagents were obtained from Applied Biosystems, Foster City, Calif. Synthetic oligonucleotides were prepared by the phosphite triester method with an Applied Biosystems Model 381A DNA synthesizer using a 10-fold excess of protected phosphoramidites and 0.2 μmole of nucleotide bound to the synthesis support column. The chemistries used for synthesis are the standard protocols recommended for use with the synthesizer and have been described (Matteucci et al., *J. Amer. Chem. Soc.*, 103:3185–3319 (1981)). Deprotection and cleavage of the oligomers from the solid support were performed according to standard procedures as provided by Applied Biosystems. The repetitive yield of the synthesis as measured by the optical density of the removed protecting group as recommended by Applied Biosystems was greater than 97.5%.

The crude oligonucleotide mixture was purified by preparative gel electrophoresis as described by the Applied Biosystems protocols in Evaluating and Isolating Synthetic Oligonucleotides, 1992 (Formerly: User Bulletin 13, 1987). The acrylamide gel concentration varied from 10 to 20% depending upon the length of the oligomer. If necessary, the purified oligomer was identified by UV shadowing, excised from the gel and extracted by the crush and soak procedure (Smith, *Methods in Enzymology*, 65:371–379 (1980)).

For DNA synthesis of oligonucleotides longer then 100 bases, the synthesis cycle was changed from the protocol recommended by Applied Biosystems for the 381A DNA synthesizer. All the reagents used were fresh. All the reagents were supplied by Applied Biosystems except for the acetonitrile (Burdick and Jackson Cat#017-4 with water content less then 0.001 %) and the 2000 Å pore size column (Glen Research). Due to the length of the oligo, interrupt pauses had to be inserted during the synthesis to allow changing the reagent bottles that emptied during synthesis. This interrupt pause was done at the cycle entry step and the pause was kept as short as possible. The washes after detritylation by TCA, through the beginning of each synthesis cycle, were increased from about 2x to 3x over the recommended time. The time allocated for the capping was also increased to limit truncated failure sequences. After the synthesis the deprotection was done at 55° C. for 6 hours. After desalting the synthesized DNA was amplified using PCR.

12. Sequencing of DNA

Storage and analysis of data utilized software from DNA Strider, DNA Inspection IIe or DNAid for Apple Macintosh personal computer.

13. Dideoxy DNA sequencing of double stranded plasmid DNA

As described in U.S. Pat. No. 5,243,038, plasmid DNA was prepared on a small scale. Primers were synthesized using a DNA synthesizer and were annealed to the plasmid DNA following the procedure described for M13 sequencing. The sequencing reactions were done using Sequenase (United States Biochemicals) and the conditions were as recommended by the supplier. All sequences were run on polyacrylamide gels.

14. PCR Amplification

The PCR reaction was performed in a 100 μl volume in a Perkin Elmer thin-walled Gene Amp™ reaction tube. Approximately 1 μM of each primer DNA was added to 1× PCR buffer (supplied by Perkin Elmer as 10× solution), 200 μM of each dNT, 5U AmpliTaq, and several concentrations of the target DNA. Amplification was performed in a Perkin Elmer DNA Thermal cycler model 480 for 30 cycles with the following step cycles of 12 min each: 95° C., 62° C., and 72° C. Aliquots from the different reactions were analyzed by agarose gel electrophoresis using 1.5% low melting point agarose in 0.5× TA buffer. The reaction mixtures that gave the desired band were pooled and spun through a Probind filter to remove the AmpliTaq enzyme, then a Microcon-30 filter and a Bio-Spin column. The DNA was then concentrated in vacuo.

15. Fermentation conditions

The fermentors used for the expression of protein polymers were usually a 15 l MBR, 10 l working volume, or a 13 l Braun Biostat E, 8.5 l working volume. The choice of the fermentor and its size is not critical. Any media used for the growth of *E. coli* can be used. The nitrogen source ranged from NZAmine to inorganic salts and the carbon source generally used was glycerol or glucose. All fermentations were done with the appropriate selection conditions imposed by the plasmid requirements (e.g. kanamycin, ampicillin, etc.). The fermentation method used to express protein polymers in *E. coli* was the fed-batch method. This is the preferred method for the fermentation of recombinant organisms even if other methods can be used.

The fed-batch method exploits the stage of cell growth where the organisms make a transition from exponential to stationary phase. This transition is often the result of either depletion of an essential nutrient or accumulation of a metabolic byproduct. When the transition is the result of nutrient depletion, the addition of nutrients to the system causes cell division to continue. One or more essential nutrients can incrementally be added to the fermentation vessel during the run, with the net volume increasing during the fermentation process. The result is a controlled growth rate where biomass and expression levels can be optimized. When the cell number in the culture has reached or is approaching a maximum, protein polymer production is induced by providing an appropriate physical or chemical signal, depending upon the expression system used. Production will then continue until the accumulated product reaches maximum levels (Fiestchko, J., and Ritch, T., *Chem. Eng. Commun.* 1986, 45: 229–240. Seo, J. H.; Bailey, J. E., Biotechnol. Bioeng. 1986, 28: 1590–1594.

EXAMPLE 2

Factor XIIIa reactive peptides

The sequence of fibrin and of the native cross-linking site is known. The bovine milk protein B-casein is a known substrate for factor XIIIa. Peptide blocks which include a factor XIIIa cross-linking site and retain activity towards factor XIIIa were produced. These peptide blocks or similar amino acid sequences were then conjugated to high molecular weight carrier polymers or were used in the construction of protein polymers. When a formulation (aqueous and physiological) containing such polymers is mixed with factor XIIIa, it will undergo cross-linking leading to a setting reaction in which the polymer solution will be converted to a stiff gel or clot. The degree and spacing of cross-linking will influence the setting time and mechanical properties and cohesive strength of the gel. When applied on or in a tissue, an adhesive bond will be created both through physical adsorption to the tissue matrix and through covalent bonding to available tissue proteins.

A synthetic peptide was synthesized containing the amino acid sequence VLSLSQSKVLPVPE (SEQ ID NO:10) (peptide 93.1) corresponding to residues 162–175 of bovine B-casein as published by Dumas, B. R., Brignon, G., Grosclaude, F., Mercier, J. C. (1972) *Eur. J. Biochem.* 25, 505–514. The peptide was shown to serve as a substrate for factor XIIIa cross-linking using HPLC analysis. A solution containing the peptide was incubated with thrombin activated factor XIII in the presence of excess monodansylcadaverine (MDC). MDC is a fluorescent amino group containing compound which serves as a lysine analog for factor XIIIa. The reaction products were separated by reverse phase high performance liquid chromatography. The unreacted peptide peak migrated with a retention time of 21 minutes. A new peak with a retention time of 23.5 minutes was observed in the reaction mixture and its area was proportional to the time of reaction. The new peak was isolated and its atomic mass was determined by mass spectrometry to be 1815. The combined mass of peptide 93.1 (1496) plus MDC (335) is 1831. If the transglutaminase activity of factor XIIIa forms an isopeptide bond between the peptide glutamine side chain and an available primary amino group, the reaction should liberate an ammonium ion, $NH_3+(NH_2$ from the glutamine amide and H from water) according to the reaction below:

Factor XIIIa Transglutaminase Reaction

Reactants:
Peptide 93.1-glutamine-$CH_2CH_2CO-NH_2 + NH_2-CH_2CH_2CH_2CH_2CH_2NH$-Dansyl + $H_2O$
    mw = 1496               mw = 335

Products:
Peptide 93.1-glutamine-$CH_2CH_2CO-NH_2-CH_2CH_2CH_2CH_2CH_2NH$-Dansyl + $NH_3$ + OH—
    mw = 1315

The difference between the sum of the molecular weights of the substrates and the theoretical product is 16 atomic units, the loss of $NH_2$. The mass of the new peak matches exactly the mass of the theoretical reaction product of Peptide 93.1 and MDC by factor XIIIa. No other combinations of reaction products match the mass of the new peak. Therefore, it is concluded from this data that factor XIIIa will create a covalent bond between Peptide 93.1 and a compound containing an active amino group. The conversion of Peptide 93.1 to MDC-Peptide 93.1 occurred with a Km of approximately $1.8×10^{-3}M$.

According to the sequence of human fibrin gamma chain (Rixon, M. W., Chung, D. W. and Davie, W. W., *Biochemistry* 22, 2077–2086, 1985), the carboxyl terminal 17 amino acids (residues 421 to 437, GEGQQHHLGGAKQAGDV (SEQ ID NO:11) contain the residues glutamine (Q424) and lysine (K432) which participate in the isopeptide bond formed by the transglutaminase activity of factor XIIIa. Contained also within this sequence is a platelet binding activity. This peptide (Peptide 93.3) was synthesized and similarly shown to serve as a substrate for factor XIIIa.

Similar results were obtained with Peptide 93.2 (GEGQQHHLGGARQAGDV)(SEQ ID NO:12). This sequence corresponds to amino acids 421–437 (SEQ ID NO:11) of human fibrin gamma-A protein except that K432 of the natural sequence has been substituted with arginine (R). This substitution conserves the overall charge of the peptide block while eliminating the primary amino group of lysine which may participate in transglutaminase activity. It retains the reactive glutamine Q424 and the flanking recognition sequences for cross-linking. The K to R substitution prevents factor XIIIa cross-linking the peptide with itself. Using reverse phase high performance liquid chromatography, Peptide 93.2 (SEQ ID NO:12) eluted with a retention time of 15 minutes. A new peak with a retention time of 19 minutes appeared when Peptide 93.2 (SEQ ID NO:12) was reacted with thrombin activated factor XIII and MDC. The amount of the new species increased with increased reaction time. Factor XIIIa caused the conversion of Peptide 93.2 to this product with a Km of approximately $5.8×10^{-4}M$.

An additional amino acid sequence (Peptide 93.4) was designed that lacks the reactive glutamine Q424. Since this sequence block only includes fibrin gamma chain residues 429–437 (GGAKQAGDV)(SEQ ID NO:13), it can only serve as a lysine donor to factor XIIIa mediated cross-linking.

Polymeric substrates comprising either Peptide 93.2 (SEQ ID NO:12) or 93.4 (SEQ ID NO:13) alone cannot undergo extensive cross-linking by transamination. Mixtures of such polymers, where each contains only one-half of the substrate required for cross-linking, can be used to promote interstrand cross-linking, thereby improving cohesive bond strength and mechanical properties. By mixing them in disproportionate ratios, they may also be used to produce adhesive formulations with excess Q424 activity, for instance, to promote the probability of adhesive/tissue bonding. Although, factor XIIIa is fairly specific, using glutamine residues which have conserved flanking amino acid sequences, it is fairly promiscuous in its use of lysine residues. Lysines in tissue proteins such as collagen and fibronectin may participate in adhesive cross-linking adding to the strength of the adhesive bond.

EXAMPLE 3

Construction of Plasmids Used to Create Protein Polymer Adhesive Substrates

Construction of plasmid pPT0285

Plasmid pACYC184 (Chang, A. Y. C. and Cohen, S. N., *J. Bacteriol.* 134:1141–1156 (1978)) was digested with BanI REN, purified by agarose gel electrophoresis, and the DNA fragment corresponding to approximately 2,000 bp was further purified using a NACS column. This DNA fragment was filled in using DNA polymerase and then self-ligated. The products of the ligation mixture were transformed into *E. coli* strain HB101 and selected on bacterial plates containing chloramphenicol at 30 μg/ml. Plasmid DNA from individual colonies was linearized by digestion with Eco47III. One clone, pPT0235, was used as the acceptor vector for subsequent DNA manipulations.

Two oligonucleotide strands (SEQ ID NOS:14–15) were synthesized and purified:

```
       (Eco47III)PmeI        PmlI      NruI      BanI      StuI      EcoRV   SnaBI(SnaI)
1. 5'-GCTATGTTTAAACCACGTGTTCGCGATCCGGGTGCCGATCCAGGCCTGCGATATCAGTACGTA
2. 3'-CGATACAAATTTGGTGCACAAGCGCTAGGCCCACGGCTAGGTCCGGACGCTATAGTCATGCAT
        A   M   F   K   P   R   V   R   D   P   G   A   D   P   G   L   R   Y   Q   Y   V
       (SEQ ID NO:42)
```

The two oligonucleotide strands were annealed and ligated with the DNA of plasmid pPT0235 which had been digested with Eco47III and SnaI RENs. The products of this ligation reaction were transformed into E. coli strain HB101. Plasmid DNA from transformants was purified and digested with EcoRI in combination with Eco47III or SnaI or NruI RENs. Plasmid DNA from two clones that gave the correct digestion pattern was sequenced. One plasmid, designated pPT 0285, was found to be correct and chosen for further constructions.

One oligonucleotide strand coding for the CLP 3.7 gene monomer (see Table 1) was synthesized using an Applied Biosystems DNA synthesizer model 381A and a 2000 Å synthesis column supplied by Glen Research. After the synthesis, the 226 base DNA segment was deprotected and cleaved from the column support by treatment in NH4OH at 55° C. for 6 hrs.

The PCR reaction was then performed as previously described. The amplified DNA was resuspended and digested with BanI REN. The digested DNA was purified using a Probind filter followed by a Bio-Spin column and then ligated with pPT0285 previously digested with BanI REN and treated with SAP. The products of the ligation reaction were transformed into E. coli strain HB101. Plasmid DNA from transformants was purified and analyzed as follows. Colonies were picked and transferred onto a plate and into a 0.5 ml microfuge tube containing 50 µl of lysis buffer (1% Tween 20, 10 µM Tris-HCl pH 8.0, 1 mM EDTA). The tube was closed, incubated at 95° C. for 10 min and then cooled to room temperature. 5 µl of lysate was added to 45 µl MasterMix (1× PCR buffer as described previously, 5U Amplitaq, 200 µM dNTPs) in a 0.5 ml Perkin Elmer thin-walled Gene Amp reaction tube. Amplification was performed in a Perkin Elmer DNA Thermal cycler

TABLE 1

```
5'- ATGGCAGCGAAAGGGGACCGGTGCCCCGGGTACTCCTGGTCCACAAGGTCTGCCGGGAAGCCCAGGG
    GCTCCGGGTACTCCAGGTCCGCAAGGCCTGCCGGGTTCACCGGGTGCTCCGGGAACTCCTGGCCCGC
    AGGGCTTGCCGGGATCCCCAGGTGCACCAGGAACGCCGGGACCTCAGGGTCTTCCGGGTAGCCCTGG
    TGCCTTTCCGCTAAAGTCCTGCCGT -3'(SEQ ID NO:16)
```

Two additional DNA strands were synthesized to be used as primers for PCR amplification. The two strands were:

5'- AAG AAG GAG ATA TCA TAT GGC AGC GAA AGG GGA CC -3' (SEQ ID NO:17)

5'- CGC AGA TCT TTA AAT TAC GGC AGG ACT TTA GCG GAA A-3' (SEQ ID NO:18)

model 480 for 30 cycles with the following step cycle of 1 min each: 95° C., 52° C., and 72° C. Aliquots from the different reactions were analyzed by agarose gel electrophoresis using 1.5% low melting point agarose in 0.5× TAE buffer. Plasmid DNA from the clones showing the correct size insert was purified and analyzed by DNA sequencing. Plasmid pPTo310 contained the desired CLP 3.7 monomer sequence (see Table 2).

TABLE 2

(SEQ ID NO:19)

```
    BanI     AvaI/SmaI
5'- GGTGCCCCGGGTACTCCTGGTCCACAAGGTCTGCCGGGAAGCCCA
3'- CCACGGGGCCCATGAGGACCAGGTGTTCCAGACGGCCCTTCGGGT
      G   A   P   G   T   P   G   P   Q   G   L   P   G   S   P

BanII          GsuI              StuI           DraIII
    GGGGCTCCGGGTACTCCAGGTCCGCAAGGCCTGCCGGGTTCACCG
    CCCCGAGGCCCATGAGGTCCAGGCGTTCCGGACGGCCCAAGTGGC
      G   A   P   G   T   P   G   P   Q   G   L   P   G   S   P

BglI               BamHI
    GGTGCTCCGGGAACTCCTGGCCCGCAGGGCTTGCCGGGATCCCCA
    CCACGAGGCCCTTGAGGACCGGGCGTCCCGAACGGCCCTAGGGGT
      G   A   P   G   T   P   G   P   Q   G   L   P   G   S   P

EcoO109I                             BanI
    GGTGCACCAGGAACGCCGGGACCTCAGGGTCTTCCGGGTAGCCCTGGTGCC -3'
    CCACGTGGTCCTTGCGGCCCTGGAGTCCCAGAAGGCCCATCGGGACCACGG -5'
      G   A   P   G   T   P   G   P   Q   G   L   P   G   S   P   (G   A)
    (SEQ ID NO:43)
```

CLP 3.7 Polymer construction

Plasmid DNA from pPT00310 was digested with BanI-REN and the digestion fragments were separated by agarose gel electrophoresis. The CLP 3.7 gene fragment, 180 bp, was excised and purified by NACS column (see Methods). The purified fragment was ligated with plasmid pSY1262 which had been prepared as follows: pSY1262 plasmid DNA was digested with BanI REN and subsequently treated with Shrimp Alkaline Phosphatase (SAP) as described in Example 1.

The product of this ligation reaction was transfored into *E. coli* strain HB101. Transformants were selected for resistance to kanamycin. Plasmid DNA from individual transformants was purified and analyzed for increased size due to CLP 3.7 multiple DNA insertion. Several clones were obtained and two of them containing inserts of approximately 1.25 kbp and 2.6 kpb (pPT0314 and pPT0312 respectively) were chosen to be used for expression of CLP 3.7.

CLP 3.7 Analysis

*E. coli* strain HB101 containing plasmid pPT0312 or pPT0314 were grown as described in Example 1. The proteins produced by these cells were analyzed by SDS-PAGE for detection of reactivity to CLP antibodies. In every analysis a strong reactive band was observed with an apparent molecular weight of 130 kD and 50 kD respectively.

pPT0312    CLP 3.7    837 AA    MW 72,637

MDPVVLQRRDWENPGVTQLNRLAAHPPFASDPM
[(GAPGTPGPQGLPGSP)$_4$]$_{13}$
GAMDPGRYQLSAGRYHYQLVWCQK
(SEQ ID NO:50)

EXAMPLE 4

Protein Polymer Adhesive Substrates (PPAS)

PPAS polymers were designed to include oligopeptide blocks of human fibrin gamma chain which contain either all or part of the site of factor XIIIa cross-linking. The amino acid sequences of Peptides 93.3 (SEQ ID NO:11), 93.2(SEQ ID NO:12), and 93.4(SEQ ID NO:13) were incorporated within a structural backbone consisting of 3 complete repeats of a 15 amino acid peptide block of human collagen type I (GAPGTPGPQGLPGSP (SEQ ID NO:20), the CLP3.7 monomer repeating amino acid sequence) and designated PPAS1-A, PPAS1-B, and PPAS1-C, respectively.

A variety of structural backbones can be used in the design of adhesive polymers with the option of changing the physical properties of the polymer chain. The composition of the backbone will effect the solubility of the polymer as well as its rheological properties. CLP (collagen-like protein) polymers are useful in this respect in that they are extremely soluble in water, allowing protein solutions of greater than 10 weight percent to be formed while still maintaining good flow properties. CLP polymers have good adhesion to hydrophilic surfaces such as glass and therefore may adhere well to tissue. However, other backbones with different properties such as SLP (silk-like protein), ELP (elastin-like protein), KLP (keratin-like protein), or copolymers of these could also supply useful properties.

The 17 amino acid fibrin block of Peptide 93.3 (SEQ ID NO:13) was integrated with the CLP3.7 monomer sequence (SEQ ID NO:20) so as to recreate its hydrophobicity and secondary structure environment matching, as closely as possible, that of human fibrin. Although, this 17 amino acid block is the C-terminal sequence of fibrin gamma chain (chain-A), a variant gamma chain (chain-B) exists in the blood which contains an additional 16 amino acids beyond the cross-linking site. Because the gamma-B chain also participates in factor XIIIa cross-linking, it follows that the 17 amino acid sequence block does not have to be C terminal for activity. Thus, it can be expected that protein polymers consisting of tandem repeats of monomer blocks containing the fibrin gamma factor XIIIa cross-linking sequence, will contain multiple, active sites of potential cross-linking. Cross-linking may occur between polymer chains and with neighboring tissue. During normal healing of the wound, the protein based adhesive will be degraded and resorbed using essentially the same mechanisms of proteolysis by which normal blood clots are dissolved. The products of degradation are peptides of essentially human sequence or amino acids which may be reutilized by the body.

PPAS1-A gene monomer synthesis and construction

The PPAS1-A amino acid monomer sequence with the fibrin gamma sequence shown in bold is as follows:

$(GAPGTPGPQGLPGSP)_3$GAPGTPGEGQQHHLGGAKQAGDVGSP
(SEQ ID NO:21)

One oligonucleotide strand (see Table 3) was synthesized using an Applied Biosystems DNA synthesizer model 381A and a 2000 Å pore resin synthesis column supplied by Glen Research. During the synthesis, the required interrupt-pause steps for reagent bottle changes were minimized. After the synthesis, the 123 base DNA fragment was deprotected and cleaved from the column support by treatment in ammonium hydroxide at 55° C. for 6 hrs.

TABLE 3

| (SEQ ID NO:22) |
|---|
| 5'- ATGGCAGCGAAAGGGGACCGTGCACCAGGAACGCCGGGAGAAGGTCAACAGCACCATCTTGGTGG<br>AGCGAAACAGGCAGGCGACGTCGGTAGCCCTGGTGCCTTTCCGCTAAAGTCCTGCCGT -3' |

The PCR reaction was then performed as previously described using the same primers as were used in the construction of the CLP3.7 monomer. The amplified DNA was then resuspended and digested with ApaLI and DraI RENs. The digested DNA was then purified using a Probind filter followed by a Bio-Spin column and then ligated with pPT0310 previously digested with ApaLI and EcoRV RENs and purified by NACS column. The products of the ligation reaction were transformed into *E. coli* strain HB101. Plasmid DNA from transformants was purified and analyzed by digestion using EcoO109, HincII and HindIII RENs. Plasmid DNA from the clones showing the correct size insert was purified and analyzed by DNA sequencing. Plasmid pPT0318 contained the desired PPAS1-A gene monomer sequence (see Table 4).

TABLE 4

(SEQ ID NO:23)

```
     BanI     AvaI/SmaI
5'-  GGTGCCCCGGGTACTCCTGGTCCACAAGGTCTGCCGGGAAGCCCA
3'-  CCACGGGGCCCATGAGGACCAGGTGTTCCAGACGGCCCTTCGGGT
     G   A   P   G   T   P   G   P   Q   G   L   P   G   S   P

BanII              GsuI              StuI              DraIII
     GGGGCTCCGGGTACTCCAGGTCCGCAAGGCCTGCCGGGTTCACCG
     CCCCGAGGCCCATGAGGTCCAGGCGTTCCGGACGGCCCAAGTGGC
     G   A   P   G   T   P   G   P   Q   G   L   P   G   S   P

BglI                   BamHI
     GGTGCTCCGGGAACTCCTGGCCCGCAGGGCTTGCCGGGATCCCCA
     CCACGAGGCCCTTGAGGACCGGGCGTCCCGAACGGCCCTAGGGGT
     G   A   P   G   T   P   G   P   Q   G   L   P   G   S   P

GGTGCACCAGGAACGCCGGGAGAAGGTCAACAGCACCATCTTGGT
     CCACGTGGTCCTTGCGGCCCTCTTCCAGTTGTCGTGGTAGAACCA
     G   A   P   G   T   P   G   E   G   Q   Q   H   L   G

AatII                   BanI
     GGAGCGAAACAGGCAGGCGACGTCGGTAGCCCTGGTGCC   -3'
     CCTCGCTTTGTCCGTCCGCTGCAGCCATCGGGACCACGG   -5'
     G   A   K   Q   A   G   D   V   G   S   P   (G   A)   (SEQ ID NO:44)
```

Construction of expression plasmid pPT0317

Plasmid DNA pSY1262 was linearized with PvuII REN, then passed through a Probind filter followed by a Bio-Spin column. The DNA was then treated with SAP and ligated with a DNA fragment from pQE-17 (QIAGEN Catalog #33173) prepared as follows. Plasmid DNA pQE-17 was digested with BglII and HindIII RENs and the 36 bp fragment (see Table 5) was purified using a Probind filter and then a Bio-Spin column. The DNA was purified further using a Microcon-30 filter and the filtrate containing the 36 bp was kept. The DNA was then treated with DNA Polymerase I and purified through a Probind filter and then a Bio-Spin column.

TABLE 5

```
5'-  GATCTTCGATCTCATCACCATCACCATCACTA         (SEQ ID NO:24)
3'-          AAGCTAGAGTAGTGGTAGTGGTAGTGATTCGA  (SEQ ID NO:25)
```

The products of the ligation reaction were transformed into E. coli strain HB101. Plasmid DNA from transformants was purified and analyzed by digestion using BstYI and Bst1107I RENs. Plasmid DNA from the clones showing the correct restriction pattern was purified and analyzed by DNA sequencing. Plasmid pPT0317 contained the desired DNA insert and was used for further DNA manipulations.

PPAS1-A polymer construction

Plasmid DNA from pPT0318 was digested with BanI REN and the digestion fragments were separated by agarose gel electrophoresis. The PPAS1-A gene fragment, 216 bp, was excised and purified using the Ultrafree-MC filter. The purified fragment was ligated with plasmid pPT0317 which had been prepared as follows. Plasmid DNA pPT0317 was digested with BanI REN, then passed through a Probind filter and then a Bio-Spin column. The DNA was then treated with SAP.

The products of the ligation reaction were transformed into E. coli strain HB101. Transformants were selected for resistance to kanamycin. Plasmid DNA from individual transformants was purified and analyzed using EcoRI and EcoRV RENs for the presence of PPAS1-A multimer gene inserts. Several clones were obtained with insert sizes ranging from 200 bp to approximately 4 kb. Several clones containining from 10 to 20 repeats were chosen for use in expression of the PPAS1-A polymer.

PPAS1-A expression analysis

E. coli strain HB101 containing plasmid pPT0321, pPT0325, pPT0326, or pPT0327 was cultured as previously described. The proteins produced by these cells showed strong reactive bands of apparent molecular weights ranging from 80 kD to 180 kD when analyzed by western blot for reactivity to CLP antibody. One clone, pPT0321, containing 10 repeats of the PPAS1-A monomer was selected for further study.

pPT0321 (SEQ ID NO:26)  PPAS1-A  762 AA  MW  68,056
MDPVVLQRRDWENPGVTQLNRLAAHPPFASDPM
[(GAPGTPGPQGLPGSP)$_3$ GAPGTPGEGQQHHLGGAKQAGDVGSP]$_{10}$
GAMDPGRYQDLRSHHHHHH

PPAS1-B gene monomer synthesis and construction

The PPAS1-B amino acid monomer sequence with the fibrin gamma sequence shown in bold is as follows:

(GAPGTPGPQGLPGSP)$_3$ GAPGTPGEGQQHHLGGARQAGD-
VGSP (SEQ ID NO:27)

Two oligonucleotide strands (see Table 6) were synthesized and purified as previously described.

TABLE 6

```
1. 5'        GTGGAGCTCGCCAGGCAGGCGACGT (SEQ ID NO:28)
2. 3'  GAAGCACCTCGAGCGGTCCGTCCGC     (SEQ ID NO:29)
```

These oligonucleotide strands were annealed and ligated with plasmid pPT0318 which had been digested with BstXI and AatII RENs. The products of this ligation reaction were transformed into *E. coli* strain HB101. Plasmid DNA from transformants was purified and digested with NcoI and SacI RENs to determine whether they had the correct restriction pattern. Plasmid DNA from correct clones was sequenced. Plasmid pPT0320 (shown in Table 7) contained the desired PPAS1-B monomer sequence.

TABLE 7

(SEQ ID NO:30)

```
5'-   GGTGCCCCGGGTACTCCTGGTCCACAAGGTCTGCCGGGAAGCCCA
3'-   CCACGGGGCCCATGAGGACCAGGTGTTCCAGACGGCCCTTCGGGT
      G  A  P  G  T  P  G  P  Q  G  L  P  G  S  P

BanII          GsuI              StuI           DraIII
      GGGGCTCCGGGTACTCCAGGTCCGCAAGGCCTGCCGGGTTCACCG
      CCCCGAGGCCCATGAGGTCCAGGCGTTCCGGACGGCCCAAGTGGC
      G  A  P  G  T  P  G  P  Q  G  L  P  G  S  P

BglI              BamHI
      GGTGCTCCGGGAACTCCTGGCCCGCAGGGCTTGCCGGGATCCCCA
      CCACGAGGCCCTTGAGGACCGGGCGTCCCGAACGGCCCTAGGGGT
      G  A  P  G  T  P  G  P  Q  G  L  P  G  S  P

GGTGCACCAGGAACGCCGGGAGAAGGTCAACAGCACCATCTTGGT
      CCACGTGGTCCTTGCGGCCCTCTTCCAGTTGTCGTGGTAGAACCA
      G  A  P  G  T  P  G  E  G  Q  Q  H  H  L  G

AatII              BanI
      GGAGCTCGCCAGGCAGGCGACGTCGGTAGCCCTGGTGCC       -3'
      CCTCGAGCGGTCCGTCCGCTGCAGCCATCGGGACCACGG       -5'
      G  A  R  Q  A  G  D  V  G  S  P  (G  A)  (SEQ ID NO:45)
```

PPAS1-B polymer construction

Plasmid DNA from pPTo320 was digested with BanI REN and the digestion fragments were separated by agarose gel electrophoresis. The PPAS1-B gene fragment, 216 bp, was excised and purified using an Ultrafree-MC filter. The purified fragment was ligated with plasmid pPT0317 prepared as described above.

The products of this ligation reaction were transformed into *E. coli* strain HB101. Transformants were selected for resistance to kanamycin. Plasmid DNA from individual transformants was purified and analyzed using EcoRI and EcoRV RENs for DNA inserts containing multimers of the PPAS1-B gene monomer. Several clones were obtained containing inserts up to 5 kb in size.

PPAS1-B expression analysis

*E. coli* strain HB101 containing plasmid pPT0324, containing 10 repeats of the PPAS1-B monomer sequence, was cultured as previously described. The proteins produced by these cells were analysed by western blot for reactivity to CLP antibody. A strong reactive band was observed with an apparent molecular weight of approximately 90 kD.

pPT0324 (SEQ ID NO:31)  PPAS1-B  762 AA  MW  68,336
MDPVVLQRRDWENPGVTQLNRLAAHPPFASDPM
[(GAPGTPGPQGLPGSP)$_3$ GAPGTPGEGQQHHLGGARQAGDVGSP]$_{10}$
GAMDPGRYQDLRSHHHHHH

PPAS1-C gene monomer synthesis and construction

The PPAS1-C amino acid monomer sequence with the fibrin gamma sequence shown in bold is as follows:

(GAPGTPGPQGLPGSP)$_3$GAPGTPGGAKQAGDVGSP (SEQ ID NO:32)

Two oligonucleotide strands (SEQ ID NOS:33–34) (see Table 8) were synthesized and purified as previously described.

TABLE 8

```
5'   TGCACCAGGAACGCCGGGAGGTGCTAAACAAGCAGGAGACGTCGGTAGCCCTGGTGCCTTT
3'            GGTCCTTGCGGCCCTCCACGATTTGTTCGTCCTCTGCAGCCATCGGGACCACGGAAA
```

These oligonucleotide strands were annealed and ligated with plasmid pPT0310 which had been digested with ApaLI and EcoRV RENs. The products of this ligation reaction were transformed into *E. coli* strain HB101. Plasmid DNA from transformants was purified and digested with BsaHI and HindIII RENs to determine their restriction pattern. Plasmid DNA from correct clones was sequenced. Plasmid pPT0319 (shown in Table 9) contained the desired PPAS1-C gene monomer sequence.

TABLE 9

(SEQ ID NO:35)

```
5'-     GGTGCCCCGGGTACTCCTGGTCCACAAGGTCTGCCGGGAAGCCCA
3'-     CCACGGGGCCCATGAGGACCAGGTGTTCCAGACGGCCCTTCGGGT
        G  A  P  G  T  P  G  P  Q  G  L  P  G  S  P

BanII         GsuI               StuI              DraIII
        GGGGCTCCGGGTACTCCAGGTCCGCAAGGCCTGCCGGGTTCACCG
        CCCCGAGGCCCATGAGGTCCAGGCGTTCCGGACGGCCCAAGTGGC
        G  A  P  G  T  P  G  P  Q  G  L  P  G  S  P

BglI              BamHI
        GGTGCTCCGGGAACTCCTGGCCCGCAGGGCTTGCCGGGATCCCCA
        CCACGAGGCCCTTGAGGACCGGGCGTCCCGAACGGCCCTAGGGGT
        G  A  P  G  T  P  G  P  Q  G  L  P  G  S  P

ApaLI
        GGTGCACCAGGAACGCCGGGAGGTGCTAAACAAGCAGGAGACGTC
        CCACGTGGTCCTTGCGGCCCTCCACGATTTGTTCGTCCTCTGCAG
        G  A  P  G  T  P  G  G  A  K  Q  A  G  D  V

BanI
        GGTAGCCCTGGTGCC          -3'
        CCATCGGGACCACGG          -5'
        G   S   P  (G   A) (SEQ ID NO:46)
```

PPAS1-C polymer construction

Plasmid DNA from pPT0319 was digested with BanI REN and the digestion fragments were separated by agarose gel electrophoresis. The PPAS1-C gene fragment, 192 bp, was excised and purified using an Ultrafree-MC filter. The purified fragment was ligated with plasmid pPT0317 which had been prepared as described above. The products of this ligation reaction were transformed into E. coli strain HB101. Transformants were selected for resistance to kanamycin. Plasmid DNA from individual transformants was purified and analyzed using EcoRI and EcoRV RENs for DNA inserts containing multimers of PPAS1-C gene monomer. Several clones were obtained and one of them, pPT0322, containining an insert of approximately 2 kb, containing 10 repeats of the PPAS1-C gene monomer, was chosen for expression analysis.

PPAS1-C expression analysis

E. coli strain HB101 containing plasmid pPT0322 was cultured as previously described. The proteins produced by these cells were analysed by western blot reactivity with CLP antibody. A strong reactive band was observed with an apparent molecular weight of approximately 80 kD.

pPT0322 (SEQ ID NO:36)   PPAS1-C   682 AA   MW 59,192
MDPVVLQRRDWENPGVTQLNRLAAHPPFASDPM
[(GAPGTPGPQGLPGSP)₃ GAPGTPGGAKQAGDVGSP]₁₀
GAMDPGRYQDLRSHHHHHH

PPAS1-D gene monomer synthesis and construction

The PPAS1-D amino acid monomer sequence with the fibrin gamma POLSITE sequence shown in bold is as follows:

(GAPGTPGPQGLPGSP)₂GA TRWYSMKKTTMKIIPFNRLTI

GEGQQHHLGGARQAGDV GSP (SEQ ID NO:38)

One oligonucleotide strand coding for the POLSITE portion of the gene monomer (see Table 10) was synthesized using an Applied Biosystems DNA synthesizer model 381A and a 2000 Å synthesis column supplied by Glen Research. During the synthesis, the required interrupt-pause steps for reagent bottle changes were minimized. After the synthesis, the 126 base DNA strand was deprotected and cleaved from the column support by treatment in ammonium hydroxide at 55° C. for 6 hrs.

TABLE 10

(SEQ ID NO:39)

```
5'-  ATGGCAGCGAAAGGGGACCACCGGGTGCTACCCGTTGGTATTCTATGAAAAAGACTACCATGAA
     AATCATTCCGTTTAACCGCCTGACCATTGGCGAAGGTCAACTTTCCGCTAAAGTCCTGCCGT-3'
```

The PCR reaction was then performed as previously described using the same primers as were used in the construction of the CLP3.7 monomer. The DNA was resuspended and digested with DraIII and HincII RENs and the digested DNA was purified using a Probind filter followed by a Bio-Spin column and then ligated with pPT0320 previously digested with DraIII and HincII RENs and purified with a Probind filter followed by a Bio-Spin column. The products of the ligation reaction were transformed into E. coli strain HB101. Plasmid DNA from transformants was purified and digested with NlaIII and plasmids giving the correct restriction pattern were sequenced. A plasmid containing the desired PPAS1-D monomer sequence, pPT0328, (see Table 11) was used for further DNA constructions.

TABLE 11

(SEQ ID NO:51)

```
  BanI AvaI/SmaI
5'- GGTGCCCCGGGTACTCCTGGTCCACAAGGTCTGCCGGGAAGCCCA
3'- CCACGGGGCCCATGAGGACCAGGTGTTCCAGACGGCCCTTCGGGT
   G  A  P  G  T  P  G  P  Q  G  L  P  G  S  P

BanII          GsuI           StuI          DraIII
GGGGCTCCGGGTACTCCAGGTCCGCAAGGCCTGCCGGGTTCACCG
CCCCGAGGCCCATGAGGTCCAGGCGTTCCGGACGGCCCAAGTGGC
   G  A  P  G  T  P  G  P  Q  G  L  P  G  S  P

GGTGCTACCCGTTGGTATTCTATGAAAAAGACTACCATGAAAATC
CCACGATGGGCAACCATAAGATACTTTTTCTGATGGTACTTTTAG
   G  A  T  R  W  Y  S  M  K  K  T  T  M  K  I

HincII
ATTCCGTTTAACCGCCTGACCATTGGCGAAGGTCAACAGCACCAT
TAAGGCAAATTGGCGGACTGGTAACCGCTTCCAGTTGTCGTGGTA
   I  P  F  N  R  L  T  I  G  E  G  Q  Q  H  H AatII             BanI
CTTGGTGGAGCTCGCCAGGCAGGCGACGTCGGTAGCCCTGGTGCC -3'
GAACCACCTCGAGCGGTCCGTCCGCTGCAGCCATCGGGACCACGG -5'
   L  G  G  A  R  Q  A  G  D  V  G  S  P  (G  A) (SEQ NO:47)
```

PPAS1-D polymer construction pPT0328 plasmid DNA containing the gene monomer coding for PPAS1-D is digested with BanI REN and the digestion fragments are separated by agarose gel electrophoresis. The PPAS1-D gene fragment, 219 bp, is excised and purified using an Ultrafree-MC filter. The purified fragment is ligated with plasmid pPT0317 prepared as described above. The products of this ligation reaction are transformed into E. coli strain HB101. Transformants are selected for resistance to kanamycin. Plasmid DNA from individual transformants is purified and analyzed using EcoRI and EcoRV RENs for DNA inserts containing multimers of the PPAS1-D gene monomer. An approriate clone containing a DNA insert from 1 to 4 kb is analyzed for PPAS1-D polymer expression.

PPAS1-D protein polymer sequence:

MDPVVLQRRDWENPGVTQLNRLAAHPPFASDPM
[(GAPGTPGPQGLPGSP)$_2$ GATRWYSMKKTTMKIIPFNRLTIGEGQQHHLGGARQAGDVGSP]$_n$
GAMDPGRYQDLRSHHHHHH (SEQ ID NO:52)

Where n=2–20

EXAMPLE 5

PPAS1-A Activity Assays

E. coli strain PPT0321 containing the PPAS1-A polymer gene was produced by fermentation. The product was purified from the cellular biomass by means of cellular lysis, clearance of insoluble debris by centrifugation, and affinity chromatography. The purified product was analyzed by sodium dodecyl sulfate polyacrylamide gel electrophoresis, immunoreactivity with CLP antibody, and amino acid analysis. A protein band of apparent molecular weight 85,000 was observed by amido black staining of SDS-PAGE separated and transferred samples and the same band reacted with the CLP antibody on western blots. As expected, amino acid analysis indicated that the product was enriched for the amino acids glycine (34.3%), alanine (7.3%), proline (28.5%), and glutamine (7.0%). The amino acid composition (see Table 12) shows the correlation between the composition of the purified product and the expected theoretical composition as deduced from the synthetic gene sequence.

TABLE 12

Amino Acid Analysis of Purified PPAS1-A

| Amino Acid | pmoles | ACTUAL % composition | THEORETICAL % composition |
|---|---|---|---|
| Ala | 73.74 | 7.3 | 8.4 |
| Asx | 25.57 | 2.5 | 2.3 |
| Glx | 71.11 | 7.0 | 9.7 |
| Phe | 1.48 | 0.15 | 0.1 |
| Gly | 346.27 | 34.3 | 30.5 |
| His | 31.69 | 3.14 | 3.5 |
| Ile | 0 | 0 | 0 |
| Lys | 9.10 | 0.9 | 1.3 |
| Leu | 46.20 | 4.6 | 5.8 |
| Met | 3.83 | 0.38 | 0.4 |

TABLE 12-continued

Amino Acid Analysis of Purified PPAS1-A

| Amino Acid | pmoles | ACTUAL % composition | THEORETICAL % composition |
|---|---|---|---|
| Pro | 288.16 | 28.5 | 24.4 |
| Arg | 4.27 | 0.42 | 0.7 |
| Ser | 48.07 | 4.8 | 5.5 |
| Thr | 47.84 | 4.7 | 5.4 |
| Val | 12.61 | 1.3 | 1.7 |
| Tyr | 0 | 0 | 0.1 |

Purified PPAS1-A was analyzed for its ability to serve as a substrate for the blood clotting enzyme, factor XIIIa. The tests were run in two ways. A plate assay was conducted in which PPAS1-A protein was coated onto the wells of a standard 96-well microtiter plate. Dilutions of PPAS1-A solution were applied into individual wells and allowed to stand overnight at 4 degrees centigrade. Adjacent wells were similarly coated with diluted solutions of the protein B-casein (bovine milk protein, a known substrate for factor XIIIa) or left uncoated as negative controls. After excess coating solution was washed from the wells, a solution containing both factor XIII and thrombin which had been preincubated in order to achieve activation of the factor XIII was applied to each well. Some wells remained free of enzyme solution and served as background controls.

A buffer containing the compound 5-biotinamidopentylamine (BAPA) was also added to each well. BAPA is a substrate analog for factor XIIIa which becomes bonded to a glutamine containing substrate protein via tranglutaminase activity. The reaction of BAPA with B-casein is known to be factor XIIIa dependent. All wells were incubated at 37 degrees centigrade. The wells were washed several times to remove unreacted substrates and enzymes, and filled with a solution containing streptavidin conjugated horse radish peroxidase (streptavidin binds with high affinity to BAPA). The wells were again washed and a solution containing the chromogenic substrate for horse radish peroxidase (HRP) was added. Upon incubation at room temperature, wells began to turn blue. The reaction was stopped by adding 0.1N oxalic acid and the degree of color was quantified by absorbance of light at a wavelength of 410 nm. A color reaction was seen in wells coated with B-casein with the greater color corresponding to the greater concentration of B-casein in the coating solution. Wells containing PPAS1-A also produced a color reaction which increased in intensity with greater PPAS1-A coating concentrations. The PPAS1-A color reaction was dependent on the presence of factor XIIIa, as evidenced from the absence of color in wells lacking factor XIIIa.

A similar assay was run to confirm that the product responsible for the color reaction in the plate assay was indeed PPAS1-A protein. Reactions were conducted in test tubes containing PPAS1-A protein, activated factor XIII, BAPA, and buffer solution. Similar reactions were conducted also with B-casein protein as a control. After incubation at 37 degrees centigrade, samples of the reactions were treated with detergent solution and heated to 100 degrees centigrade for 5 minutes, loaded and electrophoresed on SDS-PAGE gels and transferred to filters. Identical filters were either reacted with streptavidin conjugated horse radish peroxidase or with CLP antibody. The antibody reacted filters were subsequently reacted with horse radish peroxidase conjugated goat anti-immunoglobulin antibody. Both filters were exposed to chemiluminescent reagent substrate for HRP and exposed to X-ray film. Luminescent bands were observed on one panel where BAPA conjugated proteins resided. The B-casein lane contained a band of approximately 24,000 daltons (the expected molecular weight for B-casein). The PPAS1-A lanes contained the polymer bands which correlated with the molecular weight of bands observed on the filter reacted with anti-CLP antibody. The reactivity of these bands was not observed in lanes loaded with reactions in which factor XIIIa had been omitted.

These data indicate that PPAS1-A serves as a substrate for the blood clotting factor XIIIa. The activity observed is consistent with the creation of a covalent bond between PPAS1-A and the substrate analog BAPA. The natural activity of factor XIIIa cross-links two fibrin protein chains by creating an isopeptide bond between a glutamine residue on one chain and a lysine residue on the other. By incorporating the fibrin oligopeptide block containing the active glutamine residue within the PPAS1-A chain, synthetic protein substrate for factor XIIIa was created. In the presence of BAPA or other compounds such as proteins which contain a reactive primary amino group equivalent to lysine, factor XIIIa will cause the linkage of such compounds with PPAS1-A. The activity of such polymers, whether produced by traditional chemical synthesis or recombinant means, and factor XIIIa has utility as an adhesive, sealant, or bonding agent. They may be used in the creation of cross-linked hydrogel materials which can encapsulate live cells, tissues or organs. They may be used to incorporate small molecules or active agents to proteins through nonhydrolyzing but proteolytically susceptible linkages. This chemistry can be used to attach pharmaceuticals to resorbable protein matrices for use in drug delivery.

EXAMPLE 6

Construction of PPAS1-F and PPAS1-G

Plasmid DNA pPT312 was linearized with PvuII REN, then passed through a Millipore Probind filter. The DNA was then treated with SAP. The linearized pPT312 DNA was then ligated with a DNA fragment from pQE-17 (QIAGEN Catalog #33173) prepared as follows. Plasmid DNA pQE-17 was digested with BglII and HindIII RENs and the 36 bp fragment (depicted in Table 5, above) was purified using Probind and Biospin columns as described above. The DNA was purified further using a Microcon 30 column by centrifuging as described above and the filtrate, containing the 36 bp, was kept. The DNA was then treated with DNA Polymerase I and purified through a Probind and then a Biospin column.

The products of the ligation reaction were transformed into E. coli strain HB101. Plasmid DNA from transformants was purified and analyzed by digestion using Bst1107I and EcoRV RENs. Clones containing the desired DNA fragment were further digested with Bst1107I and BstYI RENs to determine the orientation of the insert. Plasmid DNA from the clones showing the correct restriction pattern was purified and analyzed by DNA sequencing. Plasmid pPT0337 contained the desired DNA insert and was used for further DNA manipulation.

Plasmid DNA pPT0337 was digested with XcmI REN, followed by Mung Bean Nuclease treatment for 30 min. at 37° C. The DNA was then purified using Probind and Biospin and then treated with SAP followed by Probind and Biospin column purification.

The PCR amplified DNA, coding for the PPAS1-A (Table 1), was digested with ApaLI and BglII RENs, the fragments were purified by agarose gel electrophoresis followed by Ultrafree MC gel purification. The DNA was then treated with DNA Polymerase I Klenow fragment and then purified using a Probind column followed by a Biospin column as described previously. The DNA was then ligated with pPT0337.

The products of the ligation reaction were transformed into E. coli strain HB101. Plasmid DNA from transformants was purified and analyzed by digestion using EcoRI and DraI RENs. Plasmid pPT0334 contained the desired insert and was used for subsequent constructions.

The PCR amplified DNA coding for PPAS1-A was again digested with EcoRV REN, then the enzyme was removed with a Probind column followed by treatment with BsaJI REN, then purified by Probind and Biospin columns and concentrated in vacuo. The DNA was treated with DNA Polymerase Klenow fragment followed by Probind, the DNA fragments were purified by agarose gel electrophoresis followed by Ultrafree MC gel purification, concentrated in vacuo followed by Biospin. The DNA was then ligated with plasmid DNA pPT334 previously digested with EcoRV REN followed by Probind and Biospin and then treated with SAP followed by Probind and Biospin columns.

The products of the ligation reaction were transformed into *E. coli* strain HB101. Plasmid DNA from transformants was purified and analyzed by digestion using BstXI REN. The clones containing the desired DNA fragment were further digested with AccI and EcoRV RENs to determine the orientation of the insert. Plasmid pPT0338 contained the DNA fragment in the correct orientation and was used for subsequent constructions.

Plasmid DNA pPT0338 was digested with BanI REN and the digestion fragments were separated by agarose gel electrophoresis, the DNA was excised and self-ligated. The products of the ligation mixture were transformed into *E. coli* strain HB101. Plasmid DNA from transformants was purified and analyzed by digestion using BamHI and Bst1107I RENs. Plasmid pPT0339 contained the desired deletion and was used for subsequent constructions.

Plasmid DNA pPT0339 was digested with BanI REN, followed by Probind and Biospin and then treated with SAP followed by Probind and Biospin columns. The plasmid DNA so treated was ligated with the CLP gene fragments from pPT0312. Plasmid DNA pPT0312 was digested with BanI REN and the CLP gene fragments purified by agarose gel electrophoresis followed by NACS and Biospin columns.

The products of this ligation reaction were transformed into *E. coli* strain HB101. Transformants were selected for resistance to kanamycin. Plasmid DNA from individual transformants was purified and analyzed for DNA inserts containing multimers of PPAS1-F gene monomers. Several clones were obtained and one of them (pPT0348) containining an insert of approximately 2.2 kb (12 repeats of the CLP 3.7 gene monomer) was chosen for expression analysis.

PPAS1-F Expression

An overnight culture of *E. coli* strain HB101 containing plasmid pPT0348 grown at 30° C. was used to inoculate 50 ml of LB media contained in a 250 ml flask. Kanamycin was added at a final concentration of 50 µg per ml and the culture was incubated with agitation (200 rpm) at 30° C. When the culture reached an OD$_{600}$ of 0.8, 40 ml were transferred to a new flask prewarmed at 42° C. and incubated at the same temperature for approximately 2 hours. The cultures (30° and 42°) were chilled on ice and OD$_{600}$ was taken. Cells were collected by centrifugation and divided in 1.0 OD$_{600}$ aliquots. The proteins produced by these cells were analysed by western blot reactivity with anti-CLP antibody. A strong reactive band was observed with an apparent molecular weight of approximately 94 kD. The expected amino acid sequence of the PPAS1-F polymer encoded by plasmid pPT0348 is shown below.

fragments from pPT0289. Plasmid DNA pPT0289 (described below) was digested with BanI REN and the SELP8 gene fragments were purified by agarose gel electrophoresis followed by NACS and Biospin columns.

The products of this ligation reaction were transformed into *E. coli* strain HB101. Transformants were selected for resistance to kanamycin. Plasmid DNA from individual transformants was purified and analyzed for DNA inserts containing multimers of PPAS1-G gene monomers. Several clones were obtained and one of them, pPT0349, containining an insert of approximately 2.4 kb (12 repeats of the SELP8 gene monomer) was chosen for expression analysis.

PPAS1-G Expression

An overnight culture of *E. coli* strain HB101 containing plasmid pPT0349 grown at 30° C. was used to inoculate 50 ml of LB media contained in a 250 ml flask. Kanamycin was added at a final concentration of 50 µg per ml and the culture was incubated with agitation (200 rpm) at 30° C. When the culture reached an OD$_{600}$ of 0.8, 40 ml were transferred to a new flask prewarmed at 42° C. and incubated at the same temperature for approximately 2 hours. The cultures (30° and 42°) were chilled on ice and OD$_{600}$ was taken. Cells were collected by centrifugation and divided in 1.0 OD$_{600}$ aliquots. The proteins produced by these cells were analysed by western blot reactivity with anti-SLP antibody. A strong reactive band was observed with an apparent molecular weight of approximately 94 kD. The expected amino acid sequence of the PPAS1-G polymer encoded by plasmid pPT0349 is shown below.

pPT0349  (SEQ ID NO:54) PPAS1-G    877 AA MW 69,941
MDPVVLQRRDWENPGVTQLNRLAAHPPFASDAPGTPGEGQQHHLGGAKQAGDVGSPGAGSGAGAGS
[(GVGVP)$_8$(GAGAGS)$_4$]$_{11}$
(GVGVP)$_8$(GAGAGS)$_2$
GAGAMDPGRYHMAAKGDRAPGTPGEGQQHHLGGAKQAGDVGSPDQDLRSHHHHHH

The fibrin gamma chain sequence is shown in bold.

Protein Polymers as Factor XIII Substrates

PPAS 1-F and PPAS 1-G were determined to be substrates for Factor XIIIa through the use of the Fluoresence Enhancement Assay. Purified lyophilized samples of each polymer were resuspended to 20 mg/ml in reaction buffer (100 mM Tris-HCl pH 7.5, 30 mM NaCl, 1 mM EDTA), from which a 40 µl aliquot was dispensed into a glass test tube. Added to this sample were 120 µl of monodansyl cadavarine (MDC) mix [consisting of 0.55 mg/ml MDC, 73.3 mM Tris-HCl pH 7.5, 40 mM DTT, 18 mM NaCl, and 0.6 mM ethylenediaminetetraacetic acid (EDTA)], 200 µl activated Factor XIII (prepared by incubating 10 µl Factor XIII enzyme preparation with: 146 µl 100 mM Tris-HCl pH 7.5, 30 mM NaCl, 1 mM EDTA; 2.2 µl 100 mM dithiothreitol (DTT); 4 µl Thrombin (1.0 EU/µl) (Calbiochem Cat. #605195) at 37° C. for one hour), and reaction buffer to bring the reaction volume to 1.6 ml. Factor XIII was purified according to the procedure of C. G. Curtis and L. Lorand (Methods in Enzymology 1976, Volume 11, p. 177).

The reaction was incubated at 37° C and progress monitored with periodic florescence measurements on a SequoiapPT0348  (SEQ IN NO:53) PPAS1-F    829 AA MW 72,437
MDPVVLQRRDWENPGVTQLNRLAAHPPFASDAPGTPGEGQQHHLGGAKQAGDVGSP
(GAPGTPGPQGLPGSP)$_{48}$
GAMDPGRYHMAAKGDRAPGTPGEGQQHHLGGAKQAGDVGSPDQDLRSHHHHHH The fibrin gamma chain sequence is shown in bold.

Construction of PPAS1-G

Plasmid DNA pPT0339 prepared as described in the PPAS1-F construction, was ligated with the SELP8 gene Turner model 450 fluorometer blanked against a reaction without Factor XIIIa. The PPAS 1-F and PPAS 1-G proteins, which differ only in the intervening polymer sequences between the N-terminal and C-terminal Factor XIIIa sequences, gave comparable fluorescence readings. After 24 hours of incubation, PPAS 1-F reached a plateau value of 950 FEU and PPAS 1-G of 1125 FEU.

Aliquots of the above reactions were boiled in protein loading buffer for 5 minutes and electrophoresed on an 8% SDS-PAGE gel. Upon separation of the proteins, the gel was illuminated with an ultraviolet lamp and the polymer bands containing the covalently attached MDC flouresced brightly. This provides direct evidence that the measured increase in fluorescence in the reactions was due to Factor XIIIa crosslinking of the protein polymer with the MDC fluorescent marker. These data confirm that the protein polymers PPAS1-G and F are indeed substrates for Factor XIIIa and can be used in crosslinking reactions with suitable amine donors.

Pre-polymerization of Protein Polymers

Lyophilized PPAS 1-F and PPAS 1-G proteins were solubilized for polymerization as follows. Aliquots of 20 mg of each protein were weighed out, dispensed into 1.5 ml Eppendorf tubes and dissolved in 200 Å l of 88% formic acid. The solutions were loaded with a syringe into Pierce Slide-a-lyzers (Pierce Cat. #66425) with a 10K molecular weight cut off. The samples were dialyzed at 22° C. for 24 hours versus 4 liters of 100 mM Tris-HCl pH7.5; 30 mM NaCl; 1 mM EDTA. Upon completion of the dialysis the samples were removed from the Slide-a-lyzers, microfuged to remove any particulates, and analyzed by Lowry assay to determine the polymer concentration remaining in solution. The concentration of PPAS 1-F was 9.6 mg/ml while that of PPAS 1-G was 16.2 mg/ml.

The polymers were prepared for crosslinking by aliquoting 20 $\mu$l of either PPAS 1-F or PPAS 1-G into 0.5 ml Eppendorf tubes. To these tubes 5 $\mu$l of activated Factor XIII (prepared by incubating 10 $\mu$l Factor XIII with: 110 $\mu$l 100 mM Tris-HCl pH 7.5, 30 mM NaCl, 1 mM EDTA; 2.2 $\mu$l 100 mM DTT; 4 $\mu$l Thrombin (1.0 EU/$\mu$l) (Calbiochem Cat. 605195) at 37° C. for one hour) was added and the reaction was incubated at 37° C. for 24 hours. Samples of the crosslinking reaction were boiled in protein loading buffer 5 minutes and loaded on a 4–12% gradient SDS-PAGE. After separation of the protein bands, the gel was electroblotted onto a nitrocellulose filter and a Western blot was performed using anti-CLP antibody for PPAS 1-F and anti-SLP antibody for PPAS 1-G. The results showed a polymerization of each polymer stepwise forming a ladder of discrete bands which corresponded in size to multimers of the unit polymer molecular weight. PPAS 1-F multimerized to four polymers in length with a predicted molecular weight of 290 Kd, while PPAS 1-G showed banding to sixteen times the unit polymer in length indicating a molecular weight of 1119 Kd. Additionally, the PPAS 1-G lane had immunoreactive material which migrated at the interface of the stacking and resolving gels as well as material which was trapped in the well indicating the presence of even larger molecular weight products. Finally, a reaction containing equal weights of both PPAS 1-F and PPAS 1-G polymers resulted in banding to nine times the unit polymer size with the products reactive to both antibodies. This indicates the ability of the polymers to cross-link to non-self as well as identical molecules.

Rat Skin Lap-Shear Adhesion Assay with PPAS1-G

PPAS1-G was selected for testing in the lap pull assay. The protein sample was prepared for testing as described in the solubilization protocol for pre-polymerization. After dialysis versus water, the PPAS 1-G was concentrated in a Speed-vac under vacuum until a volume was reached which corresponded to a polymer concentration of 100 mg/ml. The polymer was a clear, viscous solution at this point. The polymer was pre-polymerized with Factor XIIIa to maximize the size of the individual protein species. This was accomplished by incubating 90 $\mu$l 100 mg/ml PPAS 1-G in 100 mM HEPES pH 7.5, 30 mM NaCl; 50 mM CaCl$_2$, 2 mM DTT, in a final volume of 300 $\mu$l which included 30 $\mu$l of Factor XIII and 15 $\mu$ Thrombin (1 EU/$\mu$l) (Calbiochem Cat. #605195) for 20 hours at 37° C. After this initial crosslinking step the reaction mixture was concentrated threefold in a Speed-vac to a volume of 100 $\mu$l and a polymer concentration of 90 mg/ml. To this was added 1.5 $\mu$l 100 mM DTT, 18.5 $\mu$l H$_2$O, and 30 $\mu$l Factor XIII, bringing the volume to 150 $\mu$l. Three 50 $\mu$l aliquots were dispensed into 3–500 $\mu$l Eppendorf tubes containing 3 $\mu$l of Thrombin, mixed well and applied between a 1 cm square overlap of rat skin. The skins were weighted to 100 g each and allowed to cure at 37° C. for 2 hours. The skins were then mounted on a mechanical testing apparatus and a continually increasing force was applied in tension until the joint between the two skins failed. The average weight required to cause failure of the three replicate pulls was 92.9 g/cm$^2$, which is significantly greater than a control of 22.8 g/cm$^2$ which consisted of PPAS 1-G without Factor XIII.

EXAMPLE 7

Construction of SELP8K and SELP8E

Polymers were prepared designated SELP8K and SELP8E, which are characterized by having functional groups for linking side chains containing reactive amino acids for transglutaminase cross-linking. The construction of these polymers is described below starting from the previous gene monomer, SELPO (see U.S. Pat. No. 5,243,038, pSY1298).

SELP8K (SEQ ID NO:55) and SELP8E (SEQ ID NO:56) amino acid monomer sequence design:

SELP8K MONOMER (GAGAGS)$_4$ (GVGVP)$_4$ GKGVP (GVGVP)$_3$
SELP8E MONOMER (GAGAGS)$_4$ (GVGVP)$_4$ GEGVP (GVGVP)$_3$

SELP8 construction

Plasmid pSY1378 (see U.S. Pat. No. 5,243,038) was digested with BanI REN, purified using agarose gel electrophoresis followed by NACS column, and the DNA was then ethanol precipitated in 2.5M ammonium acetate and ligated with pPT0134 (See PCT/US92/09485) previously digested with FokI REN, phenol/chloroform extracted and ethanol precipitated.

The products of the ligation mixture were transformed into E. coli strain HB101. Plasmid DNA from transformants was purified and analyzed by digestion using NruI and XmnI RENs. Plasmid pPT0255 containing the desired restriction pattern was obtained and was used for subsequent constructions.

Plasmid DNA pPT0255 was treated with Cfr10I REN followed by RNAse. The digestion fragments were separated by agarose gel electrophoresis, the DNA was excised and self-ligated. The products of the ligation mixture were transformed into E. coli strain HB101. Plasmid DNA from transformants was purified and analyzed by digestion using NaeI and StuI RENs. Plasmid pPT0267 containing the desired deletion was used for subsequent constructions.

Two olgonucleotide strands as shown in Table 13 were synthesized and purified as described in Example 1.

TABLE 13

5'-     CTGGAGCGGGTGCCTGCATGTACATCCGAGT -3' (SEQ ID NO:57)
3'- CCGAGACCTCGCCCACGGACGTACATGTAGGCTCA -5' (SEQ ID NO:58)

The two oligonucleotide strands were annealed and ligated with the DNA of plasmid pPT0267 which had been previously digested with BanII and ScaI RENs, and purified by agarose gel elctrophoresis followed by NACS column.

The products of this ligation reaction were transformed into E. coli strain HB101. Plasmid DNA from transformants was purified and digested with DraI. Plasmid DNA from two clones that gave the correct digestion pattern was sequenced. One plasmid DNA, designated pPT0287, was found to be correct and chosen for further constructions.

SELP8 gene monomer was synthesized with a single base polymorphism at position 90. The use of both adenine and guanidine at this position produced oligonucleotides from a single synthesis that encoded the amino acids lysine and glutamic acid (see Table 15). The synthesis was conducted using an Applied Biosystems DNA synthesizer model 381A and a 2000 Å synthesis column supplied by Glen Research. During the synthesis the required interrupt-pauses for bottle changes were minimized. After the synthesis the 202 base DNA fragment was deprotected and cleaved from the column support by treatment in 30% ammonium hydroxide at 55° C. for 6 hrs.

TABLE 15

(SEQ ID NO:61)

5
ATGGCAGCGAAAGGGGACCGGGCTCTGGTGTTGGAGTGCCAGGTGTCGGTGTTCCGGGTGTAGGCGTTC
CGGGAGTTGGTGTACCTGGA(A/G)AAGGTGTTCCGGGGGTAGGTGTGCCGGGCGTTGGAGTACCAGGT
GTAGGCGTCCCGGGAGCGGGTGCTGGTAGCGGCGCAGGCGCGGGCTCTTTCCGCTAAAGTCCTGCCGT-3'

Plasmid DNA pSY1298 (see U.S. Pat. No. 5,243,038) was digested with BanII REN, and the SELP0 gene fragment was purified by agarose gel electrophoresis followed by NACS and then ligated to pPT0287 digested with BanII. The enzyme was then removed using phenol/chloroform extraction and ethanol precipitation.

The products of the ligation mixture were transformed into E. coli strain HB101. Plasmid DNA from transformants was purified and analyzed by digestion using DraI REN. Plasmid DNA from the clones showing the correct restriction pattern was further digested with BanII, AhaII and StuI RENs. Plasmid pPT0289 contained the desired SELP8 monomer sequence (see Table 14).

Two additional DNA strands were used as primers for PCR amplification. The two strands were:

1. 5'-AAGAAGGAGATATCATATGGCAGCGAAAGGGGACC-3' (SEQ ID NO:62)

2. 5'-CGCAGATCTTTAAATTACGGCAGGACTTTAGCGGAAA-3' (SEQ ID NO:63)

The PCR reaction was carried out and the reaction product was purified as described in Example 1.

The DNA was resuspended and digested with BanII REN as described in Example 1. The digested DNA was then separated by low-melting agarose gel electrophoresis and ligated with pPT0289 previously digested with BanII RENs

TABLE 14

SELP8 Gene Monomer Sequence
(SEQ ID NO:59)

```
BanI                                     BanII
GGT GCC GGT TCT GGA GCT GGC GCG GGC TCT GGA GTA GGT GTG CCA GGT
CCA CGG CCA AGA CCT CGA CCG CGC CCG AGA CCT CAT CCA CAC GGT CCA
G   A   G   S   G   A   G   A   G   S   G   V   G   V   P   G

GTA GGA GTT CCG GGT GTA GGC GTT CCG GGA GTT GGT GTA CCT GGA GTG

CAT CCT CAA GGC CCA CAT CCG CAA GGC CCT CAA CCA CAT GGA CCT CAC
V   G   V   P   G   V   G   V   P   G   V   G   V   P   G   V

SmaI
GGT GTT CCA GGC GTA GGT GTG CCC GGG GTA GGA GTA CCA GGG GTA GGC
CCA CAA GGT CCG CAT CCA CAC GGG CCC CAT CCT CAT GGT CCC CAT CCG
G   V   P   G   V   G   V   P   G   V   G   V   P   G   V   G

BanII
GTC CCT GGA GCG GGT GCT GGT AGC GGC GCA GGC GCG GGC TCT GGA GCG
CAG GGA CCT CGC CCA CGA CCA TCG CCG CGT CCG CGC CCG AGA CCT CGC
V   P   G   A   G   A   G   S   G   A   G   A   G   S   G   A
```

(SEQ ID NO:60)

Contruction of SELP8K and SELP8E Gene Monomers

One oligonucleotide strand coding for a portion of the and purified by NACS column. The products of the ligatoin reaction were transformed into E. coli strain HB101. Plasmid DNA from isolated transformants was purified and analyzed by digestion using ApaLI, and EcoNI RENs. Plasmid DNA from the clones showing the correct restriction pattern were further analyzed by digestion using Asp7OO REN to distinguish between clones encoding a lysine or glutamic acid at the polymorphic position. Plasmid DNA from clones containing each of the polymorphs was purified and analyzed by DNA sequencing. Plasmid pPT0340 contained the desired SELP8K monomer sequence and pPT0350 contained the desired SELP8E monomer sequence (see Tables 16 and 17).

transformants was purified and analyzed for increase size due to SELP8K monomer multiple DNA insertion. Several clones were obtained with insert sizes ranging from 200 bp to approximately 7 kb. Clones containining from 6 to 32 repeats, were used for expression of the SELP8K protein polymer (pPT0341, pPT0343, pPT0344, pPT0345 and pPT0347).

SELP8K Expression Analysis

An overnight culture which had been grown at 30° C. was used to inoculate 50 ml of LB media contained in a 250 ml flask. Kanamycin was added at a final concentration of 50 μg

TABLE 16

SELP8K Gene Monomer Sequence (SEQ ID NO:64)

```
BanI                              BanII
GGT GCC GGT TCT GGA GCT GGC GCG GGC TCT GGT GTT GGA GTG CCA GGT
CCA CGG CCA AGA CCT CGA CCG CGC CCG AGA CCA CAA CCT CAC GGT CCA
G   A   G   S   G   A   G   A   G   S   G   V   G   V   P   G

EcoNI
GTC GGT GTT CCG GGT GTA GGC GTT CCG GGA GTT GGT GTA CCT GGA AAA
CAG CCA CAA GGC CCA CAT CCG CAA GGC CCT CAA CCA CAT GGA CCT TTT
V   G   V   P   G   V   G   V   P   G   V   G   V   P   G   K

GGT GTT CCG GGG GTA GGT GTG CCG GGC GTT GGA GTA CCA GGT GTA GGC
CCA CAA GGC CCC CAT CCA CAC GGC CCG CAA CCT CAT GGT CCA CAT CCG
G   V   P   G   V   G   V   P   G   V   G   V   P   G   V   G

SmaI                                     BanII
GTC CCG GGA GCG GGT GCT GGT AGC GGC GCA GGC GCG GGC TCT GGA GCG
CAG GGC CCT CGC CCA CGA CCA TCG CCG CGT CCG CGC CCG AGA CCT CGC
V   P   G   A   G   S   G   A   G   S   G   A
(SEQ ID NO:65)
```

TABLE 17

SELP8E Gene Monomer Sequence (SEQ ID NO:66)

```
BanI                              BanII
GGT GCC GGT TCT GGA GCT GGC GCG GGC TCT GGT GTT GGA GTG CCA GGT
CCA CGG CCA AGA CCT CGA CCG CGC CCG AGA CCA CAA CCT CAC GGT CCA
G   A   G   S   G   A   G   A   G   S   G   V   G   V   P   G

EcoNI
GTC GGT GTT CCG GGT GTA GGC GTT CCG GGA GTT GGT GTA CCT GGA GAA
CAG CCA CAA GGC CCA CAT CCG CAA GGC CCT CAA CCA CAT GGA CCT CTT
V   G   V   P   G   V   G   V   P   G   V   G   V   P   G   E

Asp700
GGT GTT CCG GGG GTA GGT GTG CCG GGC GTT GGA GTA CCA GGT GTA GGC
CCA CAA GGC CCC CAT CCA CAC GGC CCG CAA CCT CAT GGT CCA CAT CCG
G   V   P   G   V   G   V   P   G   V   G   V   P   G   V   G

SmaI                                     BanII
GTC CCG GGA GCG GGT GCT GGT AGC GGC GCA GGC GCG GGC TCT GGA GCG
CAG GGC CCT CGC CCA CGA CCA TCG CCG CGT CCG CGC CCG AGA CCT CGC
V   P   G   A   G   S   G   A   G   S   G   A
(SEQ ID NO:67)
```

SELP8K Polymer Construction

Plasmid DNA from pPT0340 was digested with BanI REN and the digestion fragments were separated by agarose gel electrophoresis. The SELP8K gene fragment, 192 bp, was excised and purified by NACS column. The purified fragment was ligated with plasmid pPT0317 which had been digested with BanI REN, passed through a Millipore Probind and a Bio-Spin 6 column. The DNA was then treated with shrimp alkaline phosphatase (SAP) as described in Example 1.

The products of this ligation reaction were transformed into E. coli strain HB101. Transformants were selected for resistance to kanamycin. Plasmid DNA from individual per ml and the culture was incubated with agitation (200 rpm) at 30° C. When the culture reached an $OD_{600}$ of 0.8, 40 ml were transferred to a new flask prewarmed at 42° C. and incubated at the same temperature for approximately 2 hours. The cultures (30° and 42°) were chilled on ice and $OD_{600}$ was taken. Cells were collected by centrifugation and divided in 1.0 $OD_{600}$ aliquots and used to perform western analysis using anti-SLP antibody.

E. coli strain HB101 containing plasmids pPT0341, pPT0343, pPT0344, pPT0345 and pPT0347 were grown as described above. The proteins produced by these cells were analysed by Western blot for detection of proteins reactive to SLP antibodies. Each clone produced a strongly reactive band. The apparent molecular weights of the products ranged from approximately 35kD to greater than 250 kD. Strain pPT0345 produced an SLP antibody reactive band of apparent molecular weight 80,000. The expected amino acid sequence of the SELP8K polymer encoded by plasmid pPT0345 is shown below.

pPT0345 (SEQ ID NO:68) SELP8K 884 AA MW 69,772
MDPVVLQRRDWENPGVTQLNRLAAHPPFASDPMGAGSGAGAGS
[(GVGVP)₄GKGVP (GVGVP)₃(GAGAGS)₄]₁₂
(GVGVP)₄GKGVP (GVGVP)₃(GAGAGS)₂
GAGAMDPGRYQDLRSHHHHHH

SELP8K Purification

SELP8K was produced in *E. coli* strain pPT0345 by fermentation. The product was purified from the cellular biomass by means of cellular lysis, clearance of insoluble debris by centrifugation, and affinity chromatography. The purified product was analyzed by sodium dodecyl sulfate polyacrylamide gel electrophoresis, immunoreactivity with a polyclonal antisera which reacts with silk-like peptide blocks (SLP antibody), and amino acid analysis. A protein band of apparent molecular weight 80,000 was observed by amido black staining of SDS-PAGE separated and transfered samples and the same band reacted with the SLP antibody on Western blots. As expected, amino acid analysis (shown in Table 18) indicated that the product was enriched for the amino acids glycine (43.7%), alanine (12.3%), serine (5.3%), proline (11.7%), and valine (21.2%). The product also contained 1.5% lysine. The amino acid composition table below shows the correlation between the composition of the purified product and the expected theoretical compositions as deduced from the synthetic gene sequence.

TABLE 18

Amino Acid Analysis of Purified SELP8K

| Amino Acid | pmoles | ACTUAL % composition | THEORETICAL % composition |
|---|---|---|---|
| Ala | 1623.14 | 12.3 | 12.2 |
| Asx | 122.20 | 0.9 | 0.8 |
| Glx | nd | nd | 0.4 |
| Phe | 58.16 | 0.4 | 0.1 |
| Gly | 5759.31 | 43.7 | 41.5 |
| His | 46.75 | 0.4 | 0.8 |
| Ile | 43.87 | 0.3 | 0 |
| Lys | 198.21 | 1.5 | 1.5 |
| Leu | 39.54 | 0.3 | 0.5 |
| Met | 36.01 | 0.3 | 0.3 |
| Pro | 1534.21 | 11.7 | 12.4 |
| Arg | 70.84 | 0.5 | 0.6 |
| Ser | 703.83 | 5.3 | 6.1 |
| Thr | nd | nd | 0.1 |
| Val | 2797.47 | 21.2 | 22.4 |
| Tyr | 140.87 | 1.1 | 0.1 | nd = none detected

Construction of Peptide/Protein Polymer Adhesive Conjugates

The construction of peptide/protein polymer conjugates that would function as substrates for Factor XIII crosslinking began with a screen of potential peptide sequences with known activities for Factor XIII. Several peptide sequences were tested before settling on a sequence, K9, first disclosed by Fickenscher et al. (Thromb. Haemostas 1991, 5, p. 535–540). Peptides were purified using reverse phase HPLC and analyzed by mass spectroscopy.

Pep94.5 (SEQ ID NO:69)LGPGQSKVIG—NH₂ PPTpep0016

This sequence was further modified to enable conjugation and characterization of the degree of substitution of the final conjugate.

Pep94.14 (SEQ ID NO:70) Ac—C(nle)LGPGQSKVIG—NH₂ PPTpep0017

The cysteine was added to functionalize the peptide for conjugation. The norleucine (nle) was added as a label to determine the number of peptides in the final conjugate.

The glutamine in this peptide is the site for Factor XIII-mediated crosslinking with an amine donor. A review of the literature disclosed lysine containing peptide sequences which were found to be especially active amine donors for Factor XIII. (J. E. Folk (1983) Adv. Enzymo. 54, p. 1–56).

Pep94.11 (SEQ ID NO:71) GGLKGGG PPTpep0020

This sequence was similarly modified as for Pep94.11 to enable conjugation and characterization.

Pep94.13 (SEQ ID NO:72) C(nle)GGLKGGG PPTpep0021

Table 19

Mass Spectrometry of Peptides Synthesized

| Peptide | Theoretical Molecular Weight | Mass Spec Molecular Weight |
|---|---|---|
| P94.5 | 954.11 | 953.7 |
| P94.14 | 1212.4 | 1212.9 |
| P94.11 | 544.59 | 545.8 |
| P94.13 | 760.89 | 762.2 |

These peptides were conjugated to the protein polymer, SELP8K which was specifically designed to be functionalized with different reagents reactive to amines. A bifunctional crosslinker, Sulfo-GMBS (N-(γ-maleimidobutryloxy) sulfosuccinimide ester), purchased from Pierce Chemical Company (catalog # 22324) was used to graft the peptides to the SELP8K protein polymer.

C95.1, polymer/peptide conjugate containing the lysine donor peptide [SELP8K P94.13 (PPTpepOO21)] was synthesized as follows. Prior to the reaction, two 10 ml Presto columns (Pierce Chemical Company) were each equilibrated with 100 mls of 20 mM NaPO₄ (pH 7.0), 100 mM NaCl. 70 mg of purified SELP8K was brought up to 6 mls with 20 mM NaPO₄ (pH 7.0), 100 mM NaCl. The solution was vortexed. 50 mg of Sulfo-GMBS was added slowly to the polymer solution while stirring. A yellow color developed. The reaction was allowed to proceed while stirring for 30 min at room temperature. Half of the reaction was chromatographed over each Presto column and eluted with 20 mM NaPO₄ (pH 7.0), 100 mM NaCl. 1 ml fractions were collected. Fractions containing the derivatized polymer were pooled.

20 mg of Pep94.13 was added slowly to the above pooled fractions. The mixture was stirred for 16 hours at room temperature. 100 μl of β-mercaptoethanol was added to stop the reaction. The reaction was dialyzed in a 3500 molecular weight cut off dialysis bag against three changes of four liters of deionized water. The dialyzed solution was lyophilized.

C95.2, the polymer/peptide conjugate containing the glutamine donor peptide[SELP8K Pep94.14 (PPTpepOO17)] was synthesized exactly as C95.1 except that 25 mg of Pep94.14 was added to the Sulfo-GMBS derivatized SELP8K polymer.

TABLE 20

Amino Acid Analysis of C95.1

| Name | C95.1 Actual AA composition (pmoles) | p94.13 Theoretical AA composition (# of residues) | c95.1-94.13 Calculated AA composition (pmoles) | SELP8K Theoretical AA composition (# of residues) | Peptides per Conjugate |
|---|---|---|---|---|---|
| ASX | 41.00 |   | 41.00 | 7 |   |
| GLX | 40.00 |   | 40.00 | 4 |   |
| SER | 375.00 |   | 375.00 | 54 |   |
| GLY | 2826.00 | 5 | 2336.00 | 367 | 15.40 |
| HIS | 36.00 |   | 36.00 | 7 |   |
| ARG | 25.00 |   | 25.00 | 5 |   |
| THR | 0.00 |   | 0.00 | 1 |   |
| ALA | 778.00 |   | 778.00 | 108 |   |
| PRO | 694.00 |   | 694.00 | 110 |   |
| TYR | 10.00 |   | 10.00 | 1 |   |
| VAL | 1237.00 |   | 1237.00 | 198 |   |
| MET | 26.00 |   | 26.00 | 3 |   |
| ILE | 0.00 |   | 0.00 | 0 |   |
| LEU | 113.00 | 1 | 15.00 | 4 |   |
| NLE | 98.00 | 1 | 0.00 | 0 |   |
| PHE | 14.00 |   | 14.00 | 1 |   |
| LYS | 189.00 | 1 | 91.00 | 13 | 14.00 |
|   |   |   |   | Average | 14.70 |
|   |   |   |   | Stdev | 0.99 |

This analysis indicates that conjugatre C95.1 contains an average of 14.7 peptides per SELP8K polymer molecule. This is greater than the number of lysines present in the polymer (13).

TABLE 21

Amino Acid Compositional Analysis of C95.2

| Name | C95.2 (pmoles) | P94.14 Theoretical AA Composition (# of residues) | C95.2-P94.14 Calculated AA Composition (pmoles) | SELP8K Theoretical AA Composition (# of residues) | Peptides per Conjugate |
|---|---|---|---|---|---|
| ASX | 29.00 |   | 29.00 | 7 |   |
| GLX | 89.00 | 1 | 28.00 | 4 |   |
| SER | 392.00 | 1 | 331.00 | 54 | 9.95 |
| GLY | 2112.00 | 3 | 1929.00 | 367 | 11.61 |
| HIS | 27.00 |   | 27.00 | 7 |   |
| ARG | 24.00 |   | 24.00 | 5 |   |
| THR | 0.00 |   | 0.00 | 1 |   |
| ALA | 636.00 |   | 636.00 | 108 |   |
| PRO | 638.00 | 1 | 577.00 | 110 | 11.63 |
| TYR | 8.00 |   | 8.00 | 1 |   |
| VAL | 1063.00 | 1 | 1002.00 | 198 | 12.05 |
| MET | 8.00 |   | 8.00 | 3 |   |
| ILE | 52.00 | 1 | −9.00 | 0 |   |
| LEU | 78.00 | 1 | 17.00 | 4 |   |
| NLE | 61.00 | 1 | 0.00 | 0 |   |
| PHE | 12.00 |   | 12.00 | 1 |   |
| LYS | 140.00 | 1 | 79.00 | 13 | 10.04 |
|   |   |   |   | Average | 11.06 |
|   |   |   |   | Stdev | 0.99 |

This analysis indicates that conjugate C95.2 contains an average of 11.1 peptides per SELP8K polymer molecule.

The two conjugates C95.1 and C95.2 were used in an adhesive formulation to test their ability to bond skin together. The formulation was produced by placing 5.7 mg of each conjugate in a 1.5 ml eppendorf tube. 58 μl of deionized water was added and the tube vortexed for 5 min. 5.8 μl of 1M HEPES (pH 7.5), 300 mM NaCl, 6 41 of 100 mM dithiothreitol, 26.8 μl of Factor XIII, and 10.5 μl of 500 mM $CaCl_2$ was added and the solution vortexed. 35 μl aliquots were placed in individual tubes.

Just prior to application to skins, 3μl of Thrombin, 1 unit/μl (Calbiochem #605195, 100 units brought up to 100 μg with enzyme dilution buffer: 50% glycerol, 6.67 mM DTT, 10 mM Tris-HCl pH 7.5) was added to each aliquot. The solution was mixed briefly and applied to a 1 $cm^2$ area at one end of the subcutaneous face of a 1 cm×3 cm strip of rat skin. Another skin strip was overlayed such that a lap over area of 1 $cm^2$ was produced between the two skins. The skins were wrapped in plastic wrap placed at 37° C. with a weight of 100 grams placed on them. At a specified cure time the skins were brought to room temperature and promptly pulled apart to measure the shear strength of the lapped bond.

The solution was fluid before application to skins. It flowed easily over the skins and wetted the skin surface thoroughly. After several minutes at 37° C., the material set as evidenced by the formation of a strong, flexible solid material. The crosslinked adhesive formulation also has utility as a firm, hydrogel material which can be used for medical devices such as contact lenses or as a time released drug delivery system.

TABLE 22

Rat Skin Lap-Shear Adhesive Assay

| Test Conditions | Test A | Test B | Test C | Average Bond Strength (Grams/$cm^2$) | Stdev |
|---|---|---|---|---|---|
| 5 min. cure @ 37° C. | 190 g | 300 g | * | 245.0 | 77.8 |
| Lap Area | 1.0 $cm^2$ | 1.2 $cm^2$ |   |   |   |
| 30 min. cure @ 37° C. | 477 g | 900 g | 1078 g | 818.3 | 308.7 |
| Lap Area | 0.96 $cm^2$ | 1.2 $cm^2$ | 1.3 $cm^2$ |   |   |

* Sample gelled in tube before application to skins

EXAMPLE 9

Additional PPAS designs incorporating non-fibrin derived crosslinking sequences.

PPAS2 Constructions

The results obtained from the above examples prove that sequences from natural proteins which serve as substrates for enzymatic crosslinking can be incorporated into novel polymeric protein-based substrates which function in the same capacity. They can either be conjugated to protein carriers thereby allowing their density per molecule to be controlled or incorporated within a protein polymer allowing additional control over their distribution along the chain.

These results can be expanded to include sequences or molecules that are modified over natural sequences by amino acid substitutions or chemical modifications for purposes of increasing their overall catalytic activity toward the crosslinking enzyme. The scientific literature demonstrates that sequence modified peptides can result in 2–10 fold improvements in catalytic activity by either increasing their affinity for the enzyme, increasing the enzyme's turnover number, or both.

The ability to utilize peptides in the construction of polymeric protein adhesive substrates that are synthetically designed or chemically modified to optimize their crosslinking activity with Factor XIII or other transglutaminases is further exemplified by the following examples.

PPAS2-A(SEQ ID NO:73): Lysine donor polymer dispersed throughout SELP8 backbone

MDPVVLQRRDWENPGVTQLNRLAAHPPFASDPMGAGSGAGAGS
[(GVGVP)$_4$G GGLKGGG GVP (GVGVP)$_3$(GAGAGS)$_4$]$_n$
(GVGVP)$_4$G GGLKGGG GVP (GVGVP)$_3$(GAGAGS)$_2$
GAGAMDPGRYQDLRSHHHHHH

Where n=2–20. Crosslinking sequences shown in bold.

PPAS2-B: (SEQ ID NO:74) Glutamine (K9) donor dispersed throughout SELP8 backbone MDPVVLQRRDWENPGVTQLNRLAAHPPFASDPMGAGSGAGAGS
[(GVGVP)$_4$G LGPGQSKVIG GVP (GVGVP)$_3$(GAGAGS)$_4$]$_n$
(GVGVP)$_4$G LGPGQSKVIG GVP (GVGVP)$_3$(GAGAGS)$_2$
GAGAMDPGRYQDLRSHHHHHH Where n=2–20. Crosslinking sequences shown in bold.

PPAS2-C: (SEO ID NO:75) Lysine donor contained only at ends of SELP8 backbone

MDPVVLQRRDWENPGVTQLNRLAAHPPFASDAPGTP GGLKGGG GSPGAGSGAGAGS
[(GVGVP)$_8$(GAGAGS)$_4$]$_n$
(GVGVP)$_8$(GAGAGS)$_2$
GAGAMDPGRYHMAAKGDRAPGTP GGLKGGG GSPDQDLRSHHHHHH

Where n=2–20. Crosslinking sequences shown in bold.

PPAS2-D: (SEO ID NO:76) Glutamine (K9) donor contained only at ends of SELP8 backbone MDPVVLQRRDWENPGVTQLNRLAAHPPFASDAPGTPLGPGQSKVIGGSPGAGSGAGAGS
[(GVGVP)$_8$(GAGAGS)$_4$]$_n$
(GVGVP)$_8$(GAGAGS)$_2$
GAGAMDPGRYHMAAKGDRAPGTP LGPGQSKVIG GSPDQDLRSHHHHHH Where n=2–20. Crosslinking sequences shown in bold.

PPAS2-E: (SEQ ID NO:77) Glutamine (K9) and Lysine donor (contained only at ends of SELP8 backbone)

MDPVVLQRRDWENPGVTQLNRLAAHPPFASDAPGTP GGLKGGG GSPGAGSGAGAGS
[(GVGVP)$_4$G LGPGQSKVIG GVP (GVGVP)$_3$(GAGAGS)$_4$]$_n$
(GVGVP)$_4$G LGPGQSKVIG GVP (GVGVP)$_3$(GAGAGS)$_2$
GAGAMDPGRYHMAAKGDRAPGTP GGLKGGG GSPDQDLRSHHHHHH

Where n=2–20. Crosslinking sequences shown in bold.

PPAS2-F: (SEO ID NO: 79)Mixed Glutamine (K9) and Lysine donor (dispersed throughout SELP8 backbone)

MDPVVLQRRDWENPGVTQLNRLAAHPPFASDPMGAGSGAGAGS
[(GVGVP)$_4$G LGPGQSKVIG GVP (GVGVP)$_3$(GAGAGS)$_4$(GVGVP)$_4$G GGLKGGG GVP (GVGVP)$_3$(GAGAGS)$_4$]$_n$
(GVGVP)$_4$G LGPGQSKVIG GVP (GVGVP)$_3$(GAGAGS)$_4$(GVGVP)$_4$G GGLKGGG GVP (GVGVP)$_3$(GAGAGS)$_2$
GAGAMDPGRYQDLRSHHHHHH

Where n=2–20. Crosslinking sequences shown in bold.

It is apparent to someone skilled in the art that an endless number of combinations and arrangments of glutamine donor, lysine donor, and structural protein blocks can be made in order to improve the crosslinking of the polymeric substrates and the properties of the adhesives which they comprise. For example, adjustments in the stoicheometric number and ratio of active sites may change the overall crosslink density and cohesive strength of the crosslinked protein matrix and change its susceptibility to degradation when placed in or on the body. Increasing the ratio of glutamine donor sites to lysine donor sites may improve the adhesive bond strength by increasing the probability of polymer crosslinking with tissue proteins containing lysine donors.

Additional peptide sequences can be used in place of the sequences shown above. A list of examples are shown below. Subsequences of the examples shown may also be sufficient for activity. The sequences shown may also be extended with amino acids on either end to improve their utility, for example, multiple glycine tails may be added to improve the sequence's accessibility to the active site of the enzyme.

| Glutamine Donors | Lysine Donors |
| --- | --- |
| GQQHHLGG (SEQ ID NO:80) | XKZ, where X = L, S, A, K, R, andZ = G, V, H, but |

-continued

| Glutamine Donors | Lysine Donors |
| --- | --- |
| | X ≠ P, G, and Z ≠ P |
| SVLSLSQSKVLPVPE (SEQ ID NO:81) | PXKZ, where X = L, S, A, K, R, and Z = G, V, H, but |

-continued

| Glutamine Donors | Lysine Donors |
|---|---|
| | X ≠ P, G, and Z ≠ P |
| SVLSLSQSRVLPVPE | GPXKZ, where X = L, S, A, |
| (SEQ ID NO:82) | K, R, and Z = G, V, H, but |
| | X ≠ P, G, and Z ≠ P |
| CVLSLSQSRVLVPEC | PGXKZG, where X = L, S, |
| (SEQ ID NO:83) | A, K, R, and Z = G, V, H, |
| | but X ≠ P, G, and Z ≠ P |
| SVLSGSQSKVLPVPE (SEQ ID NO:84) | RRSKHIS (SEQ ID NO:85) |
| CLGPGQSKVIGC (SEQ ID NO:86) | AKKKRS (SEQ ID NO:87) |
| LSLSQSKVLG (SEQ ID NO:88) | AHKKGQ (SEQ ID NO:89) |
| LGPGQSRVIG (SEQ ID NO:90) | YLKDQQ (SEQ ID NO:91) |
| LGPGQHKVIG (SEQ ID NO:92) | PTTKMA (SEQ ID NO:93) |
| LGPGQHRVIG (SEQ ID NO:94) | RLDHKF (SEQ ID NO:95) |
| CLGPGQSRVIGC (SEQ ID NO:96) | VGSNKGA (SEQ ID NO:97) |
| GGPGQSKVIGG (SEQ ID NO:98) | |
| NQEQVSPLT (SEQ ID NO:99) | |
| TDMPQMRMQL (SEQ ID NO:100) | |
| CGQSKVIC (SEQ ID NO:101) | |
| KVLPIPQQVVPY (SEQ ID NO:102) | |
| RAVPVQALL (SEQ ID NO:103) | |
| LNQELL (SEQ ID NO:104) | |
| TVQQEL (SEQ ID NO:105) | |
| VHHQKLV (SEQ ID NO:106) | |

There is also the opportunity to derivatize protein or peptide substrates with non-peptide, organic amide and amine compounds making them substrates for transglutaminase crosslinking. Such molecules allow for the synthesis of high molecular weight carrier molecules with multiple pendant alkane carboxamides and alkane amines. Support for this comes from the fact that pentyl amine, putrescine and cadaverine can all participate in transglutaminase crosslinking reactions with a peptide or protein-derived glutamine. Derivatizing these compounds with biotin or dansyl groups on the distal carbon from the amine does not abolish their reactivity. Therefore, they can be grafted onto a synthetic polymer, for example, or suitably modified to be co-polymerized with other monomers while retaining their crosslinking activity. Similar strategies would apply to the derivatization of a polymer chain with a pendent amide that would be utilized as a glutamine donor.

Tissue Adhesives and Sealants

Polymeric materials having multiple sequences which are capable of covalent cross-linking by enzymatic reaction have been produced. One use of such compositions is in the formulation of tissue adhesives and sealants for medical applications. There are a number of factors to be considered in both the design and selection of the polymeric compositions to be used as well as the additional components comprising the final product in order to optimize its utility.

As one example of a tissue adhesive or sealant, the products comprise two principal components which are mixed prior to or simultaneously with the product's application. One component contains the factor XIIIa cross-linkable substrate and the other contains factor XIIIa. Factor XIIIa can be produced by the reaction of blood-derived factor XIII and thrombin. Factor XIIIa has been produced by means of recombinant DNA technology (Board, P. G., et al., *Thrombosis and Haemostasis*, 63 (2): 235–240 (1990)). The use of recombinant human factor XIIIa in a tissue adhesive or sealant does not require the use of thrombin.

Using fibrin glue as a model, polymeric compositions have been described which are designed to incorporate the adhesive activity of fibrin with the opportunity to modify its properties through an increased number of available cross-linking sites to accelerate the set time and increase the mechanical strength of the final products. However, the speed and degree at which cross-linking will occur is limited by one of the same factors that limits the speed of fibrin cross-linking: the size of factor XIIIa (160 kDa). It is known that activated factor XIIIa can be digested with trypsin to yield a 51 kDa single chain fragment which has fibrin binding and transglutaminase activity (Greenberg, C. S., et al., *Biochem. J.* (1988) 256: 1013–1019). Therefore, to increase the speed and density of cross-linking, it is desireable to use a truncated, human factor XIIIa which can be prepared by conventional or recombinant means.

An adhesive matrix of increased density and increased strength can be achieved by using a mixture of higher and lower molecular weight polymeric compositions. For example, where the polymeric compositions are polymers produced by conventional chemical synthesis (protein or otherwise), reaction conditions are used to produce polymers with a range of molecular weights. Where the polymeric compositions are recombinant protein polymers, clones producing cross-linkable substrates of discrete molecular weight ranging from 10–100 kDa (or greater) can be isolated depending upon the number of monomer sequences which are inserted in the final gene.

The polymeric compositions may include additional peptide units to confer improved physical and chemical adhesion to tissue and better handling and mechanical properties. These amino acid sequences may be of de novo design or derived from natural proteins, particularly human proteins. Sequences providing such functions have been identified in the literature. By way of example, decreased setting times may be achieved by inclusion of peptide units which improve the polymeric composition's cohesivity through the ability to bind or chelate complexing agents (e.g. multivalent ions such as calcium, zinc, silver, iron or other metal ions). Calcium binding sites have been identified in calmodulin. Complexing agents of low molecular weight can rapidly diffuse through the developing cross-linked matrix. Additional cohesivity can be achieved by inclusion of peptides containing complementary charges which may form interstrand salt bridges. Additional adhesive and cohesive stability may be achieved by inclusion of peptides containing chemical cross-linking units such as those containing cysteine which can undergo disulfide bond formation under mild oxidation conditions.

It is desireable for the tissue adhesive or sealant to promote hemostasis. Amino acid sequences which promote the adhesion of platelets will improve the hemostasis properties of the product. The amino acid sequence of Peptide 93.3 is known to bind to platelets. A platelet binding sequence has also been identified in thrombospondin. The addition of amino acid sequences containing the RGD cell attachment domain of fibronectin will promote the attachment and migration of many mammalian cells.

It is important for the tissue adhesive or sealant not to interfere with the normal wound healing process. It should be resorbed by the body as the healing process is taking place. By using polymeric compositions having differing numbers of amino acid sequences which are proteolytic cleavage sites, the resorption rate of the product can be adjusted. The sequences may be specifically cleaved by one or more blood born or tissue associated proteases such as tissue plasminogen activator (tPA), thrombin, and plasmin. By making the polymeric compositions more or less susceptible to plasmin degradation, plasmin inhibitors like aprotinin which delay the degradation of fibrin are also unnecessary. Such inhibitors have raised safety concerns.

To increase the adhesion to tissues, peptides from human collagen, fibrinopeptides, collagen binding sequences from fibronectin and other tissue binding proteins such as collagenase, and peptides with binding activity to saccharides or glycosaminoglycans and glycoproteins found in tissues may be used.

Blood clotting will be prevalent in many applications for a tissue adhesive or sealant. Therefore, improving the product's ability to adhere to bloody tissues or tissues which have progressed to early stages of fibrin clotting is desireable. By way of example, PPAS1-B was modified to include an amino acid sequence providing binding to fibrin via a noncovalent affinity for fibrin alpha chain (see PPAS1-D). Fibrin gamma chain residues 399-420 (POLSITE) confer the ability to polymerize adjacent fibrin molecules through their specific interaction with the amino terminal residues of fibrin alpha chain.

The compositions have mechanical integrity and can be used to form a variety of objects. The compositions have mechanical strength which allows them to find numerous applications for use internally in mammalian hosts. Rates of cross-linking or setting-up can be controlled. The compositions may be prepared in advance leaving out one component, so that the composition may be activated by adding the missing component, e.g. enzyme, small cross-linking molecule, or polymer. The compositions are physiologically acceptable, easily manipulated as solutions, dispersions or powders, and can provide strong bonding. The subject compositions afford the opportunity to introduce additional functional capabilities into the compositions, such as cell binding, chemoattractants, etc.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A recombinant protein polymer of a molecular weight in the range of 15 to 250 kD comprised of naturally occurring repetitive units from 3 to 18 amino acids and at least two enzyme recognition sequences separated by at least 25 intervening amino acids, said recognition sequences comprising a glutamine capable of enzyme catalyzed isopeptide formation.

2. A recombinant protein polymer according to claim 1, comprising at least three of said enzyme recognition sequences, separated by the same intervening sequence.

3. A recombinant protein polymer according to claim 2, wherein the intervening sequences comprise a naturally occurring functional sequence selected from the group consisting of the fibronectin binding site and the laminin binding site.

4. A recombinant protein polymer according to claim 1, wherein said repetitive units have the collagen motif of every third amino acid being glycine.

5. A recombinant protein polymer according to claim 1, wherein said repetitive units consist of at least one fibroin or elastin repetitive unit.

6. A recombinant protein polymer of from 35 kD to 250 kD comprising as a backbone alternating sequences comprising (1) repetitive units having the collagen motif of every third amino acid being glycine and (2) enzyme recognition sequences of from about 3 to 60 amino acids, said enzyme recognition sequences comprising an amino acid residue selected from the group consisting of glutamine and lysine which is capable of enzyme catalyzed isopeptide formation.

7. A recombinant protein polymer according to claim 6, wherein said enzyme recognition sequences further comprise a fibrin gamma polsite.

8. A recombinant protein polymer of a molecular weight in the range of 15 to 250 kD comprising naturally occurring repetitive units from 3 to 18 amino acids and at least 2 pendent groups, said pendent groups comprising a glutamine and/or lysine capable of enzyme catalyzed isopeptide formation.

9. A recombinant protein polymer according to claim 8, wherein said polymer is collagen and said pendent groups are consensus sequences from casein or fibrin, said consensus sequences having the reactive lysine substituted with another amino acid.

10. A recombinant protein polymer according to claim 8, wherein said polymer is at least 35 kD.

11. A recombinant protein polymer according to claim 8, wherein said repetitive units have the collagen motif of every third amino acid being glycine.

12. A recombinant protein polymer according to claim 8, wherein said repetitive units consist of at least one of fibroin or elastin repetitive units.

13. A recombinant protein polymer according to claim 8, wherein said pendent groups comprise the sequence Leu-Gly-Pro-Gly-Gln-Ser-Lys-Val-Ile-Gly (SEQ ID NO:48).

14. A recombinant protein polymer of a molecular weight in the range of 35 to 250 kD comprising naturally occurring repetitive units from 3 to 18 amino acids and at least 2 pendent groups, said pendent groups comprising a lysine capable of enzyme catalyzed isopeptide formation.

15. A recombinant protein polymer according to claim 14, wherein said pendent groups comprise the sequence Gly-Gly-Leu-Lys-Gly-Gly-Gly (SEQ ID NO:71).

16. A composition comprising a recombinant protein polymer according to claim 1 and a cross-linking compound other than said recombinant protein polymer said cross-linking compound comprising at least two reactive groups capable of enzyme catalyzed isopeptide formation with said glutamine.

17. A composition according to claim 18, wherein said cross-linking compound is a protein polymer comprising a plurality of lysines.

18. A composition according to claim 18, wherein said cross-linking compound is a molecule of less than 5 kD comprising at least two primary amino groups.

19. A composition comprising a recombinant protein polymer according to claim 1 and Factor XIII or Factor XIIIa.

20. A recombinant protein polymer of from 15 to 250 kD, comprising a repetitive amino acid backbone of repetitive units having the collagen motif of every third amino acid being glycine, fibroin motif, elastin motif or keratin motif, and at least two enzyme recognition sequences comprising a glutamine capable of enzyme catalyzed isopeptide formation, separated by an intervening sequence of at least 25 amino acids.

21. A recombinant protein polymer according to claim 20, wherein said enzyme recognition sequence is in said amino acid backbone.

22. A recombinant protein polymer according to claim 20, wherein said enzyme recognition sequence is pendent from said amino acid backbone.

23. A recombinant protein polymer according to claim 20, wherein said repetitive unit has the collagen motif of every third amino acid being glycine.

24. A recombinant protein polymer according to claim 23, wherein said enzyme recognition sequence is the casein recognition sequence.

25. A recombinant protein polymer according to claim 20, further comprising a fibrin gamma polsite in an intervening sequence.

26. A recombinant protein polymer of from 35 to 250 kD, comprising a repetitive amino acid backbone of repetitive units having the collagen motif of every third amino acid being glycine and being from 10 to 45% proline, and at least two enzyme recognition sequences comprising a glutamine capable of enzyme catalyzed isopeptide formation, separated by an intervening sequence of at least 25 amino acids.

27. A recombinant protein polymer according to claim 26, wherein said enzyme recognition sequence is the fibrinogen or casein sequence.

28. A recombinant protein polymer according to claim 27, wherein lysine present in said enzyme recognition sequence is substituted with another amino acid.

29. A recombinant protein polymer according to claim 26, wherein said intervening sequence comprises a fibrin gamma polsite.

\* \* \* \* \*